(12) United States Patent
Miller et al.

(10) Patent No.: US 10,674,699 B2
(45) Date of Patent: *Jun. 9, 2020

(54) ENDOPHYTE ENHANCED SEEDLINGS WITH INCREASED PEST TOLERANCE

(71) Applicant: IRVING LICENSING, INC., St. John (CA)

(72) Inventors: John David Miller, Ottawa (CA); Greg William Adams, Sussex Corner (CA)

(73) Assignee: Irving Licensing Inc., Saint John (CA)

( * ) Notice: Subject to any disclaimer, the term of this patent is extended or adjusted under 35 U.S.C. 154(b) by 459 days.

This patent is subject to a terminal disclaimer.

(21) Appl. No.: 15/389,125

(22) Filed: Dec. 22, 2016

(65) Prior Publication Data

US 2017/0164621 A1 Jun. 15, 2017

Related U.S. Application Data

(63) Continuation of application No. 13/745,427, filed on Jan. 18, 2013, now Pat. No. 9,549,528, which is a continuation of application No. 12/447,217, filed as application No. PCT/CA2007/001878 on Oct. 24, 2007, now Pat. No. 8,455,395.

(60) Provisional application No. 60/853,745, filed on Oct. 24, 2006.

(30) Foreign Application Priority Data

Oct. 24, 2006  (CA) ..................................... 2562175
Oct. 25, 2006  (AU) ............................... 2006233180

(51) Int. Cl.
*A01H 17/00* (2006.01)
*A01H 7/00* (2006.01)
*C12R 1/645* (2006.01)

(52) U.S. Cl.
CPC .............. *A01H 17/00* (2013.01); *A01H 7/00* (2013.01); *C12R 1/645* (2013.01)

(58) Field of Classification Search
CPC .................................................... A01H 17/00
See application file for complete search history.

(56) References Cited

U.S. PATENT DOCUMENTS

| | | | |
|---|---|---|---|
| 4,940,834 A | 7/1990 | Hurley et al. | |
| 5,723,720 A | 3/1998 | Brede et al. | |
| 5,880,343 A | 3/1999 | Hiruma et al. | |
| 6,180,855 B1 | 1/2001 | Hiruma et al. | |
| 6,911,338 B2 | 6/2005 | Strobel et al. | |
| 7,037,879 B2 | 5/2006 | Imada et al. | |
| 7,070,985 B2 | 7/2006 | Strobel et al. | |
| 7,084,331 B2 | 8/2006 | Isawa et al. | |
| 7,192,939 B2 | 3/2007 | Strobel et al. | |
| 7,214,509 B2 | 5/2007 | Schnoor et al. | |
| 8,455,395 B2 * | 6/2013 | Miller ...................... | A01H 3/00 504/117 |
| 2003/0186425 A1 | 10/2003 | Strobel et al. | |
| 2004/0018168 A1 | 1/2004 | Strobel et al. | |
| 2004/0141955 A1 | 7/2004 | Strobel et al. | |
| 2004/0185031 A1 | 9/2004 | Strobel et al. | |
| 2004/0206697 A1 | 10/2004 | Strobel et al. | |
| 2005/0150024 A1 | 7/2005 | West et al. | |
| 2005/0220769 A1 | 10/2005 | Strobel et al. | |
| 2006/0019295 A1 | 1/2006 | Presting | |
| 2006/0121593 A1 | 6/2006 | Christensen et al. | |
| 2006/0127346 A1 | 6/2006 | Strobel et al. | |
| 2006/0127347 A1 | 6/2006 | Strobel et al. | |
| 2006/0134762 A1 | 6/2006 | Puri et al. | |
| 2007/0006341 A1 | 1/2007 | Wagner et al. | |
| 2007/0118927 A1 | 5/2007 | Bryan et al. | |
| 2007/0142226 A1 | 6/2007 | Franco | |
| 2009/0181447 A1 | 7/2009 | Christensen et al. | |
| 2012/0198590 A1 | 8/2012 | Miller et al. | |
| 2013/0219569 A1 | 8/2013 | Miller et al. | |

FOREIGN PATENT DOCUMENTS

| | | |
|---|---|---|
| WO | 90/13224 | 11/1990 |
| WO | 2005/009360 | 2/2005 |

OTHER PUBLICATIONS

Miller et al, Mycological Research 106(4): 471-479 (Year: 2002).*
Sumarah et al, Mycologia 97(4): 770-776 (Year: 2005).*
Berube et al, Proceedings of the X International Symposium on Biological Control of Weeds, Session 3 abstracts, p. 241 (Year: 2000).*
Jumpponen et al, Mycorrhiza 7: 261-265 (Year: 1998).*
Findlay et al, Journal of Natural Products 1995, 58(2): 197-200 (Year: 1995).*
Clark et al, Mycological Research 93(4): 508-512 (abstract only). (Year: 1989).*
Ganley, R.J. et al., "Endophyte-mediated resistance against white pine blister rust in Pinus monticola", Forest Ecology and Management, 2008, 255: 2751-2760.
Latch, G.C.M. and Christensen M.J., "Artificial infection of grasses with endophytes", Ann. appl. Biol., 1985, 107: 17-24.
Schardl, C.L., "Epichloe Species: Fungal Symbionts of Grasses", Annu. Rev. Phytopathol., 1996, 34: 109-30.
Sumarah, M.W., "Spread and persistence of a rugulosin-producing endophyte in Picea glauca seedlings", Mycol. Res., 2008, 112: 731-736.
Wille, P. et al., "Mixed inoculation alters infection success of strains of the endophyte Epichloe bromicola on its grass host Bromus erectus", Proc. R. Soc. Lond. B, 2002, 269: 397-402.
"Phialocephala scopiformis strain CBS 468.94 16S ribosomal RNA gene, partial sequence; internal transcribed spacer 1, 5.8S ribosomal RNA gene and internal transcribed spacer 2, complete sequence; and 28S ribosomal RNA gene, partial sequence.", Apr. 11, 2002, Database EMBL, retrieved from EBI. Accession No. EMBL: AF486126.
"*Ascomycete* sp. HK-S178 ITS1, 5.8S rNA gene and ITS2, isolate S178", Sep. 5, 2005, Database EMBL, retrieved from EBI. Accession No. EMBL: AM084517.

(Continued)

*Primary Examiner* — David H Kruse
(74) *Attorney, Agent, or Firm* — Bereskin & Parr LLP; Carmela De Luca

(57) ABSTRACT

The invention provides methods for preparing a conifer seedling with increased tolerance to a pest. A conifer seedling is inoculated with an isolated endophyte when the conifer seedling is susceptible to colonization by the endophyte.

17 Claims, 11 Drawing Sheets
Specification includes a Sequence Listing.

(56) References Cited

OTHER PUBLICATIONS

Miller J.D. et al.: 'Needles of white spruce inoculated with rugulosin-producing endophytes contain rugulosin reducing spruce budworm growth rate' Mycol. Res. vol. 106, No. 4, Apr. 2002, pp. 471-479.

Sumarah M.W. et al. Measurement of a rugulosin-producing endophyte in white spruce seedlings. Mycologia vol. 97, No. 4, 2005, pp. 770-776.

Stefani F.O.P., and Berube J.A. Foliar endophyte biodiversity in natural Picea glauca stands in south Quebec area. Database Genbank [Online] May 26, 2004. Database accession No. (AY561216).

Watanabe K. et al. Analysis of endophytic fungi in a leaf of Japanese andromeda (*Pieris japonica* (Thunb.) D.Don). Database Genbank [Online] Nov. 17, 2004. Database accession No. (AB179774).

Sokolski S. et al. Biodiversity of foliar fungal endophytes of Picea mariana. Database Genbank [Online] Apr. 18, 2005. Database accession No. (AY971727).

Lim Y.W. et al. Determining fungal diversity on Dendroctonus ponderosae and Ips pini attacking lodgepole pine using cultural and molecular methods. Database Genbank [Online] Sep. 30, 2005. Database accession No. (AY761179).

Sokolski S. et al. Biodiversity of foliar fungal endophytes of Picea mariana. Database Genbank [Online] Apr. 18, 2005. Database accession No. (AY971709).

Sokolski S. et al. A fungal endophyte of black spruce (*Picea mariana*) needles is also an aquatic hyphomycete. Mol. Ecol. 2006, vol. 15, No. 7, pp. 1955-1962 (Database accession Nos. (AY746345, AY746350 and AY746341).

Lygis V. et al. Silvicultural and pathological evaluation of Scots pine afforestations mixed with deciduous trees to reduce the infections by *Heterobasidion annosum* s.s. For. Ecol. Manage vol. 201, No. 2-3, pp. 275-285, 2004. Database accession No. (AY590791).

Sokolski S. et al. Biodiversity of foliar fungal endophytes of Picea mariana. Database Genbank [Online] Apr. 18, 2005. Database accession No. (AY971690).

Sanchez Marquez S. et al. The endophytic assemblage of Dactylis glomerata. Database Genbank [Online] May 12, 2006 Database accession No. (AM262390).

Ganley R.J., and Newcombe G. Fungal endophytes in seeds and needles of Pinus monticola. Mycol. Res. vol. 110, No. Part 3, pp. 318-327, Mar. 2006. Database accession No. (AY465453).

Hoffman M.T., and Arnold A.E. Geographic locality and host identity shape fungal endophyte communities in cupressaceous trees. Mycol. Res. vol. 112, No. Part 3, pp. 331-344, Mar. 14, 2007. Gebbabj Acc, Bi. EF419976.

Higgins K.L. et al. Phylogenetic relationships, host affinity, and geographic structure of boreal and arctic endophytes from three major plant lineages. Mol. Phylogenet. Evol. vol. 42, No. 2, pp. 543-555, Nov. 21, 2006. Database accession Nos. DQ979745, DQ979778 and DQ979545.

Findlay J.A. et al. Insect toxins from spruce endophytes. Can. J. Chem. vol. 81, No. 4, 2003, pp. 284-292.

Clark C.L. et al. Toxicity of conifer needle endophytes to spruce budworm. Mycological Research, vol. 94, No. 4, pp. 508-512, 1989.

Ganley, R.J., et al.; "A community of unknown, endophytic fungi in western white pine", PNAS, vol. 101, No. 27, Jul. 6, 2004, pp. 10107-10112.

Azevedo, J.L. et al.; "Endophytic microorganisms: a review on insect control and recent advances on tropical plants". EJB Electronic Journal of Biotechnology. Apr. 15, 2000, vol. 3, No. 1, pp. 40-65.

Schulz, B. et al.; "The endophytic continuum". Mycol Res. Jun. 2005, vol. 109, No. 6, pp. 661-686.

Berube, J.; "Fungal Endophytes: unsuspected potential" Branching Out, Jul. 16, 2007, modified Sep. 4, 2007, No. 34.

Breen et al.; "Rugulosin, a Crystalline Colouring Matter of Penicillium Rugulosum" Thom. Studies in the Biochemistry of Microorganisms, 1955, vol. 60, pp. 618-626.

Hocking, D.; "Pythium Intermedium, a newly recognized pathogen of coniferous seedlings in Canada" Can. Plant. Dis. Surv., Dec. 1970, vol. 60, No. 4, pp. 121-123.

Berube, J.A. et al.; "Endophytic Fungal Flora from Eastern White Pine Needles and Apple Tree Leaves as a Means of Biological Control for White Pine Blister Rust". Finnish Forest Research Institute, Research Papers 712:305-309, 1998.

Findlay, J.A. et al.; "Novel Diterpenoid Insect Toxins from a Conifer Endophyte", Journal of Natural Products, Feb. 1995, vol. 58, No. 2, pp. 197-200.

Jumpponen, A. et al.; "Micorrhizal Functioning of Phialocephala fortinii with Pinus Contorta on Glacier Forefront Soil: Interactions with Soil Nitrogen and Organic Matter", 1998, vol. 7, pp. 261-265.

Geils, Brian W. et al. White pines, Ribes, and blister rust: a review and synthesis. Forest Pathology, 40(2010) 147-185.

Zeglen S. et al. Silvicultural management of white pines in western North America. Forest Pathology, 40 (2010) 347-368.

Bérubé J. A. Cronartium ribicola J.C. Fischer, White Pine Blister Rust (*Cronartiaceae*). Biological Control Programmes in Canada, 1981-2000, Chapter 87, pp. 446-448.

Miller, David J. et al. Horizontal transmission of the Picea glauca foliar endophyte Phialocephala scopiformis CBS 120377. Fungal ecology 2 (2009) 98-101.

Miller, David J. and Sumarah, Mark W. Effect of a Rugulosin-producing Endophyte in Picea glauca on Choristoneura fumiferana. J. Chem. Ecol. 2007.

Bucheli, E. et al. "Host-specific differentiation in the anther smut fungus *Microbotryum violaceum* as revealed by microsatellites" J. Evol. Biol.13, 188-198, 2000.

Calhoun L.A. et al, "Metabolites toxic to spruce budworm from balsam fir needle endophytes", Mycological Research, 1992, 96:281-286.

Findlay J.A. et al., "Insect toxins from an endophytic fungus from Wintergreen", J Natural Products, 1997, 60:1214-1215.

Findlay J.A. et al., "Insect toxins from conifer endophytes", Proceedings of the 1st International Congress on the Chemistry of Natural Products (ICNP-2002), Karadeniz Technical University, Trabzon, Turkey, 2002, pp. 13-16.

Findlay J.A. et al., "Bioactive isocoumarins and related metabolites from conifer endophytes", J Natural Products, 1995, 58:1759-1766.

Miller J.D. et al., "Fusarium toxins in field corn. I. Time course of fungal growth and production of deoxynivaneol and other mycotoxins", Can J Botany, 1983, 61:3080-3087.

Miller J.D. et al., "Observations on fungi associated with spruce budworm infested balsam fir needles", Can J Forest Res, 1985, 15:896 901.

Miller J.D. et al., "Secondary metabolites of Fusarium venenatum strains with deletions in the Tri5 gene encoding trichodiene synthetase", Mycologia, 2000, 92:764-771.

Sumarah, M.W. et al., "Characterization of polyketide metabolites from foliar endophytes of Picea glauca", J. Nat. Prod., 2008, 71, No. 8, pp. 1393-1398.

Wilson R. et al., "Genetic diversity among natural populations of endophytic Lophodermium pinastri from Pinus resinosa", Mycol. Res, 1994, 98(7):740-744.

\* cited by examiner

[1] un-colonized white spruce needles that have been powdered and freeze dried

SEQUENCE LISTING

```
<160> NUMBER OF SEQ ID NOS: 28

<210> SEQ ID NO 1
<211> LENGTH: 548
<212> TYPE: DNA
<213> ORGANISM: Artificial Sequence
<220> FEATURE:
<223> OTHER INFORMATION: Fungus

<400> SEQUENCE: 1
cattaataag gatgctggaa gggggtgagc ccacgcctcc cctagacggt ataccccacc      60
cgtgtctatc tactcttgtt gctttggcag gccgtggcct ccactgtggg ctctgcctgc     120
atgtgcctgc cagaggatta aactctgaat tttagtgatg tctgagaact atctaatagt     180
taaaactttc aacaacggat ctcttggttc tggcatcgat gaagaacgca gcgaaatgcg     240
ataagtaatg tgaattgcag aattcagtga atcatcgaat ctttgaacgc acattgcgcc     300
ctgtggtatt ccgcagggca tgcctgttcg agcgtcatta taaccactca agcctggctt     360
ggtgttgggg tttgcggttc cgcagccoct aaaatcagtg gcggtgccgg tgggctctac     420
gcgtagtaaa tctcctcgcg attgagttcc cccggtggcc tgccagaacc cccaattttt     480
acaggttgac ctcggatcag gtagggatac ccgctgaact taagcatatc ataaaaagcc     540
ggaaggaa                                                             548

<210> SEQ ID NO 2
<211> LENGTH: 541
<212> TYPE: DNA
<213> ORGANISM: Artificial Sequence
<220> FEATURE:
<223> OTHER INFORMATION: Fungus
<220> FEATURE:
<221> NAME/KEY: misc_feature
<222> LOCATION: (396)..(396)
<223> OTHER INFORMATION: n is a, c, g, or t
<220> FEATURE:
<221> NAME/KEY: misc_feature
<222> LOCATION: (528)..(528)
<223> OTHER INFORMATION: n is a, c, g, or t

<400> SEQUENCE: 2
cattacaagg ttcttagtga catctcgaaa gagatccctc ccaagtatcc cacccgtgtc      60
tatatactct tgttgctttg gcggggcgtg gcctccactg cgggctctgc tgtacgtac     120 ccgccagagg accaaactct gaatgttagt gatgtctgag tactatataa tagttaaaac    180
tttcaacaac ggatctcttg gttctggcat cgatgaagaa cgcagcgaaa tgcgataagt    240
aatgtgaatt gcagaattca gtgaatcatc gaatctttga acgcacattg cgccccgtgg    300
tattccgcgg ggcatgcctg ttcgagcgtc attataacca ctcaagccta gcttggtgtt    360
ggggcacgcg gtttcgcggc cctcaaatcc agtggnggcg ccggtgggct ctaagcgtag    420
taaaacttct cgcttcaggg tccctcggt ggctcgccag aacctccaac tcttttaagg    480
```
ttgacctcgg atcaggtagg datacccgct gaacttaagc atatcatnaa gcggaaggaa    540
a                                                                    541

<210> SEQ ID NO 3
<211> LENGTH: 555
<212> TYPE: DNA
<213> ORGANISM: Artificial Sequence
<220> FEATURE:
<223> OTHER INFORMATION: Fungus

<400> SEQUENCE: 3
cattacagag ttatcaaaac tcccaaaccc atgtgaacat acctcgcgtt gctcggaggt     60
ggcgtctccc cgtaagaacc taccctgtag gaccttaccc ggtagacgac cctgccgacg    120
gccccgaaac tctgttttat agcattaaac ttctgaaaat ataactaaat aagttaaaac    180
tttcaacaac ggatctcttg gttctggcat cgatgaagaa cgcagcgaaa tgcgataagt    240
aatgtgaatt gcagaattca gtgaatcatc gaatctttga acgcacattg cgcccactag    300
tattctggtg ggcatgcctg ttcgagcgtc atttcaaccc ttaagcccct gttgcttagc    360
gttaggagct taccggaact ctctggtagc tccccaaagt cagtggcgga ggttcgcact    420
ccagacgtag tagcttttac acgtcgcctg tagcgcgggc cggtccctg ccgtaaaaca     480 ccccaatttt tataggttga cctcggatca ggtaggaata cccgctgaac ttaagcatat    540
caataagcgg aggaa                                                     555

<210> SEQ ID NO 4
<211> LENGTH: 484
<212> TYPE: DNA
<213> ORGANISM: Artificial Sequence
<220> FEATURE:
<223> OTHER INFORMATION: Fungus

<400> SEQUENCE: 4
cattaaagaa tacaaagccc ctccgggcac tattctcacc ctatgtttac caaactttgt     60
tgctttggcg gaaacgcaga ggaccgaaac ccttgaatct ctgccgtctg agtcactata    120
taatagttaa aactttcaac aacggatctc ttggttctgg catcgatgaa gaacgcagcg    180
aaatgcgata agtaatgtga attgcagaat tcagtgaatc atcgaatctt tgaacgcaca    240
ttgcgccctc tggcattccg gaggcatgcc tgttcgagcg tcattacaac cctcaagctc    300
tgcttggtat tgggctgggc tcttccaaag gcctgcctc aaaattagtg gcggcaccgt     360
ctgaccttaa gcgcagtaat gctcgtcgct tcttaggttc cgggcggcgc ttgctaacaa    420
cccccaccat tatcaggttg acctcggatc aggtagggat acccgctgac ttatctatca    480
ttaa                                                                 484

<210> SEQ ID NO 5
<211> LENGTH: 514
<212> TYPE: DNA
<213> ORGANISM: Artificial Sequence
<220> FEATURE:
<223> OTHER INFORMATION: Fungus
<220> FEATURE:
<221> NAME/KEY: misc_feature
<222> LOCATION: (502)..(502)
<223> OTHER INFORMATION: n is a, c, g, or t
<220> FEATURE:
<221> NAME/KEY: misc_feature
<222> LOCATION: (504)..(504)
<223> OTHER INFORMATION: n is a, c, g, or t
<220> FEATURE:
<221> NAME/KEY: misc_feature
<222> LOCATION: (510)..(510)
<223> OTHER INFORMATION: n is a, c, g, or t

<400> SEQUENCE: 5

```
cattaaagaa tatcaggctt cacagcccta ttctcaccct atgtatttga aacttcgttg      60
ctttggcagg cccctggctt cggctggaca gcgcctgcca gaggatctaa acccttgaat    120
ctctgctgtc tgagtactac acaatagtta aaactttcaa caacggatct cttggttctg    180
gcatcgatga agaacgcagc gaaatgcgat aagtaatgtg aattgcagaa ttcagtgaat    240
catcgaatct ttgaacgcac attgcgccct ctggtattcc gggggggcatg cctgttcgag    300
cgtcattaca accctcacgc tctgcgtggt gttgggcctg ccctaaaggg cttgcctcaa    360
aatcagtggc ggccgctgtt cgaccccctaa gcgtagtaat tattcgtcgc ttctgggcta    420
gagcaagcct gctaggaacc cccaccttca aaggttgacc tcggatcagg tagggatacc    480
cgctgaactt aagcatatca tnangcggan gaaa                                 514
```

<210> SEQ ID NO 6
<211> LENGTH: 534
<212> TYPE: DNA
<213> ORGANISM: Artificial Sequence
<220> FEATURE:
<223> OTHER INFORMATION: Fungus
<220> FEATURE:
<221> NAME/KEY: misc_feature
<222> LOCATION: (40)..(40)
<223> OTHER INFORMATION: n is a, c, g, or t
<220> FEATURE:
<221> NAME/KEY: misc_feature
<222> LOCATION: (157)..(157)
<223> OTHER INFORMATION: n is a, c, g, or t

<400> SEQUENCE: 6

```
cattacagag aacttgccct tcccccgtag atctcaaaan ctttgtttac attacccttg      60
ttgctttggc aggcccgtct ctcgggaccg ccggcttcgg ctggcccgcg cctgccagag    120
gatcttaaac tcttgtttaa atgtcgtctg agtactntat aataagttaa aactttcaac    180
aacggatctc ttggttctgg catcgatgaa gaacgcagcg aaatgcgata agtaatgtga    240
attgcagaat tcagtgaatc atcgaatctt tgaacgcaca ttgcgccctc tggtattccg    300
ggggcatgc ctgttcgagc gtcattacaa ccctcaagct ctgcttggta ttgggcgtca    360
ccgcttcggt gcgccttaaa atcagtggcg gtgccatccg gcttcaagcg tagtaattct    420
tctcgctctg gggatccggg tgtgtgcttg ccagcaaccc ccaatttatc aaaggttgac    480
ctcggatcag gtagggatac ccgctgaact taagcatatc aataagcgga ggaa           534
```

<210> SEQ ID NO 7
<211> LENGTH: 561
<212> TYPE: DNA
<213> ORGANISM: Artificial Sequence
<220> FEATURE:
<223> OTHER INFORMATION: Fungus
<220> FEATURE:
<221> NAME/KEY: misc_feature
<222> LOCATION: (25)..(25)
<223> OTHER INFORMATION: n is a, c, g, or t

<400> SEQUENCE: 7

```
cattactgag ttagggttct tcccnagccc aacctccaac cctttgttta atttaccttg      60
ttgctttggc aggcccgcct ttcggggccg ccggggatgt tcagtcatct ctggccagtg    120
cttgccagta gccacttcaa attcttttta actatgtcgt ctaaacaatt aaatcaaaat    180
```

-continued

| | |
|---|---|
| ttaattaaaa ctttcaacaa cggatctctt ggttctggca tcgatgaaga acgcagcgaa | 240 |
| atgcgataag taatgtgaat tgcagaattc agtgaatcat cgaatctttg aacgcacatt | 300 |
| gcgcccttg tattccgaa gggcatgcct gttcgagcgt cattatcaac cctcaagccc | 360 |
| ggcttgttat tgggtcctgt atcgttaaaa gataggcccg aaagataatg gcggcgtcaa | 420 |
| gatagacccc aggtgcagcg agcttgctaa gcatacactg aggtggtcgt cttggcctgg | 480 |
| cccaacccca atttttctaa ggttgacctc ggatcaggta ggaatacccg ctgaacttaa | 540 |
| gcatatcatt aagcggagga a | 561 |

<210> SEQ ID NO 8
<211> LENGTH: 562
<212> TYPE: DNA
<213> ORGANISM: Artificial Sequence
<220> FEATURE:
<223> OTHER INFORMATION: Fungus

<400> SEQUENCE: 8

| | |
|---|---|
| cattactgag ttagggttct ctcagcccaa acctccaacc ctttgtttaa tttaccttgt | 60 |
| tgctttggca ggcccgcctt tcggggccgc cggggatgtt cagtcatctc tggccagtgc | 120 |
| ttgccagtag ccacttcaaa ttcttttaa ctatgtcgtc taaacaatta aatcaaaatt | 180 |
| taattaaaac tttcaacaac ggatctcttg gttctggcat cgatgaagaa cgcagcgaaa | 240 |
| tgcgataagt aatgtgaatt gcagaattca gtgaatcatc gaatctttga acgcacattg | 300 |
| cgccctttgg tattccgaag gcatgcctg ttcgagcgtc attatcaacc ctcaagcccg | 360 |
| gcttgttatt gggtcctgta tcgttaaaaa gataggcccg aaagataatg gcggcgtcaa | 420 |
| gatagacccc aggtgcagcg agcttgctaa gcatacactg aggtggtcgt cttggcctgg | 480 |
| cccaacccca atttttctaa ggttgacctc ggatcaggta ggaatacccg ctgaacttaa | 540 |
| gcatatcaat taagcggagg aa | 562 |

<210> SEQ ID NO 9
<211> LENGTH: 565
<212> TYPE: DNA
<213> ORGANISM: Artificial Sequence
<220> FEATURE:
<223> OTHER INFORMATION: Fungus
<220> FEATURE:
<221> NAME/KEY: misc_feature
<222> LOCATION: (25)..(25)
<223> OTHER INFORMATION: n is a, c, g, or t
<220> FEATURE:
<221> NAME/KEY: misc_feature
<222> LOCATION: (42)..(42)
<223> OTHER INFORMATION: n is a, c, g, or t
<220> FEATURE:
<221> NAME/KEY: misc_feature
<222> LOCATION: (55)..(55)
<223> OTHER INFORMATION: n is a, c, g, or t
<220> FEATURE:
<221> NAME/KEY: misc_feature
<222> LOCATION: (494)..(494)
<223> OTHER INFORMATION: n is a, c, g, or t
<220> FEATURE:
<221> NAME/KEY: misc_feature
<222> LOCATION: (557)..(557)
<223> OTHER INFORMATION: n is a, c, g, or t

<400> SEQUENCE: 9

| | |
|---|---|
| cattagaatg agagccggaa ccatnctcgt gggtcgaaag cncaaacgtg ccagntaagc | 60 |
| gcccgtaaac ctccaccctt gtatattatt ctttgttgct ttggtgggcc gcaagccttc | 120 |
| gggtgagcac cggcttcggc tggagagtgc ctgccagagg acccaactct gtaatttagt | 180 |

```
gatgtctgag tactattaaa tagttaaaac tttcaacaac ggatctcttg gttctggcat     240
cgatgaagaa cgcagcgaaa tgcgataagt aatgtgaatt gcagaattca gtgaatcatc     300
gaatctttga acgcacattg cgccctctgg tattccggag gcatgcctg ttcgagcgtc      360 attataacca atcacgcaag tggttttggg gcttgctatc tagcatccct taaaaacagt     420
ggcggtgcta tagggctctc agcgtagtaa ttattccgct tttgaaacct agacacacct     480
gtcaaacccc ccantctttt taaggttgac ctcggatcag gtagggatac ccgctgaact     540
taagcatatc aataaancgg aggaa                                           565
```

```
<210> SEQ ID NO 10
<211> LENGTH: 555
<212> TYPE: DNA
<213> ORGANISM: Artificial Sequence
<220> FEATURE:
<223> OTHER INFORMATION: Fungus

<400> SEQUENCE: 10
cattagaatg agagccggac catgtcgtgg gcgaaaaaac gtgccagtaa gcgcccgtaa      60
acctccaccc ttgtatatta ttctttgttg ctttggtggg ccgcaagcct tcggcgagca    120
ccggcttcgg ctggagagtg cctgccagag gacccaactc tgtaatttag tgatgtctga    180
gtactattaa atagttaaaa ctttcaacaa cggatctctt ggttctggca tcgatgaaga    240
acgcagcgaa atgcgataag taatgtgaat tgcagaattc agtgaatcat cgaatctttg    300
aacgcacatt gcgccctctg gtattccgga ggcatgcctg ttcgagcgtc attataacca    360
atcacgcaag tggttttggg gcttgctatc tagcatccct taaaaacagt ggcggtgcta    420
tagggctctc agcgtagtaa tcattccgct tttgaaacct agacacacct gtcaaacccc    480
ccaatctttt taaggttgac ctcggatcag gtagggatac ccgctgaact taagcatatc    540
ataaagcgga ggaga                                                     555
```

```
<210> SEQ ID NO 11
<211> LENGTH: 717
<212> TYPE: DNA
<213> ORGANISM: Artificial Sequence
<220> FEATURE:
<223> OTHER INFORMATION: Fungus
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (595)..(595)
<223> OTHER INFORMATION: n is a, c, g, or t
<220> FEATURE:
<221> NAME/KEY: misc_feature
<222> LOCATION: (598)..(601)
<223> OTHER INFORMATION: n is a, c, g, or t
<220> FEATURE:
<221> NAME/KEY: misc_feature
<222> LOCATION: (638)..(638)
<223> OTHER INFORMATION: n is a, c, g, or t
<220> FEATURE:
<221> NAME/KEY: misc_feature
<222> LOCATION: (641)..(641)
<223> OTHER INFORMATION: n is a, c, g, or t
<220> FEATURE:
<221> NAME/KEY: misc_feature
<222> LOCATION: (678)..(678)
```

<223> OTHER INFORMATION: n is a, c, g, or t

<400> SEQUENCE: 11

```
cattaatggt cnattgtgga gccntcagaa ggtatgctac ggcgtcattc gcagtgggac      60
caatagaatc cacgtatcag ggtggacccc tggaacccta cccgggttcc tcacgagttc     120
ggggcgtgag tctctggccc tatagacggg ccctaagagc ggccggggtt tacagccccc     180
aataccgaca tagtccttgg cccgccaagc gagccgatgc gtccacgctg gcgctcccct     240
tccaaacccc aaccettgaa tacctcacct ctgttgcctc ggcgggtacg ctcgccggtg     300
gacgcaaacc aaactcctgt cttaacggtg tagtctgagc aaacaaagta atagttaaaa     360
ctttcaacaa cggatctctt ggttctggca tcgatgaaga acgcagcgaa atgcgataag     420
tagtgtgaat tgcagaattc agtgaatcat cgaatctttg aacgcacatt gcgccctttg     480
gcatcccgaa gggcatgcct gttcgagcgt catttcacct ctcaagcgca gcttggtgtt     540
ggaggacgtc ccttcctata gaggggcccc tcctaaaatc atcggcgatt ctatnttnnn     600
ntctgagcgt agcacaaatt tcgctccccc ccccccncc nccgcgttgg gccgtgaaac     660
cacttcttca aggttgancc tcggatcaag gtagggaata cccegectga acttaaa      717
```

<210> SEQ ID NO 12
<211> LENGTH: 561
<212> TYPE: DNA
<213> ORGANISM: Artificial Sequence
<220> FEATURE:
<223> OTHER INFORMATION: Fungus
<220> FEATURE:
<221> NAME/KEY: misc_feature
<222> LOCATION: (552)..(552)
<223> OTHER INFORMATION: n is a, c, g, or t

<400> SEQUENCE: 12

```
cattagaatg agagccggac catgtcgtgg gtgaaagccc aaacgtgcca gtaagcgccc      60
gtaaacctcc acccttgtat attattcttt gttgctttgg tgggccgcaa gccttcgggc     120
gagcaccggc ttcggctgga gagtgcctgc cagaggaccc aactctgtaa tttagtgatg     180
tctgagtact attaaatagt taaaactttc aacaacggat ctcttggttc tggcatcgat     240
gaagaacgca gcgaaatgcg ataagtaatg tgaattgcag aattcagtga atcatcgaat     300
ctttgaacgc acattgcgcc ctctggtatt ccggagggca tgcctgttcg agcgtcatta     360
taaccaatca cgcgagtggt tttggggctt gctatctagc atcccttaaa acagtggcgg     420
tgctataggg ctctcagcgt agtaattatt cccgcttttg aaacctagac acacctgtca     480
gaaccoccaa ttttttaaggt tgacctcgga tcaggtaggg atacccgctg aacttaagct     540
tcatttaaag cnggaagaaa a                                                561
```

<210> SEQ ID NO 13
<211> LENGTH: 555
<212> TYPE: DNA
<213> ORGANISM: Artificial Sequence
<220> FEATURE:
<223> OTHER INFORMATION: Fungus
<220> FEATURE:
<221> NAME/KEY: misc_feature
<222> LOCATION: (336)..(336)
<223> OTHER INFORMATION: n is a, c, g, or t
<220> FEATURE:
<221> NAME/KEY: misc_feature
<222> LOCATION: (375)..(375)
<223> OTHER INFORMATION: n is a, c, g, or t

<400> SEQUENCE: 13

```
cattagaatg agagccggac catgtcgtgg gcgaaagccc aaacgtgcca gtaagcgccc      60
gtaaacctcc acccttgtat attattcttt gttgctttgg tgggccgcaa gccttcgggc     120
gagcaccggc ttcggctgga gagtgcctgc cagaggaccc aactctgtaa tttagtgatg     180
tctgagtact attaaatagt taaaactttc aacaacggat ctcttggttc tggcatcgat     240
gaagaacgca gcgaaatgcg ataagtaatg tgaattgcag aattcagtga atcatcgaat     300
ctttgaacgc acattgcgcc ctctggtatt ccgganggca tgcctgttcg agcgtcatta     360
taaccaatca cgcangtggt ttggggcttg ctatctagc atcccttaaa acagtggcgg      420
tgctataggg ctctcagcgt agtaattatt ccgcttttga acctagacac acctgtcaga     480
accccaattt ttaaggttga cctcggatca ggtaggatac ccgctgaact taagcatatc     540
aataagcgga ggaaa                                                     555

<210> SEQ ID NO 14
<211> LENGTH: 560
<212> TYPE: DNA
<213> ORGANISM: Artificial Sequence
<220> FEATURE:
<223> OTHER INFORMATION: Fungus
<220> FEATURE:
<221> NAME/KEY: misc_feature
<222> LOCATION: (23)..(23)
<223> OTHER INFORMATION: n is a, c, g, or t
<220> FEATURE:
<221> NAME/KEY: misc_feature
<222> LOCATION: (34)..(34)
<223> OTHER INFORMATION: n is a, c, g, or t
<220> FEATURE:
<221> NAME/KEY: misc_feature
<222> LOCATION: (66)..(66)
<223> OTHER INFORMATION: n is a, c, g, or t
<220> FEATURE:
<221> NAME/KEY: misc_feature
<222> LOCATION: (418)..(418)
<223> OTHER INFORMATION: n is a, c, g, or t
<220> FEATURE:
<221> NAME/KEY: misc_feature
<222> LOCATION: (529)..(529)
<223> OTHER INFORMATION: n is a, c, g, or t
<220> FEATURE:
<221> NAME/KEY: misc_feature
<222> LOCATION: (534)..(534)
<223> OTHER INFORMATION: n is a, c, g, or t

<400> SEQUENCE: 14
cattactgag ttagggttct tcngagccca accnccaacc ctttgtttaa tttaccttgt      60
tgcttnggca ggcccgcctt tcggggccgc cggggatgtt cagtcatctc tggccagtgc     120
ttgccagtag ccacttcaaa ttcttttttaa ctatgtcgtc taaacaatta aatcaaaatt    180
taattaaaac tttcaacaac ggatctcttg gttctggcat cgatgaagaa cgcagcgaaa     240
tgcgataagt aatgtgaatt gcagaattca gtgaatcatc gaatctttga acgcacattg     300
cgcccttggg tattccgaag gcatgcctg ttcgagcgtc attatcaacc ctcaagcccg      360
gcttgttatt gggtcctgta tcgttaaaag ataggcccga aagataatgg cggcgtcnag    420
atagacccca ggtgcagcga gcttgctaag catacactga ggtggtcgtc ttggcctggc     480
ccaaccccaa tttttctaag gttgacctcg gatcaggtag gaatacccnc tgancttaag    540
catatcaata aggggaggaa                                                560

<210> SEQ ID NO 15
<211> LENGTH: 507
<212> TYPE: DNA
```

<213> ORGANISM: Artificial Sequence
<220> FEATURE:
<223> OTHER INFORMATION: Fungus

<400> SEQUENCE: 15

```
cattaccgag tgagggcttc ggtccgacct ccaaccctgt gtgaaccaaa cttgttgctt    60 cggggggcgac cctgccgcct cggcggcgcg gcgcccccga aggccatcaa acactgcatc   120
attgcgtcgg agtcgaagta aatcaaataa aactttcaac aacggatctc ttggttccag   180
catcgatgaa gaacgcagcg aaatgcgata agtaatgtga attgcagaat tcagtgaatc   240
atcgaatctt tgaacgcaca ttgcgccctc tggtattccg ggggcatgc ctgttcgagc    300 gtcatttcac cactcaagcc tggcttggta ttgggcgtcg cggctccgcg cgcctcaaag   360
tcttccggct gagctgtccg tctctacgcg ttgtggcaac tattcgcgtg ggaggtcggg   420
cggccgcggc cgttaaacct ttcacaggtt gacctcggat caggtaggga tacccgctga   480
acttaagcat atcattaagc ggaggaa                                       507
```

<210> SEQ ID NO 16
<211> LENGTH: 555
<212> TYPE: DNA
<213> ORGANISM: Artificial Sequence
<220> FEATURE:
<223> OTHER INFORMATION: Fungus

<400> SEQUENCE: 16

```
cattagaatg agagccggac catgtcgtgg gtgaaagccc aaacgtgcca gtaagcgccc    60
gtaaacctcc acccttgtat attattcttt gttgctttgg tgggccgcaa gccttcggcg   120
agcaccggct tcggctggag agtgcctgcc agaggaccca actctgtaat ttagtgatgt   180
ctgagtacta ttaaatagtt aaaactttca acaacggatc tcttggttct ggcatcgatg   240
aagaacgcag cgaaatgcga taagtaatgt gaattgcaga attcagtgaa tcatcgaatc   300
tttgaacgca cattgcgccc tctggtattc cggaggcatg cctgttcgag cgtcattata   360
accaatcacg cgagtggttt tggggcttgc tatctagcat cccttaaaaa cagtggcggt   420
gctatagggc tctcagcgta gtaattattc cgcttttgaa acctagacac acctgtcaga   480 accccccaatt tttaaggttg acctcggatc aggaggatac ccgctgaact taagcatatc   540
ataaggcgga ggaaa                                                    555
```

<210> SEQ ID NO 17
<211> LENGTH: 562
<212> TYPE: DNA
<213> ORGANISM: Artificial Sequence
<220> FEATURE:
<223> OTHER INFORMATION: Fungus
<220> FEATURE:
<221> NAME/KEY: misc_feature
<222> LOCATION: (26)..(26)
<223> OTHER INFORMATION: n is a, c, g, or t
<220> FEATURE:
<221> NAME/KEY: misc_feature
<222> LOCATION: (157)..(157)
<223> OTHER INFORMATION: n is a, c, g, or t
<220> FEATURE:
<221> NAME/KEY: misc_feature
<222> LOCATION: (159)..(159)
<223> OTHER INFORMATION: n is a, c, g, or t

<400> SEQUENCE: 17

```
cattactgag ttagggttct tccccnccca acctggaaaa aatttgttta atttaccttg    60
ttgctttgcc aggcccgcct ttcggggccg ccggggatgt tcagtcatct ctggccagtg   120
```

```
cttgccagta gccacttcaa attctttta actatgncnt ctaaacaatt aaatcaaaat        180
ttaattaaaa ctttcaacaa cggatctctt ggttctggca tcgatgaaga acgcagcgaa        240
atgcgataag taatgtgaat tgcagaattc agtgaatcat cgaatctttg aacgcacatt        300 gcgcccttg gtattccgaa gggcatgcct gttcgagcgt cattatcaac cctcaagccc         360
ggcttgttat tgggtcctgt atcgttaaaa gataggcccg aaagataatg gcggcgtcaa        420
gatagacccc aggtgcagcg agcttgctaa gcatacactg aggtggtcgt cttggcctgg        480
cccaacccca attttttctaa ggttgacctc ggatcaggta ggaatacccg ctgaacttaa       540
gcatatcaat aagcggagga aa                                                 562

<210> SEQ ID NO 18
<211> LENGTH: 555
<212> TYPE: DNA
<213> ORGANISM: Artificial Sequence
<220> FEATURE:
<223> OTHER INFORMATION: Fungus

<400> SEQUENCE: 18
cattaccaga gtgccctagg ctctccaacc cattgtgaac atacctatcg ttccctcggc        60
gggctcagcg cgcggtgcct ccgggctccg ggcgtccgcc ggggacaacc aaactctgat       120
tttattgtga atctctgagg ggcgaaagcc cgaaaacaaa atgaatcaaa actttcaaca       180
acggatctct tggctctggc atcgatgaag aacgcagcga aatgcgataa gtaatgtgaa       240
ttgcagaatt cagtgaatca tcgaatcttt gaacgcacat tgcgccccgcc ggcactccgg      300 cgggcatgcc tgtccgagcg tcatttcaac cctcaggacc cccttcgggg gggacctgg       360 tgctggggat cagcggcctc cgggcccctg tccccaaat tgagtggcgg tcgcgccgca       420
gcctcccctg cgtagtagca cacctcgcac cggagagcgg ctcggccacg ccgtgaaacc      480 cccaatttttt taaggttgac ctcggatcag gtaggaatac ccgctgaact taagcatatc     540
attaaagcgg aggaa                                                       555

<210> SEQ ID NO 19
<211> LENGTH: 560
<212> TYPE: DNA
<213> ORGANISM: Artificial Sequence
<220> FEATURE:
<223> OTHER INFORMATION: Fungus

<400> SEQUENCE: 19
cattactgag ttagggttct tctgagccca acctccaacc ctttgtttaa tttaccttgt        60
tgctttggca ggcccgcctt tcggggccgc cggggatgtt cagtcatctc tggccagtgc       120
ttgccagtag ccacttcaaa ttcttttaa ctatgtcgtc taaacaatta aatcaaaatt         180
taattaaaac tttcaacaac ggatctcttg gttctggcat cgatgaagaa cgcagcgaaa       240
tgcgataagt aatgtgaatt gcagaattca gtgaatcatc gaatctttga acgcacattg       300 cgcccttgg tattccgaag gcatgcctg ttcgagcgtc attatcaacc ctcaagcccg         360
gcttgttatt gggtcctgta tcgttaaaag ataggcccga agataatgg cggcgtcaag       420 atagaccccc ggtgcagcga gcttgctaag catacactga ggtggtcgtc ttggcctggc       480
ccaaccccaa ttttctaag gttgacctcg gatcaggtag gaatacccgc tgaacttaag      540
catatcataa agcggaggaa                                                  560

<210> SEQ ID NO 20
```

<211> LENGTH: 562
<212> TYPE: DNA
<213> ORGANISM: Artificial Sequence
<220> FEATURE:
<223> OTHER INFORMATION: Fungus
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (151)..(151)
<223> OTHER INFORMATION: n is a, c, g, or t
<220> FEATURE:
<221> NAME/KEY: misc_feature
<222> LOCATION: (156)..(156)
<223> OTHER INFORMATION: n is a, c, g, or t
<220> FEATURE:
<221> NAME/KEY: misc_feature
<222> LOCATION: (550)..(550)
<223> OTHER INFORMATION: n is a, c, g, or t

<400> SEQUENCE: 20

```
cattactgag ttagggttct tccnagccca acctcaaacc ctttgtttaa tttaccttgt      60
tgctttggca ggcccgcctt tcggggccgc cggggatgtt cagtcatctc tggccagtgc     120
ttgccagtag ccacttcaaa ttcttttttaa ntatgncgtc taaacaatta aatcaaaatt    180
taattaaaac tttcaacaac ggatctcttg gttctggcat cgatgaagaa cgcagcgaaa     240
tgcgataagt aatgtgaatt gcagaattca gtgaatcatc gaatctttga acgcacattg     300
cgccctttgg tattccgaag gcatgcctg ttcgagcgtc attatcaacc ctcaagcccg     360
gcttgttatt gggtcctgta tcgttaaaag ataggcccga aagataatgg cggcgtcaag    420
atagacccca ggtgcagcga gcttgctaag catacactga ggtggtcgtc ttggcctggc    480
ccaaccccaa ttttttctaag gttgacctcg gatcaggtag gaatacccgc tgaacttaag   540
catatcaatn aagcggagga aa                                             562
```

<210> SEQ ID NO 21
<211> LENGTH: 562
<212> TYPE: DNA
<213> ORGANISM: Artificial Sequence
<220> FEATURE:
<223> OTHER INFORMATION: Fungus
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (156)..(156)
<223> OTHER INFORMATION: n is a, c, g, or t
<220> FEATURE:
<221> NAME/KEY: misc_feature
<222> LOCATION: (551)..(551)
<223> OTHER INFORMATION: n is a, c, g, or t

<400> SEQUENCE: 21

```
cattactgag ttagggttct tctnagccca acctccaacc ctttgtttaa tttaccttgt      60
tgctttggca ggcccgcctt tcggggccgc cggggatgtt cagtcatctc tggccagtgc     120
ttgccagtag ccacttcaaa ttcttttttaa ctatgncgtc taaacaatta aatcaaaatt    180
taattaaaac tttcaacaac ggatctcttg gttctggcat cgatgaagaa cgcagcgaaa     240
tgcgataagt aatgtgaatt gcagaattca gtgaatcatc gaatctttga acgcacattg     300
cgccctttgg tattccgaag gcatgcctg ttcgagcgtc attatcaacc ctcaagcccg     360
gcttgttatt gggtcctgta tcgttaaaaa gataggcccg aaagataatg gcggcgtcaa    420
```

| | | |
|---|---|---|
| gatagacccc aggtgcagcg agcttgctaa gcatacactg aggtggtcgt cttggcctgg | 480 | |
| cccaacccca atttttctaa ggttgacctc ggatcaggta ggaatacccg ctgaacttaa | 540 | |
| gcatatcaat naagcggagg aa | 562 | |

<210> SEQ ID NO 22
<211> LENGTH: 562
<212> TYPE: DNA
<213> ORGANISM: Artificial Sequence
<220> FEATURE:
<223> OTHER INFORMATION: Fungus
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (551)..(551)
<223> OTHER INFORMATION: n is a, c, g, or t

<400> SEQUENCE: 22

| | |
|---|---|
| cattaccgag ntgagggccc tctgggtcca acctcccacc cgtgtttatt ttaccttgtt | 60 |
| gcttcggcgg gcccgcctta actggccgcc gggggggctta cgcccccggg cccgcgcccg | 120 |
| ccgaagacac cctcgaactc tgtctgaaga ttgtagtctg agtgaaaata taaattattt | 180 |
| aaaactttca acaacggatc tcttggttcc ggcatcgatg aagaacgcag cgaaatgcga | 240 |
| tacgtaatgt gaattgcaaa ttcagtgaat catcgagtct ttgaacgcac attgcgcccc | 300 |
| ctggtattcc gggggcatg cctgtccgag cgtcatttct gccctcaagc acggcttgtg | 360 |
| tgttgggccc cgtcctccga tcccggggga cgggcccgaa aggcagcggc ggcaccgcgt | 420 |
| ccggtcctcg agcgtatggg gctttgtcac ccgctctgta ggcccggccg gcgcttgccg | 480 |
| atcaacccaa attttatcc aggttgacct cggatcaggt agggataccc gctgaactta | 540 |
| agcatatcat naagcggagg aa | 562 |

<210> SEQ ID NO 23
<211> LENGTH: 561
<212> TYPE: DNA
<213> ORGANISM: Artificial Sequence
<220> FEATURE:
<223> OTHER INFORMATION: Fungus

<400> SEQUENCE: 23

| | |
|---|---|
| cattactgag ttagggttct tctgagccca acctccaacc ctttgtttaa tttaccttgt | 60 |
| tgctttggca ggcccgcctt cggggccgc cggggatgtt cagtcatctc tggccagtgc | 120 |
| ttgccagtag ccacttcaaa ttctttttaa ctatgtcgtc taaacaatta aatcaaaatt | 180 |
| taattaaaac tttcaacaac ggatctcttg gttctggcat cgatgaagaa cgcagcgaaa | 240 |
| tgcgataagt aatgtgaatt gcagaattca gtgaatcatc gaatctttga acgcacattg | 300 |
| cgccctttgg tattccgaag gcatgcctg ttcgagcgtc attatcaacc ctcaagcccg | 360 |
| gcttgttatt gggtcctgta tcgttaaaaa gataggcccg aaagataatg gcggcgtcaa | 420 |
| gatagacccc aggtgcagcg agcttgctaa gcatacactg aggtggtcgt cttggcctgg | 480 |
| cccaacccca atttttctaa ggttgacctc ggatcaggta ggaatacccg ctgaacttaa | 540 |
| gcatatcatt aagcggagga a | 561 |

<210> SEQ ID NO 24
<211> LENGTH: 562
<212> TYPE: DNA

<213> ORGANISM: Artificial Sequence
<220> FEATURE:
<223> OTHER INFORMATION: Fungus
<220> FEATURE:
<221> NAME/KEY: misc_feature
<222> LOCATION: (24)..(24)
<223> OTHER INFORMATION: n is a, c, g, or t

<400> SEQUENCE: 24

```
cattactgag ttagggttct tctnagccca acctccaacc ctttgtttaa tttaccttgt    60
tgctttggca ggcccgcctt tcggggccgc cggggatgtt cagtcatctc tggccagtgc   120
ttgccagtag ccacttcaaa ttcttttttaa ctatgtcgtc taaacaatta aatcaaaatt   180
taattaaaac tttcaacaac ggatctcttg gttctggcat cgatgaagaa cgcagcgaaa   240
tgcgataagt aatgtgaatt gcagaattca gtgaatcatc gaatctttga acgcacattg   300
cgccctttgg tattccgaag gcatgcctg ttcgagcgtc attatcaacc ctcaagcccg   360
gcttgttatt gggtcctgta tcgttaaaag ataggcccga agataatgg cggcgtcaag   420
atagaccccca ggtgcagcga gcttgctaag catacactga ggtggtcgtc ttggcctggc   480
ccaaccccaa ttttctaag gttgacctcg gatcaggtag gaatacccgc tgaacttaag   540
catatcatta aagcggagga aa                                           562
```

<210> SEQ ID NO 25
<211> LENGTH: 555
<212> TYPE: DNA
<213> ORGANISM: Artificial Sequence
<220> FEATURE:
<223> OTHER INFORMATION: Fungus

<400> SEQUENCE: 25

```
cattaccaga gtgccctagg ctctccaacc cattgtgaac atacctatcg ttccctcggc    60
gggctcagcg cgcggtgcct ccgggctccg ggcgtccgcc ggggacaacc aaactctgat   120
tttattgtga atctctgagg ggcgaaagcc cgaaaacaaa atgaatcaaa actttcaaca   180
acggatctct tggctctggc atcgatgaag aacgcagcga aatgcgataa gtaatgtgaa   240
ttgcagaatt cagtgaatca tcgaatcttt gaacgcacat tgcgcccgcc ggcactccgg   300
cgggcatgcc tgtccgagcg tcatttcaac cctcaggacc cccttcggg ggggacctgg   360
tgctggggat cagcggcctc cgggcccctg tcccccaaat tgagtggcgg tcgcgccgca   420
gcctcccctg cgtagtagca cacctcgcac cggagagcgg ctcggccacg ccgtgaaacc   480
cccaatttt taaggttgac ctcggatcag gtaggaatac ccgctgaact taagcatatc   540
aataaggcga aggaa                                                   555
```

<210> SEQ ID NO 26
<211> LENGTH: 508
<212> TYPE: DNA
<213> ORGANISM: Artificial Sequence
<220> FEATURE:
<223> OTHER INFORMATION: Fungus

<400> SEQUENCE: 26

```
cattaccgag tgagggcttc ggtccgacct ccaaccctga tgtgaaccaa acttgttgct    60
tcggggcga ccctgccgcc tcggcggcgc ggcgccccg aaggccatca aacactgcat   120
cattgcgtcg gagtcgaagt aaatcaaata aactttcaa caacggatct cttggttcca   180
gcatcgatga agaacgcagc gaaatgcgat aagtaatgtg aattgcagaa ttcagtgaat   240
catcgaatct ttgaacgcac attgcgccct ctggtattcc gggggggcatg cctgttcgag   300
```

```
cgtcatttca ccactcaagc ctggcttggt attgggcgtc gcggctccgc gcgcctcaaa    360
gtcttccggc tgagctgtcc gtctctacgc gttgtggcaa ctattcgcgt gggaggtcgg    420
gcggccgcgg ccgttaaacc tttcacaggt tgacctcgga tcaggtaggg atacccgctg    480
aacttaagca tatcaataag cggaggaa                                       508
```

<210> SEQ ID NO 27
<211> LENGTH: 542
<212> TYPE: DNA
<213> ORGANISM: Artificial Sequence
<220> FEATURE:
<223> OTHER INFORMATION: Fungus

<400> SEQUENCE: 27

```
cattaaaaag ttggccgggg tttcgccccg cacgcctcca tcctatgagt acttacccag     60
ttgctttggc gagccggggt gttcgcgccc cggggctctg gctgcccagc gcccgtcaga    120
ggtcaatcaa acccttgctt aacggtgaag tctgataact attatgaata gctaaaactt    180
tcaacaacgg atctcttggt tctcgcatcg atgaagaacg cagcgaaatg cgataagtaa    240
tgtgaattgc agaaatcgtg aatcatcgaa tctttgaacg cacattgcgc cctctggtat    300
tccggggggc atgcctgttc gagcgtcatt acaacctcaa gctccgcttg gtattggtgg    360
ctcgccctac ccggggcggc cccgaaaatc agcggcacag ctgcccgacc ctaagcgtag    420
taacatttct cgcgaagagg tgctcgggtg gtctgcggcc ggacaactat cacatcaatt    480
gttgacctcg gatcaggtag ggatacccgc tgaacttaag catatcataa agcgggagag    540
ga                                                                   542
```

<210> SEQ ID NO 28
<211> LENGTH: 565
<212> TYPE: DNA
<213> ORGANISM: Artificial Sequence
<220> FEATURE:
<223> OTHER INFORMATION: Fungus
<220> FEATURE:
<221> NAME/KEY: misc_feature
<222> LOCATION: (547)..(547)
<223> OTHER INFORMATION: n is a, c, g, or t
<220> FEATURE:
<221> NAME/KEY: misc_feature
<222> LOCATION: (553)..(554)
<223> OTHER INFORMATION: n is a, c, g, or t
<220> FEATURE:
<221> NAME/KEY: misc_feature
<222> LOCATION: (556)..(556)
<223> OTHER INFORMATION: n is a, c, g, or t

<400> SEQUENCE: 28

```
cattagaatg agagccggac catgctcgtg ggcgaaagcc caaacgtgcc agtaagcgcc     60
cgtaaacctc caccttgta tattattctt tgttgctttg gtgggccgca agccttcggg    120
cgagcaccgg cctcggctgg agagtgcctg ccagaggacc caactctgta atttagtgat    180
gtctgagtac tattaaatag ttaaaacttt caacaacgga tctcttggtt ctggcatcga    240
tgaagaacgc agcgaaatgc gataagtaat gtgaattgca gaattcagtg aatcatcgaa    300
tctttgaacg cacattgcgc cctctggtat tccggagggc atgcctgttc gagcgtcatt    360
ataaccaatc acgcaagtgg ttttgggggct tgcttatcta gcatcccttt aaaacagtgg    420
cggtgctata gggctctcag cgtagtaatt attccgcttt tgaaacctag acacacctgt    480
cagaaccccc aatttttta aggttgacct cggatcaggt agggataccc gctgaactta    540
agcattntaa aanncnggaa ggaaa                                          565
```

ENDOPHYTE ENHANCED SEEDLINGS WITH INCREASED PEST TOLERANCE

This application is a continuation of U.S. application Ser. No. 13/745,427 filed on Jan. 18, 2013, which is a continuation of U.S. application Ser. No. 12/447,217, filed on Dec. 18, 2009 which is a national phase entry of PCT/CA2007/001878, filed Oct. 24, 2007, which claims priority from U.S. Provisional Application Ser. No. 60/853,745 filed Oct. 24, 2006, from Canadian Application No. 2,562,175 filed Oct. 24, 2006 and from Australian Application No. 2006233180 filed Oct. 25, 2006; each of these applications being incorporated herein in their entirety by reference.

INCORPORATION OF SEQUENCE LISTING

A computer readable form of the Sequence Listing "SequenceListing_P2576US03" (27,839 bytes), amended Dec. 22, 2016, is herein incorporated by reference.

FIELD OF THE INVENTION

The invention relates to ecologically sensitive approaches to pest management. It provides a method for producing endophyte-enhanced plants with increased tolerance to pests such as herbivorous insects by inoculation with toxigenic endophyte fungi.

BACKGROUND OF THE INVENTION

The leaves of various plants including macroalgae, grasses, and sedges are known to have symptomless infections. The fungi involved are commonly referred to as endophytes. (Carroll, 1988; Clay, 1988). An endophyte is "an organism inhabiting plant organs that at some time in its life, can colonize internal plant tissue without causing apparent harm to the host" (Petrini 1991). Fungal endophytes are believed to be host specific such that they infect one or a small subset of plant species.

It is well understood that toxic metabolites produced by grass endophytes greatly reduce populations of herbivorous insects attacking the plant. This has a large affect on plant fitness (Clay, 1988; Clay & Holah, 1999). Grass seed of cultivars that contain fungal leaf endophytes has, for 10 years, been the dominant technology used for lawns and golf courses in parts of the US and Canada. These fungi produce very potent toxins inside the grass leaves that kill insects. This vastly reduces the amount of hard chemical pesticide used on the resulting lawns. Such lawns have increased drought tolerance and have increased tolerance to fungal diseases.

Conifer needles are also infected by systemic fungal endophytes that may fulfill several ecological roles (Carroll 1988; Ganley et al. 2004).

Carroll & Carroll (1978) first proposed that fungal endophytes recovered from coniferous needles might be mutualistic symbionts. They suggested decreased palatability for grazing insects and antagonism towards needle pathogens as possible benefits for the host trees. In subsequent work, this group studied the association between Douglas-fir (*Pseudotsuga menziesii*) and the needle endophyte *Rhabdocline parkeri* (Sherwood-Pike et al., 1986; Todd, 1988). An extract of *R. parkeri* was cytotoxic to HeLa cells and resulted in reduced growth rates and mortalities when incorporated into synthetic diets of *Choristoneura fumiferana* (spruce budworm) at 10 μg g$^{-1}$ (Miller, 1986).

Conifers, like other plant species, are vulnerable to pest damage. For example, the eastern spruce budworm is an economically-damaging insect pest. The last time there was an epidemic in Eastern Canada, large scale spraying of a hard chemical pesticide was undertaken. Where this was not done, the forests were devastated. For the year 1977 alone, the cost of the spraying program in New Brunswick was approximately $47 million in constant dollars. Over the intervening two decades, during a low period of the budworm cycle, the hard chemical pesticides used in the 1970's were de-registered in favour of biopesticides. Regardless, it is less likely now that the social consensus would exist for the widespread use of chemical insecticides when the spruce budworm population returns to epidemic proportions. New methods of controlling spruce budworm and other insect pests are needed.

Royama (1984) published a comprehensive analysis of the population dynamics of the spruce budworm focusing on the period 1945 to 1983 in New Brunswick (NB), Canada. One feature of this analysis is that he proposed a "fifth agent" referring to an unknown factor that was required to build models that best fit observed population changes. The central characteristic of this fifth agent was that it in some way changed the response of the insect populations to known factors such as weather, predation and disease.

From 1984-1994 isolations were made of endophytes present in needles in various species of conifers across NB. As found by workers worldwide, the needles of all mature conifers examined were colonized by several species of endophytes (Johnson & Whitney, 1989; Wilson, 1994). From collections from across NB comprising 3500 strains, a low percentage from *Abies balsamea* (balsam fir), *Picea rubens* (red spruce), *Picea glauca* (white spruce) and *Picea mariana* (black spruce) were found to produce anti-insectan toxins (Calhoun et al., 1992; Clark et al., 1989 Findlay, 1996; Findlay et al., 1994; Findlay et al., 1995 One of the toxins, rugulosin, was obtained from cultures derived from red spruce needles (Calhoun et al., 1992).

In nature, tree seedlings may acquire needle endophytes from the trees surrounding the growing tree. However, most of these strains are apparently not able to produce anti-insectan compounds. Commercially produced seedlings leaving production facilities are not colonized by needle endophytes (Miller et al., 2002). Conifers inoculated with endophytes to increase pest tolerance would be highly desirable considering the hundreds of millions of seedlings produced in North America annually.

There are difficulties in colonizing conifers with endophytes. Economically viable large-scale inoculation of conifers with desirable strains of endophytes requires a method with increased colonization efficiency and ease of inoculation.

SUMMARY OF THE INVENTION

The invention provides novel isolated toxigenic endophyte strains and provides methods for preparing a conifer seedling with increased tolerance to a pest and for inoculating a conifer seedling with an inoculum composition. The inventors have found that conifer seedlings can be colonized with a toxigenic endophyte using a method that does not require wounding. The inoculum can be applied in one embodiment, by spraying. In addition the inventors have found that inoculation efficiency is highest during a time period referred to herein as the "susceptible time window" or "receptive" time period. The invention thereby provides methods that permit increased colonization efficiency and are amenable to large-scale inoculations. The invention also includes seedlings, trees, and tree-parts (such as needles and seeds) produced according to methods of the invention.

Accordingly, the invention provides a method of preparing a conifer seedling (i.e. a colonized conifer seedling) with increased tolerance to a pest comprising inoculating a conifer seedling (i.e. a native conifer seedling) to provide increased tolerance to a pest, comprising inoculating a conifer seedling with an isolated toxigenic endophte when the conifer seedling is susceptible to colonization by the endophyte.

The inventors have identified a number of toxigenic endophytes. Accordingly, in another embodiment, the invention provides an isolated toxigenic endophyte.

The isolated toxigenic endophytes are useful for preparing conifer seedlings with increased tolerance to a pest. Accordingly, in another embodiment, the invention provides a conifer colonized by an isolated toxigenic endophyte that produces a toxin that retards pest growth.

In another embodiment, the invention provides an isolated toxigenic endophyte selected from the group consisting of 05-37A, 06-486D, 06-485A, 04-052B, 06-011B, 06-011D, 06-012C, 06-013A, 06-014C, 08-040B, 06-264A, 06-332A, 06-268A, 07-013D, 08-011D, 01-002A, 04-002G, 03-020B, 04-012A, 06-063D, 02-002C, 06-073C, 06-094E, 06-255A, 06-097D and 08-018A.

In another embodiment, the invention provides an inoculum composition for inoculating conifers to provide increased tolerance to a pest, comprising a diluent and an isolated toxigenic endophyte that produces a toxin toxic to the pest.

In another embodiment, the invention provides an antibody directed against a toxigenic endophyte selected from the group consisting of 5WS22E1, 5WS11I1, 05-37A, 06-486D, 06-485A, 04-052B, 06-011B, 06-011D, 06-012C, 06-013A, 06-014C, 08-040B, 06-264A, 06-332A, 06-268A, 07-013D, 08-011D, 01-002A, 04-002G, 03-020B, 04-012A, 06-063D, 02-002C, 06-073C, 06-094E, 06-255A, 06-097D and 08-018A.

In another embodiment, the invention provides a method of detecting the presence of a target isolated toxigenic endophyte in a conifer sample, comprising:
 a) contacting the conifer sample with an antibody directed against the endophyte;
 b) detecting the presence of bound antibody in the sample, wherein the presence of the bound antibody is indicative of the presence of the toxicgenic endophyte.

Also provided are methods of isolating toxigenic endophytes, isolated nucleic acids and kits for practicing the methods provided herein.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

Embodiments of the invention will be described in relation to the drawings in which.

Figure 1:
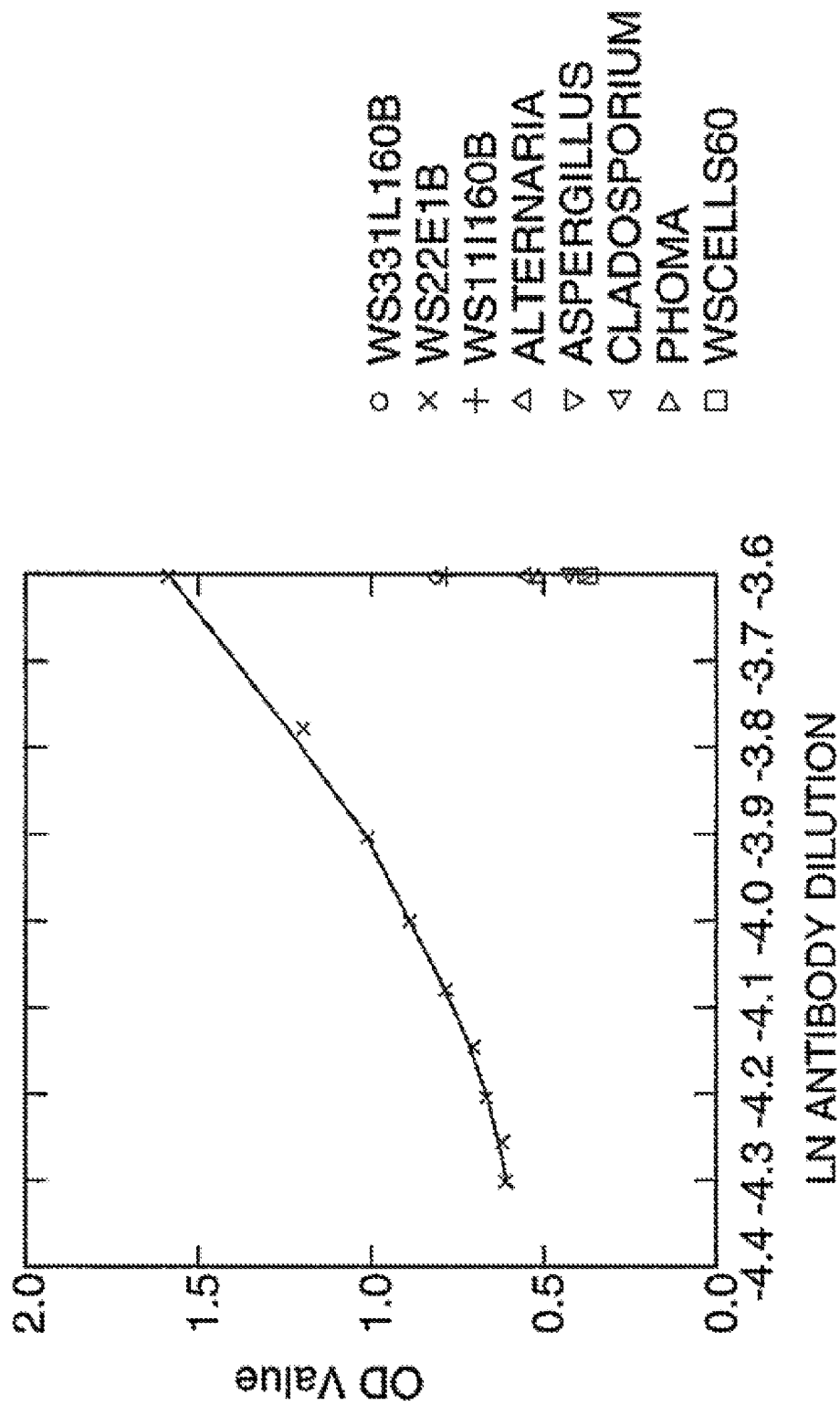
FIG. 1 shows the response of serial dilutions of polyclonal antibody to target endophyte 5WS22E1 [best fit curve using LOWESS procedure] together with comparisons at 60 ng/well of cells of some white spruce endophytes (WS331L1, WS11I1), some fungi common on the outside of the seedlings (A. altemata; A. fumigatus, C. cladosporioides, Phoma species), as well as control powdered freeze-dried white spruce needles.

Accordingly, in one embodiment, the invention provides a method of inoculating a conifer seedling, the method comprising inoculating the conifer seedling with an effective amount of an inoculum composition comprising an isolated toxigenic endophyte during a susceptible time window, wherein the susceptible time window is a period of time during which the conifer seedling is susceptible to colonization by the toxigenic endophyte.

The term "seedling" as used herein means a young plant and includes a young plant grown in a nursery production facility, prior to final planting and comprises the period of seedling development from seed to 16 weeks post-germination.

The term "colonization" as used herein means the persistence of an inoculated endophyte in a conifer plant wherein the conifer hosts the endophyte and the endophyte persists in sufficient quantity to be detected in any assay, for example, in an antibody detection assay using an antibody directed against the endophyte and/or an assay for detecting an endophyte toxin derivative or plant modified form or alternatively persists in sufficient quantity to confer pert resistance to the host. Optionally, vegetatively propagated cuttings from the colonized plant are also colonized and seedlings acquiring toxigenic endophyte by vertical transmission are also colonized.

Toxigenic Endophytes

The term "toxigenic" as used herein means toxic to a pest such as a conifer pest. "Toxigenic" includes anti-insectan and antifungal toxicity.

The term "isolated toxigenic endophyte" as used herein means an isolated endophyte strain that produces a toxin that is toxic to a pest. An isolated toxigenic endophyte is able to colonize a conifer seedling and produce a toxin in the colonized plant. The toxin produced by the toxigenic endophyte confers increased pest tolerance by controlling, reducing, mitigating, preventing or repelling a pest and/or pest growth and/or pest damage in the endophyte-colonized plant compared to a non-colonized plant.

In one embodiment, the toxigenic endophyte of the invention includes the strains described in Tables 1-3 and strains listed elsewhere herein. Other toxigenic endophytes are readily used in the methods of the invention. In addition, more than one toxigenic endophyte is optionally inoculated. The more than one toxigenic endophytes are optionally inoculated at the same time or sequentially.

The inventors have shown that various endophytes isolated from white spruce are toxigenic to conifer tree pests. These comprise rugulosin producing endophytes; vermiculin producing endophytes; mellein, including 5-methoxy-carbonylmellein, 5-formylmellein, 5-methylmellein, producing endophytes; tyrosol, including 3-butyl-4-methylfuran-2(5H)-one butyrolactone tyrosol, producing endophytes; isocoumarin, such as 8-hydroxy-6-methoxy-3-propyl-3,4-dihydroisocoumarin, producing endophytes; and 3-methyl-5,7-dimethoxyphthalide producing endophytes. These metabolites are the major components of the mixture of different anti-insectan and/or anti-fungal metabolites produced by each strain and comprises derivatives, plant modified forms and metabolites thereof that are toxic. The major metabolites their derivatives, degradation products or plant modified forms may be used as a proxy for toxicity. The fungi produce mixtures of metabolites and the toxicity of the mixture may be greater than the dominant compound used as a proxy. This may contribute to a toxigenic endophyte's ability to confer durable tolerance. The term 5-methoxy-carbonylmellein as used herein optionally comprises derivatives, plant-modified forms and metabolites thereof that are toxic to a pest.

In one embodiment, the isolated toxigenic endophyte present in the inoculum composition is a rugulosin producing endophyte. In a more specific embodiment, the rugulosin producing endophyte is isolated endophyte 5WS22E1 comprising SEQ ID NO: 1. In another embodiment the isolated toxigenic endophyte is a vermiculin producing endophyte. In a more specific embodiment, the vermiculin producing endophyte is isolated endophyte 5WS11I1 comprising SEQ ID NO: 2. In another embodiment, the isolated toxigenic endophyte is a mellein, such as 5-methoxy-carbonylmellein, producing endophyte. In a more specific embodiment, the 5-methoxy-carbonylmellein producing endophyte is the isolated 05-37A strain comprising SEQ ID NO: 3. In another embodiment, the isolated toxigenic endophyte is an isocoumarin, such as 8-hydroxy-6-methoxy-3-propyl 3,4-dihydroisocoumarin producing endophyte. In a more specific embodiment the isocoumarin compound producing endophyte is 06-485A comprising SEQ ID NO:5. In another embodiment, the isolated toxigenic endophyte is a tyrosol producing endophyte. In a more specific embodiment, the tyrosol producing endophyte is selected from the group consisting of 05-037A (SEQ ID NO:3), 06-486D (SEQ ID NO:4) and 06-485A (SEQ ID NO:5).

Isolated toxigenic endophytes are readily identified, for example, the inventors have sequenced regions of the internal transcribed spacer (ITS) regions of ribosomal DNA (rDNA). Sequence analysis revealed that strains 5WS22E1 and 5WS11I1 are *Phialocephala* species. Accordingly in another embodiment, the toxigenic endophyte strain used in methods of the invention is a toxigenic strain of the *Phialocephala* species.

In addition, the inventors have isolated several novel toxigenic endophytes from white spruce needles, including strains referred to as 05-037A, 06-486D, 06-485A, 04-052B, 06-011B, 06-011D, 06-012C, 06-013A, 06-014C, and 08-040B.

Sequence data indicates that endophyte strain 05-037A [SEQ ID NO: 3] is related to *Nemania serpens*, that strain 06-486D is related to Genbank accession AY971727 and 06-485A is related to Genbank accession AY971740, both isolated from spruce in Quebec (related to *Lophodermium* species). Both are species of *Lophodermium* (94% and 98% ITS similarity respectively) with 06-486D most similar to rhytistimataceae.

Accordingly, the invention further provides an isolated toxigenic endophyte comprising the sequence in SEQ ID NO:3 (05-037A). In another embodiment, the invention provides an isolated toxigenic endophyte comprising the sequence in SEQ ID NO: 4 (06-486D). In another embodiment, the invention provides an isolated toxigenic endophyte comprising the sequence in SEQ ID NO: 5 (06-485A). In another embodiment, the invention provides an isolated toxigenic endophyte comprising the sequence in SEQ ID NO: 6 (04-052B). In another embodiment, the invention provides an isolated toxigenic endophyte comprising the sequence in SEQ ID NO: 7 (06-011B). In another embodiment, the invention provides an isolated toxigenic endophyte comprising the sequence in SEQ ID NO: 8 (06-011D) and in another embodiment, the invention provides an isolated toxigenic endophyte comprising the sequence in SEQ ID NO: 9 (06-012C). In another embodiment, the invention provides an isolated toxigenic endophyte comprising the sequence in SEQ ID NO: 10 (06-013A). In yet another embodiment, the invention provides an isolated toxigenic endophyte comprising the sequence in SEQ ID NO: 11 (06-014C). In yet a further embodiment, embodiment, the invention provides an isolated toxigenic endophyte comprising the sequence in SEQ ID NO: 12 (08-040B).

Further the inventors have isolated multiple toxigenic endophyte strains from red spruce needles. The inventors have similarly sequenced the ITS regions of each strain (see Table 3).

Toxigenic endophytes from balsam fir have also been isolated such as 7BF 36H1 (Findlay et al, 1995).

In one embodiment, the toxigenic endophyte comprises all or part of one of SEQ ID NOS: 1-12, and preferably at least: 25-50 or 50-100 consecutive nucleotides of one of SEQ ID NO: 1-12. In another embodiment, the toxigenic endophyte comprises all or part of one of SEQ ID NOS: 13-28, and preferably at least: one of 25-50 or 50-100 consecutive nucleotides of SEQ ID NO: 13-28.

Several toxigenic endophyte strains to be used with the methods of the invention have been deposited with the Centraalbureau voor Schimmelcultures (CBS) international depository agency in the Netherlands (Accession nos. in Table 1). In addition two of the strains have been deposited with the National Mycological Herbarium/Herbier National de Mycologie recognized under the acronym DAOM as indicated in Table 1. DAOM stands for Department of Agriculture, Ottawa, Mycology.

TABLE 1

Endophyte strains, deposit accession numbers and their principal toxins where determined

| Strain | DAOM | Accession Numbers | Principal Toxin |
| --- | --- | --- | --- |
| 5WS22E1 | 229536 | CBS 120377 | rugulosin[a] |
| 5WS11I1 | 229535 | CBS 120378 | vermiculin[b,c] |
| 05-037A | | CBS 120381 | 5-methoxy-carbonylmellein[d], 5-formylmellein, 5-methylmellein, 3-butyl-4-methylfuran-2(5H)-one butyrolactone tyrosol |
| 06-486D | | CBS 120379 | Mellein, tyrosol |
| 06-485A | | CBS 120380 | 8-hydroxy-6-methoxy-3-propyl-3,4-dihydroisocoumarin, 3-methyl-5,7-dimethoxyphthalide, tyrosol |
| 04-002G | | CBS 121946 | |
| 02-002C | | CBS 121945 | |
| 06-073C | | CBS 121944 | |
| 06-255A | | CBS 121943 | |
| 06-097D | | CBS 121942 | |

[a]Calhoun, Findlay, Miller, Whitney. Mycological Research 1992, 96: 281-280. Bouhet, Van Chong, Toma, Kirszenbum, Fromageot. J Agric Food Chem 1976, 24: 964-972. Discovered in 1939 and published in 1955.
[b]Findlay, Li, Miller, Womiloju. Can J Chem, 2003, 81: 284-292.
[c]among others; a new compound trihydroxy-4-1'-hydroxyethyl) isocoumarin also toxic to spruce budworm cells (Can J Chem 81: 284)
[d]Anderson, Edwards, Whalley. J Chem Soc Perkin Trans I 1983, (2)185-255; Wang, Zhang, Huang, Su, Yang, Zhaob, Ng. Acta Cryst 2003, E59: o1233-1234

TABLE 2

Isolated White Spruce Fungal Endophytes

| SEQ ID NO. | STRAIN |
| --- | --- |
| 1 | 5WS22E1 |
| 2 | 5WS11I1 |

TABLE 2-continued

Isolated White Spruce Fungal Endophytes

| SEQ ID NO. | STRAIN |
| --- | --- |
| 3 | 05-037A |
| 4 | 06-486D |
| 5 | 06-485A |
| 6 | 04-052B |
| 7 | 06-011B |
| 8 | 06-011D |
| 9 | 06-012C |
| 10 | 06-013A |
| 11 | 06-014C |
| 12 | 08-040B |

TABLE 3

Isolated Red Spruce Fungal Endophytes

| SEQ ID NO. | STRAIN |
| --- | --- |
| 13 | 06-264A |
| 14 | 06-332A |
| 15 | 06-268A |
| 16 | 07-013D |
| 17 | 08-011D |
| 18 | 01-002A |
| 19 | 04-002G |
| 20 | 03-020B |
| 21 | 04-012A |
| 22 | 06-063D |
| 23 | 02-002C |
| 24 | 06-073C |
| 25 | 06-094E |
| 26 | 06-255A |
| 27 | 06-097D |
| 28 | 08-018A |

One skilled in the art will understand that other isolated toxigenic endophyte strains can be used with the methods and compositions of the invention. Other toxigenic endophyte strains can be isolated using the methods of screening for a toxigenic endophyte provided herein.

Endophyte Toxins

Toxigenic endophytes produce toxins that provide increased pest tolerance. The term "toxin" as used herein refers to a substance or substances that confers increased pest tolerance by controlling, reducing, mitigating, preventing or repelling pests and/or pest growth and/or pest damage. Toxins of several toxigenic endophyte strains have been identified and are described in Table 1. A particular toxigenic endophyte may produce more than one toxin. The toxins identified in Table 1 are the dominant toxins produced by the listed strains. The referenced studies to Table 1 illustrate that multiple toxins may be produced by each strain. Illustrative is strain 5WS11I1 which produces among others vermiculin, trihydroxy-4-1'-hydroxyethyl and isocoumarin.

The ability of a toxin to control, reduce, mitigate, prevent or repel pests and/or pest growth and/or pest damage can be assessed in vitro in a pest toxicity assay. For example, the inventors provide a method of assessing the toxicity of a candidate toxin using a method that assesses insect larvae growth, such as a spruce budworm larvae assay that measures effects on growth.

The term "toxicity" as used herein with respect to a pest assay such as the spruce budworm larvae assay, means toxins or endophyte strains that exhibit statistically different parameters from controls, either for weight reduction, head capsule width or both. Toxic endophytes cause pests such as spruce budworm larvae to have lower weight and/or smaller head capsule, and the aforementioned parameters are statistically reduced compared to control.

Various pest toxicity assays are provided. For example, the spruce budworm needle assay compares spruce budworm performance on foliage of different ages and tree species. The system optionally comprises a tapered container comprising a septum that permits an individual needle to be held vertically and exposed to a single spruce budworm with the base of the needle in contact with moisture. The needle is inserted in the septum before the budworm is added. The septum permits uneaten portions of the needle to be collected.

Spruce budworm larvae are typically grown with artificial diet (McMorran, 1965) until they reach a stage at which they will consume succulent needles. A single budworm is placed in each vial. Needles of similar size and weight collected around the inoculation point of the toxigenic endophyte inoculated seedling (test seedling) plus control needles are tested. Pest growth data which optionally includes the amount of unconsumed needle, head capsule width and larval weights are measured. Budworm and residual needle weights and budworm head capsule widths are determined for test and control samples and compared. Other insects and larvae may be readily tested with similar assays, for example, hemlock looper, and spruce budmoth.

The toxicity of an endophyte toxin on a pest such as hemlock looper is optionally tested according to the following method. The toxin to be tested is incorporated into an artificial diet suitable for pest growth. Artificial diet is prepared in individual cups, containing toxin concentrations of 5 micromolar, 10 micromolar, 25 micromolar, 50 micromolar and 100 micromolar. One $3^{rd}$ instar insect is added to each of 75 cups per dilution and incubated in a growth chamber under appropriate conditions such as at 22 C, 55% relative humidity with 16 h light/day. After 4 days, the insects are frozen, weighed and their head capsules measured. A reduction in head capsule size (eg. width) or weight compared to a control sample is indicative of the presence of a toxin. One skilled in the art would understand that this method can be modified to test different concentrations of toxin and that the conditions can be modified to test a variety of different pests.

The amount of toxigenic endophyte adequate to reduce growth in a conifer plant is the amount that shows a statistically-significant reduction of growth rate, and/or instar development or weight gain reduction compared to uninoculated but otherwise equivalent control seedlings. The amount will vary according to the endophyte species, the concentration of toxin and the nature of toxin produced.

In one embodiment, the assay used to evaluate pest toxicity is an in vitro assay and comprises the isolation of a conifer needle in a suitable container to ensure that the needle remains hydrated. The container is suitable to collect and evaluate the weight and head capsule width of a suitable test insect meaning an insect that normally consumes needles during its growth and development as well as collect any residual needle to assess needle consumption.

In another embodiment, the pest toxicity assay is an in vivo assay and comprises placing an appropriate insect species on branches of endophyte-colonized plants and/or trees contained in bags and/or other containers at a density of optionally not greater than 10 insects/$m^2$ of branch area, leaving the insects in place for an appropriate time period, collecting the insects followed by determinations of weight and head capsule width. Optionally other parameters may be assayed. The appropriate time period for leaving a pest in contact with the branches of an endophyte colonized plant, will vary with factors such as larval stage of development, weather conditions, conifer species and insect species. In one embodiment, the time period is optionally between 1-14 days, for example, 3-7 days.

In another embodiment, the toxicity of an endophyte is assessed by subjecting the colonized conifer plant to at least one characteristic test selected from the group consisting of a pest toxicity assay, and/or a toxin presence assay.

Accordingly the invention provides a method of assessing the pest toxicity of a toxigenic endophyte toxins using a pest toxicity assay.

Susceptible Time Window

The term "susceptible time window" as used herein means a period of time during which a conifer seedling is susceptible or receptive to colonization upon inoculation with an inoculum composition comprising a toxigenic endophyte. "Susceptible" is used interchangeably with "receptive" herein.

The term "inoculation" as used herein means providing an endophyte inoculation in a manner that permits colonization. The inoculum is optionally a laboratory prepared inoculation composition comprising a toxigenic endophyte. The inoculum can also be a colonized plant that inoculates seedlings in its vicinity through direct or vertical transmission. Vertical transmission optionally occurs through contact of uninfected seedlings with colonized infected needles including cast needles.

The inventors have established that efficient inoculation of conifer seedlings with toxigenic endophytes occurs during a susceptible time window. The susceptible time window optionally comprises the stage of seed stratification and/or the post-germination period of sustained elongation of the shoot apex wherein the cuticle is not fully formed.

Wax development occurs within the cuticle and may be referred to as cuticular wax as well as on the surface of the cuticle which may be referred to as epicuticular wax. Cuticular wax may function to provide a waterproof quality from the needle surface.

Without wishing to be bound by theory, it is believed that the upper time limit of the period during which the post-germination seedlings may be non-invasively inoculated corresponds to the formation of wax on and/or in the seedling that impairs inoculation.

The term "seed stratification" as used herein means a process of artificially or naturally interrupting a seed's embryonic dormancy so that the seed can germinate and embryonic dormancy typically comprises the period of time from taking seed from cold storage to sowing seed. "Embryonic seed dormancy" is optionally interrupted for white spruce by soaking the seed in water overnight and exposing the drained seed to temperatures of approximately 3-6° C. for approximately 2 weeks. The term "germination" as used herein means the cracking of the seed coat and growth of a seedling from a seed.

The inventors have found that seeds can be inoculated during seed stratification. In one embodiment, the method comprises soaking a conifer seed in water containing inoculum during seed stratification. In another embodiment a white spruce conifer seed is soaked in water containing inoculum overnight, drained and the still wet seed is refrigerated at 2-6° C. for approximately two weeks.

The inventors have also found that the susceptible time window comprises the period of time of sustained elongation of the shoot apex prior to formation of the needle cuticle. The susceptible time window will vary in terms of seedling height and age post germination with conifer species, but comprises the period of statistically significant maximum susceptibility, which using white spruce as a model, begins during the period of sustained elongation of the shoot apex (>10 mm<100 mm). The minimum is biologically determined by the period after the germination processes are largely completed. These include the time after the seed coat cracks and the radicle emerges. The radicle and hypocotyl and cotylyedons elongate rapidly to the point when the base of the cotyledon begins to elongate. During the period circumscribed by seedling heights>10 but >40 mm, the shoot apex, needle primordial and subtending internodes are initiated, expand and develop rapidly. The rudimentary needles and internodes become completely differentiated including formation of the cuticle and mesophyll. The critical period of successful inoculation is related to the percentage of needles of intermediate differentiation versus complete differentiation in which the cuticle is fully formed. In one embodiment a seedling is inoculated before the needle cutilcle is fully formed. In another embodiment, the seedling is inoculated during the period of sustained elongation of the shoot apex. In another embodiment, the seedling is inoculated wherein the percentage of needles wherein the cuticle is intermediately differentiation is greater than the number of needles wherein the cuticle is fully formed. A person skilled in the art would readily be able to assess these parameters.

In white spruce the inventors have determined that the susceptible time window comprises until seedlings reach 16 weeks post germination. In a preferred embodiment, seedlings are inoculated between 2-12 weeks, 6-10 weeks or 7-9 weeks post germination. In another embodiment seedlings are inoculated at 2-3 weeks, 3-4 weeks, 4-5 weeks, 5-6 weeks, 6-7 weeks, 7-8 weeks, 8-9 weeks, 9-10 weeks post-germination. It has been determined that particularly successful inoculation of white spruce seedlings is obtained in an embodiment when seedlings are inoculated at about 8 weeks post-germination (eg. 7-9 weeks post-germination).

In terms of seedling height, the period of susceptibility of white spruce comprises the germination stage up until seedlings are approximately 10 cm tall. In another embodiment the seedlings are inoculated when 1-2 cm tall, 2-3 cm tall, 3-4 cm tall, 4-5 cm tall, 5-6 cm tall, 6-7 cm tall, 7-8 cm tall, 8-9 cm tall, 9-10 cm tall. It has been determined that particularly successful inoculation is obtained in an embodiment when seedlings are inoculated at about 3 cm tall (eg 2-4 cm tall).

The period of susceptibility of spruce seedlings is as described for white spruce.

Methods of Inoculation

Various methods can be used to inoculate a conifer seedling. In embodiments of the method, inoculation of a conifer seedling comprises contacting an inoculum composition with a seedling, such as an intact seedling. An "intact seedling" as used herein refers to a seedling wherein the seedling remains unwounded prior to, or during, contact with the inoculum composition. More specifically, the stem of an intact seedling is not pierced or wounded prior to, or during, contact with the inoculum composition. An inoculum composition is optionally applied to an intact seedling by spraying the intact seedling with the inoculum composition. The use of intact seedlings is very advantageous because it eliminates the plant wounding step and facilitates rapid inoculation, providing very important time savings in a high-throughput conifer nursery setting. In another embodiment the inoculation method comprises contacting an inoculum composition with a surface area of a conifer seedling. An inoculum composition is optionally applied to a conifer seedling by spraying a surface area of a conifer seedling with the inoculum composition. The term "contacting" is used interchangeably with "applying".

The term "spraying", as used herein comprises any method of delivering liquid particles of the inoculum composition to a plant surface and includes misting, ground spraying, airblast spraying, and fan spray techniques. Spraying is optionally accomplished using a spray bottle or a boom sprayer. In one embodiment the inoculum composition is delivered using a boom sprayer and an injector pump to inject the inoculum composition into an irrigation line. Inoculation is readily applied during a time when the seedling would remain moist for the longest period of time and optionally comprises repeated application on the same or different days. In other embodiments, the inoculum composition optionally comprises additives that improve and/or increase uptake of a toxigenic endophyte. A number of chemicals and or preparations are known in the art that would facilitate inoculum uptake. For example additives may reduce the drying time after spraying. In one embodiment the additive is a carbohydrate. In another embodiment the carbohydrate is selected from the group comprising sugars. In another embodiment the carbohydrate is a carbohydrate like CMC. Further fluorescent tracers may be added to the inoculum composition to determine the amount of spray deposited.

Delivery of an inoculum composition may be performed by combining or repeating methods including spraying. Optionally the inoculum composition may be delivered by repeated spraying.

In another embodiment, the inoculation method comprises a ground application of an inoculum composition.

Inoculation of a conifer seedling, in another embodiment, comprises cutting, piercing or otherwise penetrating a seedling and delivering an inoculum composition. In one embodiment, the site of the penetration is the unlignified tissue of the seedling stem. In another embodiment, the stem is penetrated 5-15 mm from the terminal shoot. The term "terminal shoot" as used herein means the shoot distal to the lowest leaf remaining on the main stem.

In one embodiment, the method of inoculation comprises a wound inoculation. "Wound inoculation" as used herein refers to a method wherein the inoculum composition is introduced into a conifer seedling by a method involving wounding the seedling. The inoculum may be introduced by a needle injection method. In another embodiment, conifer seedlings are inoculated by placing a carrier comprising toxigenic endophytes in contact with the seedling growing medium. In one embodiment the carrier comprises irradiated conifer needles. In another embodiment, the seedling is planted in a growing medium, and irradiated conifer needles colonized by toxigenic endophytes or other conifer plant parts colonized by toxigenic endophytes are added to the growing medium. In another embodiment the growing medium, comprises potting mix surrounding or supporting the conifer seedling to be inoculated. In another embodiment the growing medium comprises soil. In particular embodiments, the conifer is wound inoculated using an inoculum composition comprising toxigenic endophyte selected from the group comprising 05-37A, 06-486D, 06-485A, 04-052B, 06-011B, 06-011D, 06-012C, 06-013A, 06-014C, 08-040B, 06-264A, 06-332A, 06-268A, 07-013D, 08-011D, 01-002A, 04-002G, 03-020B, 04-012A, 06-063D, 02-002C, 06-073C, 06-094E, 06-255A, 06-097D and 08-018A.

In addition, a conifer seedling may be inoculated by soaking a conifer seeds with an inoculum comprising a toxigenic endophyte.

The inventors have also shown that trees planted in the vicinity of infected trees (e.g. where cast would fall) are inoculated at 1 year post planting. Accordingly, in one embodiment, the invention provides a method of innoculating or transmitting an endophyte to a seedling by vertical transmission comprising placing a seedling in the vicinity of a colonized conifer. In one embodiment, the colonized conifer is colonized with a toxigenic endophyte. In another embodiment the toxigenic endophyte is selected from Table 1-3. In one embodiment, the vicinity comprises an area or zone where cast needles would fall. In one embodiment the area comprises a 0.25 metre radius around the colonized conifer. A person skilled in the art will recognize that the area where cast needles would fall depends on such factors as colonized tree size. In another embodiment, the method further comprises detecting the transmitted endophyte in the seedling. A suitable radius range in one embodiment is up to 250 cm.

In another embodiment, the inoculation method comprises putting irradiated conifer needles infested with a toxigenic endophyte in contact with a conifer seedling. The needles in one embodiment are irradiated. The needles and endophyte may be directly contacted or indirectly contacted with the conifer seedling. For examples, needles may be placed in direct physical contact with the seedling or may be placed in indirect contact with the seedling by contacting needles with the potting mix supporting seedling growth. In one embodiment the potting mix comprises soil.

The quantity of toxigenic endophyte inoculated is preferably in one embodiment approximately 10 propagules. A "propagule" as referred herein means an infective fungal cell. A person skilled in the art will recognize that the quantity of toxigenic endophyte inoculated may vary with environmental and other factors. For example, if inoculation of conifer seedlings is performed during environmental conditions such as low temperature, that are not favourable to endophyte inoculation, the quantity of toxigenic endophyte is optionally increased. Similarly, repeated inoculations are optionally used if seedlings are exposed to various environmental conditions, such as heavy rainfall where the inoculum composition is diluted or washed away.

The methods of inoculation described above can be combined and or repeated. In one embodiment the methods of inoculation combined and/or repeated comprise the same method of inoculation. In another embodiment, the methods combined and/or repeated are different methods of inoculation. For example in one embodiment, a seedling is first inoculated during seed stratification and then inoculated during the period of sustained elongation of the shoot apex.

Inoculum Composition

The inventors demonstrate that various inoculums can be used to inoculate a conifer seedling. The term "inoculum" as used herein refers to a substance comprising a toxigenic endophyte that is introduced to confer pest resistance and is optionally an inoculum composition comprising a toxigenic endophyte, for example a composition comprising a toxigenic endophyte grown in vitro, or optionally an inoculum substrate such as a conifer needle comprising a toxigenic endophyte or a carrier comprising toxigenic endophyte.

The term an "inoculum composition comprising a toxigenic endophyte" as used herein means a composition for inoculation wherein the toxigenic endophyte is present in an effective amount to colonize conifer seedlings conferring increased pest tolerance by controlling, reducing, mitigating, preventing or repelling pests and/or pest damage and/or pest growth. The inoculum composition also alternatively referred to as "inoculum" is effective if the level of toxin produced is sufficient to control, reduce, mitigate, prevent or repel pests and/or pest growth and and/or pest damage. Examples of suitable compositions are described in this application and are optionally readily identified using assays, such as spruce budworm larvae assay, described herein.

The inventors have identified novel methods to produce an inoculum composition of the invention. The filaments of the toxigenic endophyte are optionally sheared by a shearing means which reduces the number of dead endophytes produced compared to other maceration methods, thereby increasing the number of live toxigenic endophytes per volume inoculum and facilitating the colonization of inoculated conifer seedlings.

In one embodiment, the endophyte is grown in a stirred jar fermentation unit such that the cells are present in not larger than 5 mm clusters of mycelium or spores, are greater than 80% and preferably greater than 95% viable and greater than 80% and preferably greater than 95% infective in receptive tissue in liquid substantially free of bacteria and material concentrations of residual nutrients.

In another embodiment the invention provides, an inoculum composition that is optionally prepared by a method for growing the isolated endophyte comprising:

a) providing a slant culture of the endophyte (eg. agar slant culture);
b) inoculating a first liquid culture with the culture;
c) subjecting the first liquid culture to a shear force that shears the endophyte hypha;
d) inoculating a second liquid culture with the first liquid culture;
e) subjecting of the second liquid culture to a second shear force to shear the endophyte hypha.

In another embodiment, the method comprises:

a) growing an initial culture of the endophyte (eg. agar slant culture);
b) inoculating a first liquid culture with a suspension comprising the agar slant culture wherein the first liquid culture is grown for approximately 2 weeks;
c) maceration of the first liquid culture
d) inoculation of a second liquid culture with the macerated first liquid culture under conditions of shear force sufficient to shear the endophyte hypha wherein the second culture is grown in a large vessel, and is aerated.

In one embodiment, the inoculum composition is optionally harvested from the large vessel which includes a fermentor, centrifuged and resuspended in a diluent. In one embodiment the diluent is sterile water.

In one embodiment, the agar slant is a malt agar slant. In another embodiment the first liquid culture is 2% malt extract and the suspension is added at 5% v/v. The shear force in one embodiment comprises shaking or rotation at 200-310 RPM. In another optional embodiment the shaking or rotation is at 220 RPM. In one embodiment, the first liquid culture is preferably incubated at 25° C. In one embodiment the first liquid culture comprises a malt extract. In another embodiment the macerated liquid culture is added to a 1-3% malt extract broth. In one embodiment, the malt extract concentration is approximately 1%. In another embodiment, the macerated liquid culture and malt extract broth are stirred at 200-310 RPM, for example stirring at 280 RPM. In another embodiment, the temperature in the large vessel which may optionally be a stirred fermentor, is 20-22° C. and is optionally 21° C. In another embodiment, the aeration is 0.05-0.15 v/v per minute and is optionally 0.1 v/v per minute. In another embodiment, the macerated liquid culture and malt extract are incubated for 6-10 days and preferably 7 days. A person skilled in the art would understand what routine adaptations would be required to grow the new toxigenic endophyte strains identified. In addition a person skilled in the art would understand that changes to sugar concentration, temperature and oxygen tension may require compensating changes in other variables. A person skilled in the art would also understand the routine experiments to further scale up the production of inoculum composition.

The inoculum composition may be diluted or concentrated. In one embodiment, the inoculum composition is diluted with water before inoculation.

The inventors have detected rugulosin in trees, 3.5 years and 4.5 years post inoculation. The mean concentration corrected for recovery was 0.7 µg/g and this was approximately the same for different age classes of needles. In two year post inoculated trees, the inventors detected rugulosin concentrated from 0.15 µg/g to 24.8 µg/ml. The inventors have also shown that needles 15 months post inoculation showed an arithmetic mean concentration of rugulosin of 1 µg/g. These concentrations were sufficient to reduce spruce budworm growth.

The inventors have shown that the concentration of rugulosin in needles infected with rugulosin producing fungal strains that reduced pest growth averaged 1 micrograms/ gram of needle weight. A concentration that affected pest growth is optionally as low as 0.15 micrograms/gram of needle weight. Toxin or endophyte presence is deTected in a colonized conifer sample. The conifer sample comprises a conifer tissue of a plant previously inoculated with an effective inoculum concentration comprising a toxigenic endophyte. Accordingly, in one embodiment, the effective inoculum composition is a composition that produces an average rugulosin toxin concentration of at approximately 10 micromolar in a colonized conifer seedling. In another embodiment the toxin concentration achieved averages optionally 10-25 micromolar, or optionally 25-50 micromolar.

The effectiveness of the inoculum varies with the length of time the inoculum has been stored. Preferably, the inoculum is harvested, diluted and/or prepared the same day as the inoculation.

In another embodiment, the invention provides an inoculum composition comprising a toxigenic endophyte, which can be used with the methods of the invention to produce a conifer seedling infected with a toxigenic endophyte fungus.

In one embodiment, the method of inoculating conifer seedlings further comprises detecting if the seedling is colonized by the toxigenic endophyte.

Method of Detecting Toxigenic Endophyte

Various methods can be employed to detect the presence of toxigenic endophytes. Assays using antibody-based methods for the detection of grass endophytes have been developed for several endophyte species using for example microplate assays and tissue immunoblot methods (Gwinn et al. 1991; Johnson et al. 1982; Reddick & Collins 1998) Compared to competing methods such as PCR, these have a greater potential for field use based on simple protocols.

The inventors have developed an assay using a detection agent for assaying target endophytes. In one embodiment, the assay targets endophytes, such as 5WS22E1 using a detection agent that is an antibody. The antibody developed is of comparable sensitivity to antibody assays for grass endophytes (Gwinn et al. 1991; Johnson et al. 1982; Reddick & Collins 1998). This was achieved despite the greater difficulties of the conifer needle matrix compared to grass leaves. The inventors have also prepared antibodies to 5WS22E1, 5WS11I1, 05-37A, 06-486D, 06-485A.

Detection of a toxigenic endophyte can be accomplished by detecting the toxigenic endophyte strain or a product of the endophyte such as a toxin. Accordingly, the invention provides an assay using a detection agent that binds a toxin or recognizes a toxigenic strain of endophyte for detecting the presence of target endophytes in a conifer sample, the assay comprising:

a) contacting a conifer sample with an agent which recognizes a toxigenic strain of endophyte;

b) detecting the presence of bound agent in the conifer sample, wherein the presence of bound agent is indicative of the presence of the toxigenic strain of endophyte recognized by the antibody.

In one embodiment, the agent that binds a toxin or recognizes a toxigenic strain of endophyte is an antibody. Accordingly in one embodiment, the assay is an antibody assay.

In another embodiment, the antibody assay is an ELISA assay. In another embodiment, the antibody assay is a hand-held immunoblot based assay. In another embodiment, the antibody assay is contained in a kit comprising an antibody which recognizes a toxigenic strain of endophyte and a detection means to detect the presence of a strain recognized by the antibody. In another embodiment, the kit compromises an antibody which recognizes a toxigenic strain of endophyte and instructions for use.

The inventors have shown that the presence of a toxigenic strain of endophyte may not be detectable in successfully colonized seedlings until the seedling has grown for a period of time. Hence in one embodiment the conifer sample is obtained when the plant is greater than 3 months, greater than 4 months, greater than 5 months, greater than 6 months, greater than 7 months, greater than 8 months, greater than 9 months, greater than 10 months, or greater than 11 months post germination. In another embodiment, the conifer sample is obtained when the plant is greater than 1 year post germination. In another embodiment, the conifer sample is obtained when the plant is 12-18 months post germination. In another embodiment, the conifer sample is obtained when the plant age is greater than 18 months post germination.

The inventors have shown that inoculated toxigenic endophytes persist for at least five years. In addition, toxigenic endophytes spread to other branches and spread to other seedlings within the vicinity of the colonized tree. A person skilled in the art will recognize that the sample can be obtained many months or year past inoculation and can be obtained from a tissue proximal or distal to the inoculation site. For example, a person skilled in the art would recognize that branches adjacent to the site of inoculation are likely to be positive at earlier time points than branches further from the site of inoculation. Similarly, several branches can be tested when assaying a conifer for colonization. Detection of toxigenic endophyte or toxin in 9 conifer samples is sufficient to indicate the conifer is colonized.

The conifer sample optionally comprises conifer tissues including needles. The conifer sample is typically ground to a powder prior to contact with the toxigenic endophyte recognizing antibody and/or suspended in an appropriate buffer such as Tris buffered saline (TBS).

In addition, the presence of a toxigenic endophyte may be detected by analytically detecting the endophyte toxin. The inventors provide an analytical method of detecting a major toxin associated with a toxigenic strain of endophyte. The analytical method comprises preparing a candidate toxigenic endophyte toxin containing conifer sample, for processing by separation, such as HPLC (high performance liquid chromatography), the method of preparing the conifer sample optionally comprising:
a) a first extraction using petroleum ether under low light conditions;
b) a second extraction with chloroform;
c) washing the extract with NaHCO3;
d) acidifying the extract;
e) a third extraction with chloroform; drying the extract;
f) and dissolving the dried extract in acetonitrile.

The resulting sample is optionally assayed by an HPLC apparatus and the spectrum produced analysed for toxin presence. In one embodiment, the sample to be prepared for HPLC analysis comprises a rugulosin producing toxigenic endophyte.

Accordingly the invention provides a method of detecting a toxin associated with a toxigenic strain of endophyte, comprising, preparing a conifer sample for HPLC analysis separating an endophyte extract by high pressure liquid chromatography which produces a spectrum output, detecting the presence or absence of a toxin value in the spectrum output, wherein the presence of a toxin value is indicative of the presence of a toxin.

In another embodiment the method comprises:
a) separating an endophyte extract by high pressure liquid chromatography which produces a spectrum output;
b) detecting the presence or absence of a toxin value in the spectrum output, wherein the presence of a toxin value is indicative of the presence of a toxin.

The toxin is also optionally detected using other assays including NMR, preparatory thin layer chromatography, preparatory HPLC, HPLC Mass Spectroscopy and column chromatography. Methods for use of these techniques are known in the art.

Conifer Tree Species and Genotypes Susceptible to Colonization with Toxigenic Endophytes The invention is practiced with conifer plants and seedlings. A "conifer" as used herein refers to a variety of needle-leaved trees or shrubs and includes all spruce species (*Picea* species), pine (*Pinus* species) and balsam fir trees (*Abies balsamea*) and "plant" as used herein comprises a seedling or tree and includes tree hedged for the production of rooted cuttings or a shrub.

In certain embodiments, the conifer seedling inoculated is a white spruce (*Picea glauca*) seedling. In other embodiments, the conifer seedling inoculated is a red spruce (*Picea rubens*) seedling. In further embodiments, the conifer seedling inoculated is a balsam fir seedling. In yet another embodiment, the conifer seedling inoculated is a pine seedling for example white pine (*Pinus strobus*).

In one embodiment, the white spruce seedling is inoculated with an inoculum composition comprising toxigenic endophyte 5WS22E1. In another embodiment, the white spruce seedling is inoculated with an inoculum composition comprising toxigenic endophyte 5WS11I1. In another embodiment, the white spruce seedling is inoculated with an inoculum composition comprising toxigenic endophyte 05-037A (SEQ ID NO: 3). In another embodiment, the white spruce seedling is inoculated with a inoculum composition comprising toxigenic endophyte 06-486D (SEQ ID NO: 4). In another embodiment, the white spruce seedling is inoculated with an inoculum composition comprising toxigenic endophyte 06-485A (SEQ ID NO:5).

In another embodiment, the red spruce seedling is inoculated with an inoculum composition comprising a toxigenic endophyte selected from the group comprising 06-264A (SEQ ID NO:13), 06-332A (SEQ ID NO:14), 06-268A (SEQ ID NO:15), 07-013D (SEQ ID NO:16), 08-011 (SEQ ID NO:17), 01-002A (SEQ ID NO:18), 04-002G (SEQ ID NO:19), 03-020B (SEQ ID NO:20), 04-012A (SEQ ID NO:21), 06-063D (SEQ ID NO:22), 02-002C (SEQ ID NO:23), 06-073C (SEQ ID NO:24), 06-094E (SEQ ID NO:25), 06-255A (SEQ ID NO:26), 06-097D (SEQ ID NO:27) and 08-018 (SEQ ID NO:28).

The inventors found that inoculation of seedlings from a breeding population of white spruce with an inoculum composition of the invention was successful across a range of genotypes. Of the 25 white spruce families tested, six had individuals that tested positive for infestation with one of the strains of endophytes tested. Of these six families, 11 of the 31 parents were represented and these 11 parents covered the same range that the larger sample encompassed. This provided a good indication that a broad range of genotypes will be susceptible to infection by the endophytes tested.

Endophyte Enhanced Conifer Plant

A conifer plant colonized with a toxigenic endophyte strain is also provided by the invention. In one embodiment the conifer plant is a white spruce plant with toxigenic endophyte 05-037A (SEQ ID NO: 3). In another embodiment the conifer plant is a white spruce plant colonized with toxigenic endophyte 06-486D (SEQ ID NO: 4). In another embodiment the conifer plant is a white spruce plant colonized with toxigenic endophyte 06-485A (SEQ ID NO: 5).

In another embodiment, the conifer plant is a red spruce plant colonized with a toxigenic endophyte selected from the group consisting of 06-264A (SEQ ID NO:13), 06-332A (SEQ ID NO:14), 06-268A (SEQ ID NO:15), 07-013D (SEQ ID NO:16), 08-011 (SEQ ID NO:17), 01-002A (SEQ ID NO:18), 04-002G (SEQ ID NO:19), 03-020B (SEQ ID NO:20), 04-012A (SEQ ID NO:21), 06-063D (SEQ ID NO:22), 02-002C (SEQ ID NO:23), 06-073C (SEQ ID NO:24), 06-094E (SEQ ID NO:25), 06-255A (SEQ ID NO:26), 06-097D (SEQ ID NO:27) and 08-018 (SEQ ID NO:28).

Pests Susceptible to Toxigenic Endophyte Toxins The term "pest" as used herein means any organism that may cause injury to a conifer plant including any needle pathogen and comprises insects, insect larvae, and fungal pathogens. Insect pests include insects that consume needles such as spruce budworm, spruce budmoth hemlock loopers, saw flies, and jack pine budworm. Fungal pests include white pine blister rust and *fusarium* species.

All the toxins or endophyte cultures described herein have been tested with spruce budworm (*Choristoneura fumiferana*) larvae. For the 5WS22E1 toxin rugulosin, spruce budworm (FIG. 8) and hemlock loopers (*Lambdina fiscellaria*) were affected at dietary rugulosin concentrations between 25 and 50 µM. The tests with wild collected spruce budmoth (*Zeiraphera canadensis*) indicated that this species was also affected by rugulosin in the same order of magnitude Tests of fruit flies (*Drosophila melanogaster* also place the dietary toxicity of rugulosin in the 50 µM range (Dobias et al. 1980). This compound is also toxic to cultured cells of several insect cell lines including fall army worm (*Spodoptera frugiperda*) and mosquito larvae (*Aedes albopictus*; Watts et al. 2003).

When tested under the conditions described above, the semi-purified extracts of the remaining listed endophytes resulted in statistically significant reductions in spruce budworm growth rate, and/or maximum instar reached within the operating parameters of the tests.

Endophyte Screening Methods

The inventors have identified multiple strains of toxigenic endophytes that can be inoculated in conifer seedlings to reduce pest damage in colonized hosts. In identifying the toxigenic endophytes of the invention, the inventors took fungal strains from the existing literature from public collections and tested additional collections of over 1000 endophyte strains. The endophytic strains were cultured from the needles of randomly selected spruce trees and an antibody was developed to permit detection. The antibody assay permitted detection of successful inoculations. One aspect of the invention provides a method of identifying novel toxigenic endophytes that can be used with the methods and compositions of the invention.

The screening method for isolating a toxigenic endophyte from a donating plant comprises:
  a) isolating a slow growing candidate endophyte from the conifer needles of a donating plant (eg. a donating conifer);
  b) assaying the toxicity of the candidate endophyte to a pest in a pest growth toxicity assay to determine whether the candidate endophyte is a toxigenic endophyte.

If the candidate endophyte is a toxigenic endophyte, the method optionally further comprises inoculating a conifer seedling;
  a) inoculating a recipient conifer seedling with the candidate endophyte strains determined to be a toxigenic endophyte;
  b) providing a sample of the inoculated seedling and detecting the presence of the target endophyte (ie. endophyte colonization) and/or endophyte toxin.

As mentioned, the inventors have sequenced the ITS region of the identified toxigenic endophytes. Accordingly in one embodiment, the invention provides isolated nucleic acids comprising a sequence selected from the group consisting of SEQ ID NO: 3-28.

In one embodiment, the invention provides an isolated nucleic acid sequence comprising:
  (a) a nucleic acid sequence selected from the group consisting of SEQ.ID.NO.:3-28;
  (b) a nucleic acid sequence that is complimentary to a nucleic acid sequence of (a);
  (c) a nucleic acid sequence that has substantial sequence homology to a nucleic acid sequence of (a) or (b);
  (d) a nucleic acid sequence that is an analog of a nucleic acid sequence of (a), (b) or (c); or
  (e) a nucleic acid sequence that hybridizes to a nucleic acid sequence of (a), (b), (c) or (d) under stringent hybridization conditions.

The term "sequence that has substantial sequence homology" means those nucleic acid sequences which have slight or inconsequential sequence variations from the sequences in (a) or (b). The variations may be attributable to local mutations or structural modifications. Nucleic acid sequences having substantial homology include nucleic acid sequences having at least 65%, more preferably at least 85%, and most preferably 90-95% identity with the nucleic acid sequences of SEQ ID NO:3-28.

Nucleic acids comprising the sequences are useful as probes or to design probes to identify related and toxigenic endophytes. Accordingly, one embodiment provides a method of isolating a candidate toxigenic endophytye comprising contacting an an endophyte nucleic acid, such as DNA, with a probe, the probe comprising sequences corresponding to at least 50 nucleotides of sequence selected from the group comprising SEQ ID NOS 3-28, wherein endophytes with at least: 80%, 85%, 90% or 95% sequence identity are candidate toxigenic endophytes.

A candidate toxigenic endophyte is optionally further analyzed for its ability to inhibit pest growth. A candidate toxigenic endophyte that when inoculated into a seedling according to a method of the invention described herein controls, reduces, mitigates, prevents or repels pests and/or pest growth and/or pest damage is a toxigenic endophyte.

The term "probe" as used herein refers to a nucleic acid sequence that will hybridize to a nucleic acid target sequence. In one example, the probe hybridizes to DNA of a candidate toxigenic endophyte. Specifically, in one embodiment the probe hybridizes to internal transcribed spacer (ITS) sequence of ribosomal DNA of a candidate toxigenic endophyte. The length of probe depends on the hybridization conditions and the sequences of the probe and nucleic acid target sequence. In one embodiment, the probe is at least 8, 10, 15, 20, 25, 50, 75, 100, 150, 200, 250, 400 or more nucleotides in length.

The term "isolated nucleic acid sequence" as used herein refers to a nucleic acid substantially free of cellular material or culture medium when produced by recombinant DNA techniques, or chemical precursors, or other chemicals when chemically synthesized. The term "nucleic acid" is intended to include DNA and RNA and can be either double stranded or single stranded.

The term "hybridize" refers to the sequence specific non-covalent binding interaction with a complementary nucleic acid. One aspect of the invention provides an isolated nucleotide sequence, which hybridizes to a candidate toxigenic endophyte DNA. In a preferred embodiment, the hybridization is under high stringency conditions. Appropriate stringency conditions which promote hybridization are known to those skilled in the art, or can be found in Current Protocols in Molecular Biology, John Wiley & Sons, N.Y. (1989), 6.3.1 6.3.6. For example, 6.0×sodium chloride/sodium citrate (SSC) at about 45° C., followed by a wash of 2.0×SSC at 50° C. for 15 min may be employed.

The stringency may be selected based on the conditions used in the wash step. For example, the salt concentration in the wash step can be selected from a high stringency of about 0.2×SSC at 50° C. for 15 min. In addition, the temperature in the wash step can be at high stringency conditions, at about 65° C.

By "at least moderately stringent hybridization conditions" it is meant that conditions are selected which promote selective hybridization between two complementary nucleic acid molecules in solution. Hybridization may occur to all or a portion of a nucleic acid sequence molecule. The hybridizing portion is typically at least 15 (e.g. 20, 25, 30, 40 or 50) nucleotides in length. Those skilled in the art will recognize that the stability of a nucleic acid duplex, or hybrids, is determined by the Tm, which in sodium containing buffers is a function of the sodium ion concentration and temperature (Tm=81.5° C.−16.6 (Log 10 [Na+])+0.41(% (G+C)−600/l), or similar equation). Accordingly, the parameters in the wash conditions that determine hybrid stability are sodium ion concentration and temperature. In order to identify molecules that are similar, but not identical, to a known nucleic acid molecule a 1% mismatch may be assumed to result in about a 1° C. decrease in Tm, for example if nucleic acid molecules are sought that have a >95% identity, the final wash temperature will be reduced by about 5° C. Based on these considerations those skilled in the art will be able to readily select appropriate hybridization conditions. In preferred embodiments, stringent hybridization conditions are selected. By way of example the following conditions may be employed to achieve stringent hybridization: hybridization at 5×sodium chloride/sodium citrate (SSC)/5×Denhardt's solution/1.0% SDS at Tm−5° C. based on the above equation, followed by a wash of 0.2×SSC/0.1% SDS at 60° C. for 15 min. Moderately stringent hybridization conditions include a washing step in 3×SSC at 42° C. for 15 min. It is understood, however, that equivalent stringencies may be achieved using alternative buffers, salts and temperatures. Additional guidance regarding hybridization conditions may be found in: Current Protocols in Molecular Biology, John Wiley & Sons, N.Y., 1989, 6.3.1-6.3.6 and in: Sambrook et al., Molecular Cloning, a Laboratory Manual, Cold Spring Harbor Laboratory Press, 2000, Third Edition.

In another embodiment, the toxigenic endophyte toxin is sequenced and a probe is designed based on the sequence. The probe is used to identify other toxigenic endophytes producing the toxin for use with the methods of the invention. A person skilled in the art would readily be able to sequence the toxin genes or gene products and design probes based on the sequence.

The following non-limiting examples are illustrative of the present invention:

EXAMPLES

Example 1

The needles colonized by a rugulosin-producing endophyte were found to contain rugulosin in concentrations that are effective in vitro at retarding the growth of spruce budworm larvae. Larvae presented with endophyte infected needles containing rugulosin did not gain as much weight as those eating uncolonized needles. The impact on the budworm was much greater than anticipated. One strain 5WS22E1, was the most successful antagonist of larval growth. Needles of 17 of 22 seedlings colonized by rugulosin-producing strains were toxic to the insects. Needles infected by a different family of strains producing vermiculin were also toxic to the insects.

Rugulosin was unambiguously present in needles infected by rugulosin-producing strains and not found in either control or in the seedlings colonized by the vermiculin-producing endophyte. In needles that significantly affected budworm weights, rugulosin concentrations averaged 8 µg/g. This was >15 times the mean concentration found in needles that did not affect budworm growth. In vitro, rugulosin at 1 µg/g affected budworm growth and development, a value rather close to the 8 µg/g found in needles.

Example 2

Antibody Assay for Detecting Endophyte

The following describes (1) the development of a polyclonal antibody for the rugulosin-producing endophyte 5WS22E1; (2) the inoculation of 1235 seedlings and subsequent growth outdoors under commercial nursery conditions (3) analysis of these needle samples using the culture method previously employed and the antibody method and (4) HPLC analysis for the presence of rugulosin in ~10% of the positive samples.

Materials and Methods
Inoculation

The strain employed, 5WS22E1 (DAOM 229536; rugulosin producer) was described in Miller et al. (2002). Control-pollinated full-sib families of white spruce were produced for inoculation. The families used were chosen to provide a diverse set of genotypes. Nine families originating from unrelated white spruce parents were used. The parents were selected from the J.D. Irving Limited genetic improvement program and originated within a range of 45 N to 47.5 N Latitude and 65 W to 70 W Longitude in New Brunswick and Maine. The minimum distance between trees selected in the forest was 200 m. Seeds were taken from frozen storage at −5 C, planted in plastic seedling containers in a media containing 3:1 peat moss/vermiculite and placed in a greenhouse. Fertilization via irrigation water started one month after sowing (10-52-10 for two weeks followed by 8-20-30 for one week followed by 20-8-20 at 100 µg/L and increasing to a maximum of 125 µg/L).

5WS22E1 (DAOM 229536) cultures were grown on 9 cm plates containing 2% malt extract agar (Difco) at 25 C for 8 weeks. Following the incubation period, 5 mL sterile water was poured on agar surface which was then rubbed gently with a sterile bent glass rod. The resulting suspension was taken up with a sterile pipette, macerated and diluted with sterile water to deliver an average of 3 fungal hyphal fragments per drop (6 µL) from a sterile 1 mL syringe with a 0.45 mm needle (B-D #309597) as determined by counting with a hemocytometer. Wound inoculation of 1235 seedlings was performed in a laminar flow hood by injecting 6 µL into the un-lignified tissue of the stem typically 10 mm away from the terminal shoot (Miller et al. 2002). This was done at the Sussex Tree Nursery on Apr. 16, 2001. This is located at 45° 43' N, 65° 31' W; elevation 21.30 m. Mean annual temperature is 5.8 C (January −8.5, July 19.0 C) with average precipitation of 245 cm snow and 915 mm rain.

The trees were allowed to grow in trays for 6 months in a greenhouse, at which point they were planted into pots and left in a shaded area with irrigation until sampling in mid September 2002.

ELISA Development

Cells of 5WS22E1 were grown on two types of liquid media and on irradiated, young uninoculated white spruce needles. The needles were irradiated with 25kGy (MDS Nordion, Montreal, PQ) and a 200 mg sample was placed in a sterile glass Petri dish containing a filter paper followed by the addition of 1 mL sterile water. After 24 h, the culture was inoculated with a small piece of culture taken from the leading edge of a 2% malt extract agar plate. The first liquid medium used was a glucose/sucrose mineral salts medium (1 g/L $KH_2PO_4$, 1 g/L $KNO_3$, 0.5 g/L $MgSO_4.7H_2O$, 0.5 g/L KCl, 0.2 g/L glucose, 0.2 g/L sucrose) and the second, 2% malt extract. An aliquot (50 mL) of each medium was dispensed into 250 mL Erlenmeyer flasks, respectively and autoclaved. An agar culture was macerated in 100 mL sterile water under aseptic conditions. An aliquot (2.5 mL) was used to inoculate the flasks. All cultures were incubated at 18 C for ca. three months. At the end of the incubation period, the cells growing on the needles were carefully scraped off with a scalpel and freeze dried. Cells from the liquid cultures were filtered and washed several times with sterile distilled water and freeze dried.

Polyclonal antibody production was performed in goats at Cedarlane® Laboratories Limited Hornby, Ontario. Freeze-dried cells from each medium were ground up and each diluted in sterile PBS to a concentration of 20 mg/mL for the antigen solution. 0.5 mL of this solution was emulsified with 0.5 mL of complete Freund's adjuvant (Brenntag Biosector, Denmark) for the primary immunization. 0.5 mL of incomplete adjuvant was used for the subsequent boosts. A pre-immune sample was obtained from the jugular vein of each goat using a needle and vacutainer before the primary immunization. Each goat was then injected using a 21 gauge needle intramuscularly in the hind quarter at 4 different sites with 0.25 mL of the emulsified antigen solution per injection site. After 28 days the goat received its first boost as described above, its second boost at day 53 and a test bleed was taken at day 66.

The antibodies produced from the 3 different goats were tested to determine their avidity and cross reactivity with powdered, freeze-dried young uninoculated spruce needle cells, as well as cells of the most common needle phylloplane fungi isolated from these needles (*Alternaria alternata, Phoma herbarum, Cladosporium cladosporioides* and *Aspergillus fumigatus*; Miller et al. 2002; Miller et al. 1985), and other white spruce conifer endophytes: 5WS11I1 (DAOM 229535; vermiculin producer) and 5WS331L1 (a rugulosin-producer). In addition, a number of balsam fir endophytes were tested. One isolated endophyte from balsam fir is BF 36H1 (Findlay et al, 1995).

In the case of the needle endophytes, cells were produced on irradiated needles as above. The phylloplane species tested were grown in shake culture using a maltose, yeast extract, peptone medium (Miller & Mackenzie 2000), filtered, washed and freeze dried as above. This method was shown to be suitable for antigen production by such fungi in unrelated studies. Cells were ground to a fine powder in small mortar and carefully weighed. Suspensions of known concentration were made in TBS (0.8 g/L NaCl, 0.2 g/L KCl, 1.89 g/L Tris-HCl, and 1.57 g/L Tris base) in vials and vortexed.

Avidity and cross reactivity experiments were conducted on sera from the goats treated with the various immunogens in a similar fashion, first optimizing cell additions/serum dilutions, and then conducting cross-reactivity experiments. As needed, aliquots of cells were diluted in 0.1 M carbonate buffer pH 9.6 (Sigma) coating buffer to defined concentrations and pipetted into 96 well Nunc brand microplates. The plate was covered with an acetate-sealing sheet and placed on a rotary shaker for 4 h at room temperature. The plate was removed, turned upside down and shaken to remove all of the coating solution in the sink. 200 µL of Blotto (10 g of non-fat dry milk per L of TBS) was then added to each well, covered and placed in a refrigerator at 5 C overnight. The plate was then removed and washed using a Molecular Devices Skan Washer 400 to remove all of the Blotto solution. The washing solution used was TTBS (0.5 ml of tween-20/L of TBS) with a washing program of 3 cycles of soaking, washing, and rinsing. Various dilutions of goat serum in Blotto were made from which 100 µl was added to the microplate wells. The plate was covered and placed on a rotary shaker for 1 hour at room temperature, it was removed and washed using TTBS as described above. 100 µL of anti-goat IgG-horse radish peroxidase conjugate (Sigma) diluted 5000 times in Blotto was then added to each microplate well. The plate was covered and incubated at room temperature for 1 hour. The plate was washed for the final time and the substrate was added. 100 µL of TMB (Tetra-methly benzidine, Sigma) was added to each well. The plate was covered and incubated at room temperature for 30 minutes. The reaction was stopped using 50 µL of 0.5 M sulfuric acid. The plate was immediately read at 450 nm with subtraction of 630 nm on a Molecular Devices Spectra Max 340PC reader.

The polyclonal antibody produced with 5WS22E1 cells grown on the defined medium had low avidity and was not studied further. The antibody from the 2% MEA medium had acceptable avidity but unacceptable cross-reactivity. The polyclonal antibody to the cells cultured on irradiated needles was used in all further studies. A 4000 fold dilution from the latter serum with a 5000 dilution of the secondary antibody was determined to be optimal for tests with 5WS22E1 cells, allowing a preliminary estimate of the sensitivity of the assay to be made. Tests with this and the other conifer endophytes were done using cell weights from 15 to 240 ng over a 5 fold range in antibody concentration. Using a serum dilution of 4000, response to 15, 30, 60, 120 and 240 ng cells of the phyloplane species and 60, 100 and 500 ng freeze dried white spruce needles was determined. Powdered freeze-dried white spruce needles (500 ng/well) were then spiked with additions of 5WS22E1 cells over the above range.

Needle Analyses for 5WS22E1
Plating Method

At the time of sampling, average tree height was 12.9 cm. Needles from each tree were carefully removed radiating out from the inoculation point, placed in sterile plastic bags and immediately frozen for transport to the laboratory. Each bag was taken from the freezer and approximately 20 needles removed. Each needle was surfaced-disinfected by dipping in 70% ethanol for 1 min, rinsing in sterile distilled water for 1 min, and blotted dry on sterile tissue. This was placed in a sterile Petri dish and cut into 2 segments and the needle half that was attached to the stem plated on 2% malt extract agar. Plates were incubated at 18° C. for 6 weeks and were inspected regularly by microscopy for 5WS22E1 growth (Miller et al. 2002).

ELISA

The remaining needles were freeze-dried. Approximately 20 needles from each frozen needle sample were removed, ground to a fine powder in a vial using a Spex-Certiprep grinder-mixer (model 5100) and 10 mg weighted out. One mL of TBS (0.8 g/L NaCl, 0.2 g/L KCl, 1.89 g/L Tris-HCl, and 1.57 g/L Tris base) was added to each vial and placed on the vortex until completely mixed (approx. 1 min). The samples were assigned codes unrelated to the tree codes and randomized to ensure that samples from individual trees were analyzed across many plates. All were diluted in 0.1 M carbonate buffer pH 9.6 (Sigma) coating buffer to concentrations of 100 and 500 ng of needles per 100 µL well, and pipetted in duplicate onto 96 well microplate. The remaining steps in the analysis were as described above. In each trial, 60 ng of 5WS22E1 cells were used as a positive control to assess the performance of the assay; relative standard deviation of the net value of 25 representative experiments was 8.7%. Unless an acceptable positive control result was obtained, the results from individual plates were re-done. Samples with high absorbance values in both 100 ng and 500 ng tests were rejected as indicating dilution problems. Results were scored as positive when absorbance of the 500 ng sample was greater than the lowest absorbance value above one (1.000) plus the mean absorbance value of 30 ng of the target endophyte on that plate.

Chemical Analyses

Rugulosin of purity>95% was used for standards. The presence of rugulosin was then to be determined in a sub-sample of 113 randomly-selected trees of the 330 trees determined to be endophyte positive by antibody. A 100 mg sample of freeze-dried needles was ground to a fine power as describe above and extracted with 10 mL of ice cold petroleum ether by stirring for 45 min under conditions of low light. The flask was kept on ice during the extracting and was covered with aluminium foil to prevent degradation by light. The suspension was filtered by suction and discarded. The needles were returned to the flask and extracted with 10 mL of chloroform for 45 min as above for petroleum ether. The new suspension was then filtered by suction and retained while the needles were discarded. The chloroform extract was washed with 10 mL of 5% $NaHCO_3$ in a separatory funnel. This first chloroform layer was then discarded, the pH was acidified to pH 3 using 1 N HCl, and a new 10 mL of chloroform was added to the separatory funnel and extracted. The chloroform was removed and dried in an amber vial under a gentle stream of nitrogen.

The dried extracts were re-dissolved in 50 µL of acetonitrile, 10 µL was removed and injected into an 1100 series Agilent Technologies HPLC-DAD, using a Synergi Max RP 80A, 250×4.6 column (Phenomonex) and a gradient method adapted from Frisvad (1987). The gradient started at 90% water with 0.05% TFA and 10% acetonitrile and changed to 10% water with 0.05% TFA and 90% acetonitrile over the 20 min run. Samples were analysed at 389 nm, the maximum UVNIS absorption for rugulosin and peak identity was confirmed by full spectrum data from the diode array detector. The limit of quantification was 150 ng/g freeze dried powdered material; recoveries from spiked needles averaged 75%.

Statistical analyses were done using SYSTAT v. 10.2 (Point Richmond, Calif.).

Results

Inoculation and ELISA Development

Under the conditions described, the limit of quantification for the target endophyte 5WS22E1 was between 30 and 60 ng cells per well; the limit of detection was 30 ng. Over a concentration range of one log, the antibody demonstrated a linear response to 60 ng of target endophyte (FIG. 1; results of triplicate experiments presented). Relative cross-reactivity to 15, 30, 60, 120 and 240 ng cells of the phyloplane species was moderate (8%). Over the same range, there was slightly greater cross-reactivity to the cells of the two white spruce endophytes tested (~15%), one of which produced rugulosin. Even at 240 ng cells, the response was below the 1 absorbance unit threshold used. The response of the polyclonal to the above range of the non-target fungal cells was not linear across a range of antibody concentrations. The response to 60, 100 and 500 ng of white spruce cells again across a range of antibody concentrations was moderate (~6%) and also non-linear. A comparison of the response to 60 ng of non-target cells to the target endophyte is given in FIG. 1; average relative standard deviation of replicates included in these data was 6.3%.

Quantification of the target endophyte was not affected by the presence of larger amounts of powdered freeze dried needles (~2-18 x). By ANOVA with Fishers LSD test, the response for 500 ng needle material plus 30 ng target endophyte was significantly greater than that for the 15 ng combination ($p=0.008$). The value for 30 and 60 ng were not significantly different ($p=0.312$) indicating that the limit of quantification was between these values in the presence of needle material. All remaining p values between endophyte needle cell additions were >0.003. Absorbance values for 30, 60, 120 and 240 ng target endophyte plus needle material and the fungus alone were highly correlated $r=0.951$ ($p>0.000$) indicating that the presence of the needle did not affect the linearity of the assay (FIG. 2; results of triplicate experiments presented).

Needle and Chemical Analyses

Of the 1235 trees tested, only 40 were clearly positive for 5WS22E1 by plating analysis, i.e. the fungus grew from the cut end of >15/20 of the needles. The majority of the ca. 25,000 surface-disinfested needle segments exhibited the growth of non-endophyte fungi comprising those previously observed (Miller et al. 2002). As before, the colonies of these taxa typically arose from the sides of the needles rather than the cut ends.

Figure 3:
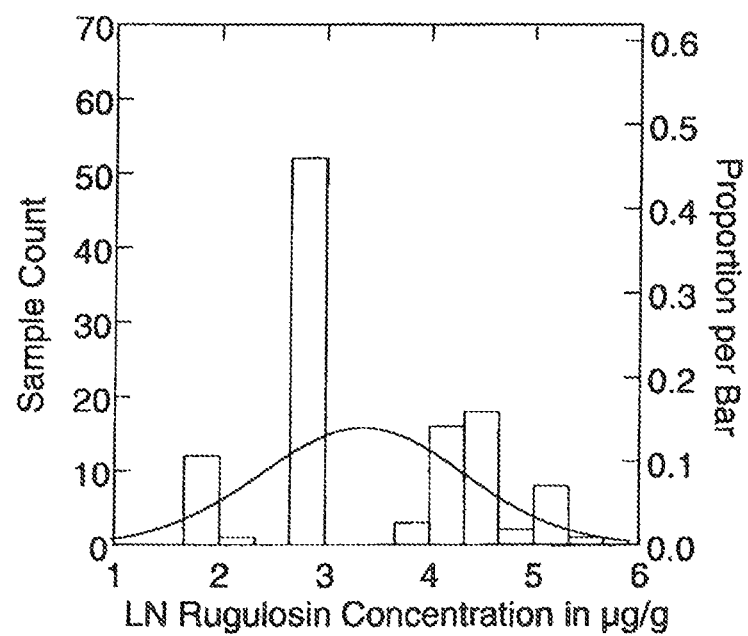
FIG. 3 shows the distribution of rugulosin concentrations in needles from 113 seedlings, assuming half the detection limit for the non-detects [with normal smoother].

When the same samples were analyzed by the antibody method, 330 or 27% were positive. All of the samples where the fungus was seen in culture were positive by the antibody assay. Of the 113 samples tested for rugulosin by HPLC from the 330 antibody positive needles, 101 (90%) were positive at the limit of quantification. The range of concentrations found was 0.15 to 24.8 µg/g needle. The distribution of values (assuming half the detection limit for the non-detects) is shown on FIG. 3). The Geometric Mean needle rugulosin concentration was 1.02 µg/g.

Mean frozen weight of 100 representative needles was 2.6 mg/needle. The freeze-dried weight was 1.08 mg/needle.

Figure 2:
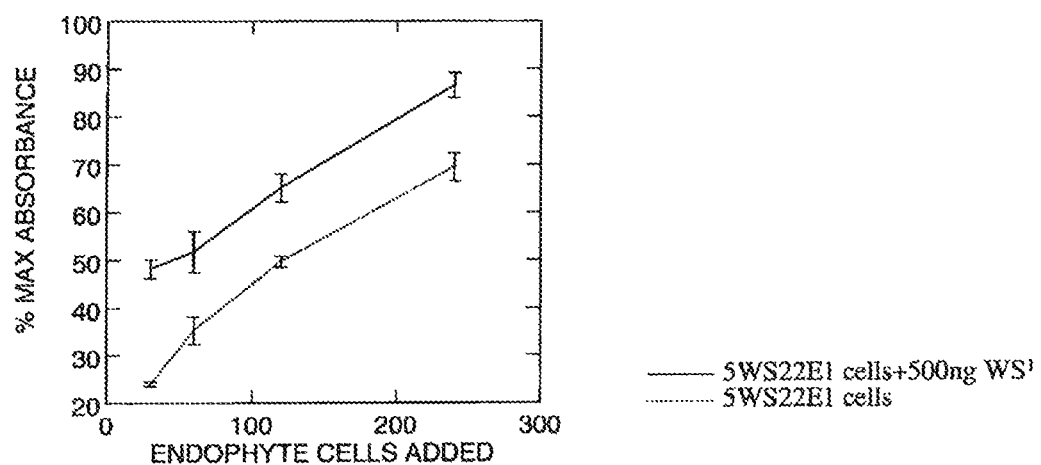
FIG. 2 shows the response of a polyclonal antibody to 30, 60, 120 and 240 ng 5WS22E1 cells and to the same amounts added to 500 ng powdered white spruce cells [mean plus standard error].

The polyclonal assay developed for the target endophyte 5WS22E1 was of comparable sensitivity to similar assays for grass endophytes (Gwinn et al. 1991; Johnson et al. 1982; Reddick & Collins 1998. This was achieved despite the greater difficulties of the conifer needle matrix compared to grass leaves. Cuttings of the latter can be placed directly in microplates whereas the tough, hydrophobic conifer needles must be ground to expose the fungal cells to the antibody. Cross-reactivity to the potentially competing fungi was acceptable (FIG. 1). Epiphytic biomass is typically low in young needles (Carroll 1979) and is comprised mostly of fungi (Swisher & Carroll 1980). Based on an extrapolation of our data on their data (Swisher & Carroll 1980; their Table 2), the fungal epiphytic biomass on these 19 month old needles would have <3 µg/g. This means the presence of such fungi in our needle samples had no effect on the antibody response in these assays. Additionally, relatively large amounts of powdered white spruce needles compared to fungal cells did not affect the reliable detection of 30-60 ng cells of target endophyte (FIG. 2).

Most (90%) of the needles shown to be endophyte positive by the antibody method contained rugulosin concentrations above the detection limit. This provides additional evidence of the reliability of the antibody method. The mean (1 µg/g), range and distribution of rugulosin concentrations in these needles (FIG. 3) were similar to that found in growth chamber-grown seedlings (Miller et al. 2002). The analytical method used in the present study included examination of the full scan UV spectrum of the rugulosin peak. This provides additional confirmation of the presence of this compound compared to the previous HPLC UV and TLC analyses (Miller et al. 2002).

The analyses were done using replicate 500 ng sub-samples obtained from a 20 needle sample. The conservative assumption used in the scoring of the 330 positive seedlings was that they contained the limit of quantification. Using this conservative assumption, each needle would contain 60 µg endophyte biomass per g needle or ~6%. For comparison, Swisher and Carroll (1980) report that 1-4 year old Douglas fir needles have ~10 µg epiphyte biomass per g needle. This was mainly comprised of fungi but including algae and bacteria in older needles. This measurement enables another comparison to be made: the amount of rugulosin per weight of fungal cells.

Several studies have been made of the production of mycotoxins in living plants using culture and ergosterol to assess fungal biomass. A representative example is a study of deoxynivalenol in experimentally-inoculated corn pre-harvest with corresponding measurements of ergosterol and viable fungi among other data (Miller et al. 1983). Using the ergosterol-fungal biomass conversion discussed in Gessner & Newell (2002), it is possible to estimate that in planta dexoynivalenol concentration corresponded to ~3% of the fungal biomass. Using the mean rugulosin concentration, the ratio in this case was ~2%.

In summary, the polyclonal assay developed for the target endophyte 5WS22E1 reliably detected the fungus in 500 ng sub-samples of colonized needles. Nineteen months post-inoculation, rates of colonization detected were high. Analysis showed most colonized needles (90%) contained detectable concentrations of the 5WS22E1 anti-insectan compound rugulosin.

Example 3

Fungal Collections

From ca. 12 sites in New Brunswick, Nova Scotia, Quebec and Maine, branches were collected from superior trees of white spruce, red spruce and balsam fir in various stands, primarily in relatively undisturbed natural forest stands but also in 20-30 year old plantations. This was done from 1985-2005. Branches were collected either directly in the field or from branches of trees which had been grafted from field selections and grown in a clone bank plantation in Sussex, New Brunswick. From the branches, needles were surface sterilized and plated to general procedures developed by Carroll and colleagues (e.g. Carroll and Carroll, 1978). Briefly, typically 20 healthy needles were harvested from each branch. These were surface sterilized by immersion in 70% ethanol, followed by 6% sodium hypochlorite for 10 min followed by rinsing in sterile de-ionized water, blotted dry on sterile tissue and plated on 2% malt extract agar. Plates were incubated at 18° C. for ~6 weeks. The purpose of this surface disinfection was to eliminate phylloplane fungi that obscure the slow-growing needle endophytes (Carroll and Carroll, 1978; Clark et al, 1989). All needle segments were inspected with a stereo microscope. Colonies not obviously *Cladosporium* or *Alternaria* were examined under high power for endophyte diagnosis.

Slow growing cultures were transferred to 2% malt agar slants or culture bottles, incubated at 16-18° C., sealed, inventoried for culture appearance and collection details and stored at 5° C. The several thousand strains that were collected, were sorted by location, site and colony morphology and a random selection taken out for further study.

Screening Fungal Collection for Anti-pathogen (Eg Anti-insectan) Toxins

Selected isolates were grown either in Glaxo bottles or other vessels that allow cultures with a large surface area to volume ratio with lower oxygen tension. The medium used was 2% malt extract in de-ionized water. Cultures were inoculated by macerating the 2% malt extract agar slant in sterile de-ionized water under asceptic conditions and adding the resulting suspension 5% v/v either directly for smaller culture vessels (Clark et al, 1989) or into 250 mL Erlemeyer flasks containing 2% malt in de-ionized water for 2 weeks at 25° C. This in turn was macerated and inoculated into Glaxo and Roux bottles and incubated for 6-8 weeks at 16-18° C.

The resulting cultures were filtered. The mycelium were frozen and freeze dried. The culture filtrates were extracted with ethyl acetate and examined for evidence of metabolite production by thin layer chromatography, NMR and High Performance Liquid Chromatography with double diode array detector. Based on this evidence, the extracts were screened for dietary toxicity to spruce budworm larvae. The principal anti-insectan toxins were thus isolated and identified using standard methods of organic chemistry including, but not limited to preparative TLC, column chromatography, NMR and high resolution mass spectroscopy.

Identification of Strains

Figure 8:
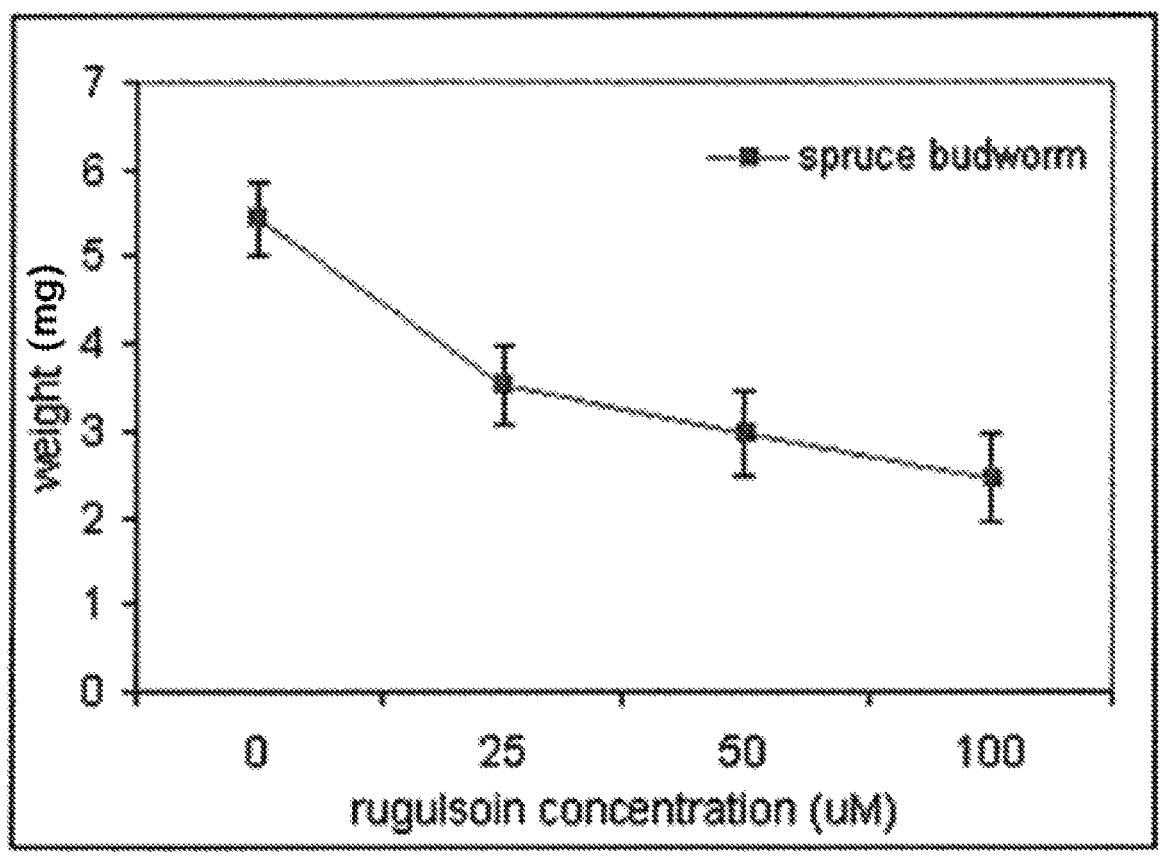
FIG. 8 plots the average weight of spruce budworm grown on diet with increasing rugulosin concentration.

Colony morphological information for 5WS22E1 and SWS11I1 the two well studied strains is as follows: Strains were grown on 2% malt agar at 25° C. in the dark. 5WS22E1 grew at 0.5 mm $day^{-1}$. The mycelia were mainly submerged, the colony was reddish-brown with a reddish soluble pigment; reverse was brown becoming red-brown in age. The mycelia were dark brown with roughened thick walls 1-2 μm in diameter, sepate, with occasional branches arising at right angles from the mycelia. 5WS11I1 grew at 0.4 mm $day^{-1}$. The colony and reverse were olive-brown with no soluble pigment and the mycelia were both submerged and aerial. The mycelia were olive brown with roughened walls 1-2 μm in diameter, sepate, with no branching (Miller et al, 2002).

Molecular characterization of the five strains of interest has been done using the primers of Glass & Donaldson (1995) which are the recognized standard approach for filamentous Ascomycetes at present. Cells of the endophytes were grown in liquid culture, filtered and washed and then the DNA was extracted using the Ultraclean microbial DNA isolation kit (Mo Bio Laboratories, #12224-250) and the resulting sequences examined in public databases for related sequences. None of the strains have previously been deposited in GenBank®. Based on sequence similarity, strains 5WS22E1 and 5WS11I1 are provisionally species of *Phialocephala* which includes species that are endophytic on spruce. Strain 05-037A was isolated from the needles of *P. glauca* in St. George, NB. Limited DNA sequences were available for related fungi, but the available data shows that it is in the order Xylariales, family Xylariaceae and close to but not identical to Hypoxylon/*Nemania serpens* (98% ITS sequence similarity) (Vasiliauskas, 2005, Sanchez-Ballesteros, 2000). The other white spruce strains, 06-486D and 06-485A, were isolated from needles in Sussex, NB. The sequencing data shows that they are most closely related to unidentified fungal species isolated from black spruce trees in Quebec, Canada. Both are species of *Lophodermium* (94% and 98% ITS similarity respectively) with 06-486D most similar to Rhytistimataceae (Higgins et al, 2007, Ganley & Newcombe, 2006).

Identification of Effective Strains

Effective strains are those that (a) produce anti-insectan compounds toxic to the spruce budworms in vitro, (b) colonize white spruce seedlings, (c) produce their toxin(s) in planta (d) insects consuming endophyte-colonized needles show reduced growth rates.

a) Insect Tests are Done by Adding Pure Compound to Synthetic Diet.

Spruce budworm (*Choristoneura fumiferana*) larvae were obtained from the colony at the Natural Resources Canada, Canadian Forest Service Laboratory in Sault Ste. Marie, Ontario and stored at 5° C. For each test, second instar larvae are put in creamer cups containing approximately 15 ml of artificial diet which had been prepared the day before and allowed to set overnight. The diet used is based on McMorran (1965) as modified by Forestry Canada. The cups are placed in a growth chamber at 22° C., 55% RH with 16 h light/day until they reach 4-5 instar as estimated by visually assessment. Batches of diet are prepared and suitable portions were measured out for addition of extracts, fractions or pure compounds. After 4 days on the test diet, the budworms were frozen, weighed and measured. The data was analyzed for dry weight reductions in comparison to controls and for changes in the distribution of insects at different instars in comparison to controls.

For spruce budworm, a preliminary test indicated that the effective approximate concentration of rugulosin for growth limitation was 10 μM (Calhoun et al. 1992). Additional tests produced a similar value of 25 µM rugulosin with an associated p value of 0.027 µM for weight reduction (see FIG. 8).

Strains 5WS22E1, 5WS11I1, 05-037A, 06-486D, 06-485A are active in similar in vitro tests of extracts.

(b) Colonization of White Spruce Seedlings

Colonization of seedlings after experimental inoculation has been done for 5WS22E1 and assessed by presence by colony morphology, a positive antibody test and analysis of toxin in planta (Miller et al, 2002, Sumarah et al, 2005). The persistence of colonization producing effective concentrations of rugulosin in the field for ≥5 years of 5WS22E1 has been demonstrated.

ELISA Assays

Antibody production was done using cells of 5WS22E1 grown on irradiated, young uninoculated white spruce needles. The needles were irradiated with 25kGy (MDS Nordion, Montreal, PQ) and 200 mg was placed in a sterile glass Petri dish containing a filter paper followed by the addition of 1 mL sterile water. After 24 h, the culture was inoculated with a small piece of culture taken from the leading edge of a 2% malt extract agar plate. At the end of the incubation period, the cells growing on the needles were carefully scraped off with a scalpel and freeze dried.

Polyclonal antibody production was performed in goats at Cedarlane® Laboratories Limited, Hornby, Ontario. This laboratory meets the requirements of the Canadian Council on Animal Care. Freeze-dried cells from each medium were ground up and each diluted in sterile PBS to a concentration of 20 mg/mL for the antigen solution. 0.5 mL of this solution was emulsified with 0.5 mL of complete Freund's adjuvant (Brenntag Biosector, Denmark) for the primary immunization. 0.5 mL of incomplete adjuvant was used for the subsequent boosts. A pre-immune sample was obtained from the jugular vein of each goat using a needle and vacutainer before the primary immunization. Each goat was then injected using a 21 gauge needle intramuscularly in the hind quarter at 4 different sites with 0.25 mL of the emulsified antigen solution per injection site. After 28 days the goat received its first boost as described above, its second boost at day 53 and a test bleed was taken at day 66.

The antibodies produced from the 3 different goats were tested to determine their avidity and cross reactivity with powdered, freeze-dried young uninoculated spruce needle cells, as well as cells of the most common needle phylloplane fungi isolated from these needles (*Alternaria alternata, Phoma herbarum, Cladosporium cladosporioides* and *Aspergillus fumigatus*), and other white spruce conifer endophytes: 5WS11I1 (DAOM 229535; vermiculin producer) and 5WS331L1 (a rugulosin-producer). In addition, a number of balsam fir endophytes were tested. In the case of the needle endophytes, cells were produced on irradiated needles as above. The phylloplane species tested were grown in shake culture using a maltose, yeast extract, peptone medium, filtered, washed and freeze dried as above. This method was shown to be suitable for antigen production by such fungi in unrelated studies. Cells were ground to a fine powder in small mortar and carefully weighed. Suspensions of known concentration were made in TBS (0.8 g/L NaCl, 0.2 g/L KCl, 1.89 g/L Tris-HCl, and 1.57 g/L Tris base) in vials and vortexed.

Avidity and cross reactivity experiments were conducted on sera from the goats treated with the various immunogens in a similar fashion, first optimizing cell additions/serum dilutions, and then conducting cross-reactivity experiments. As needed, aliquots of cells were diluted in 0.1 M carbonate buffer pH 9.6 (Sigma) coating buffer to defined concentrations and pipetted into 96 well Nunc brand microplates. The plate was covered with an acetate-sealing sheet and placed on a rotary shaker for 4 h at room temperature. The plate was removed, turned upside down and shaken to remove all of the coating solution in the sink. 200 µL of Blotto (10 g of non-fat dry milk per L of TBS) was then added to each well, covered and placed in a refrigerator at 5 C overnight. The plate was then removed and washed using a Molecular Devices Skan Washer 400 to remove all of the Blotto solution. The washing solution used was TTBS (0.5 ml of tween-20/L of TBS) with a washing program of 3 cycles of soaking, washing, and rinsing. Various dilutions of goat serum in Blotto were made from which 100 µl was added to the microplate wells. The plate was covered and placed on a rotary shaker for 1 hour at room temperature, and then removed and washed using TTBS as described above. 100 µL of anti-goat IgG-horse radish peroxidase conjugate (Sigma) diluted 5000 times in Blotto was then added to each microplate well. The plate was covered and incubated at room temperature for 1 hour. The plate was washed for the final time and the substrate was added. 100 µL of TMB (Tetra-methyl benzidine, Sigma) was added to each well. The plate was covered and incubated at room temperature for 30 minutes. The reaction was stopped using 50 µL of 0.5 M sulfuric acid. The plate was immediately read at 450 nm with subtraction of 630 nm on a Molecular Devices Spectra Max 340PC reader.

The polyclonal antibody produced with 5WS22E1 cells grown on the defined medium had low avidity and was not studied further. The antibody from the 2% MEA medium had acceptable avidity but unacceptable cross-reactivity. The polyclonal antibody to the cells cultured on irradiated needles was used in all further studies. A 4000 fold dilution from the latter serum with a 5000 dilution of the secondary antibody was determined to be optimal for tests with 5WS22E1 cells, allowing a preliminary estimate of the sensitivity of the assay to be made. Tests with this and the other conifer endophytes were done using cell weights from 15 to 240 ng over a 5 fold range in antibody concentration. Using a serum dilution of 4000, response to 15, 30, 60, 120 and 240 ng cells of the phyloplane species and 60, 100 and 500 ng freeze dried white spruce needles was determined. Powdered freeze-dried white spruce needles (500 ng/well) were then spiked with additions of 5WS22E1 cells over the above range.

(c) Produce their Toxin(s) in Plants

Rugulosin Analysis

Typically, a 100 mg sample of freeze-dried needles was ground to a fine power as describe above and extracted with 10 mL of ice cold petroleum ether by stirring for 45 min under conditions of low light. The flask was kept on ice during the extracting and was covered with aluminum foil to prevent degradation by light. The suspension was filtered by suction and discarded. The needles were returned to the flask and extracted with 10 mL of chloroform for 45 min as above for petroleum ether. The new suspension was then filtered by suction and retained while the needles were discarded. The chloroform extract was washed with 10 mL of 5% NaHCO₃ in a separatory funnel. This first chloroform layer was then discarded, the pH was acidified to pH 3 using 1 N HCl, and a new 10 mL dilquot of chloroform was added to the separatory funnel and extracted. The chloroform was removed and dried in an amber vial under a gentle stream of nitrogen.

Figure 7:
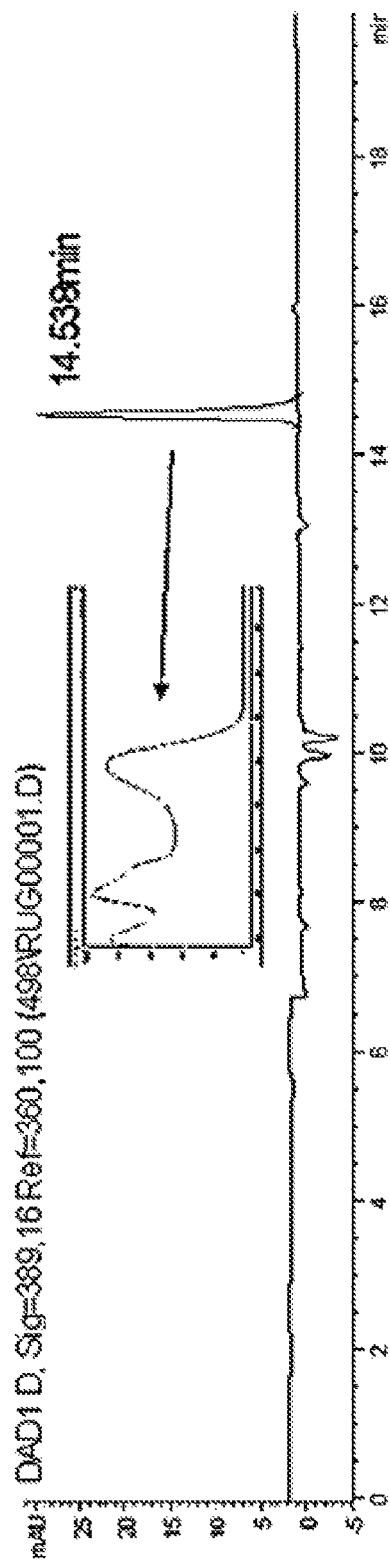
FIG. 7 shows an HPLC trace for rugulosin.

The dried extracts were re-dissolved in 50 µL of acetonitrile and 10 µL was removed and injected into an 1100 series Agilent Technologies HPLC-DAD, using a Synergi Max RP 80A, 250×4.6 column (Phenomonex) and a gradient method adapted from Frisvad (1987). The gradient started at 90% water with 0.05% TFA and 10% acetonitrile and changed to 10% water with 0.05% TFA and 90% acetonitrile over the 20 min run. Samples were analysed at 389 nm, the maximum UV/VIS absorption for rugulosin and peak identity was confirmed by full spectrum data from the diode array detector (FIG. 7). The limit of quantification was 150 ng/g freeze dried powdered material; recoveries from spiked needles averaged 75%.

Vermiculin Analysis

Colonization by 5WS11I1 after experimental inoculation was demonstrated by colony morphology (Miller et al, 2002) by a positive antibody test and by the presence of the toxin in planta. Antibody development was done the same way as above.

The principal 5WS11I1 toxin, vermiculin, was determined as follows. Ten milliliters of ice-cold petroleum ether was added to each sample of ground needles and left to extract for 45 mins to an hour on ice while agitated on a magnetic stir plate. The solutions were then filtered with Whatman #1 filter paper and a Buchner funnel. Ten milliliters of ethyl acetate was added to the needles and filter paper. The solutions were left to extract for 45 minutes to an hour while agitated on a magnetic stir plate and again filtered through Whatman #1 filter paper on a Buchner funnel. The filtrate was collected and dried under a gentle stream of nitrogen. Approximately one milliliter of acetonitrile was added to the dried extracts and the subsequent solution was vortexed, filtered through a 0.22 µm or 0.45 µm Acrodisk filter, redried under nitrogen and redissolved in a small amount (100-300 µl) of acetonitrile. These extracts were then injected on the HPLC. The vermiculin peak was detected in the UV chromatogram at 224 nm, its UV max in the full scan spectrum.

Tests for the isolated vermiculin producing endophyte were described in Miller et al., 2002).

(d) Insects Consuming Endophyte-colonized Needles Show Reduced Growth Rates

The test system used to assess 5WS22E1 and 5WS11I1 (Miller et al, 2002) was adapted from that of Thomas (1983) to compare spruce budworm performance on foliage of different ages and tree species. The system comprised of 4 ml tapered plastic sample cups with caps each drilled through the center with a 0.5 mm hole and a piece of Oasis™ foam cut to the size of the narrow base of the vials (10 mm diameter×15 mm). Just before use, 0.5 ml sterile water was added. This permitted individual needles to be held vertically and exposed to a single spruce budworm with the base of the needle in contact with moisture. The needle was taken out of the freezer and inserted in the septum just before the budworm was added. The smooth surface of the septum allowed uneaten portions of the needle to be collected. The vials were held upright in groups of 30 in wood holders.

Second instar spruce budworm were were placed in vials containing artificial diet (McMorran, 1965). They were held in growth chambers at 22° C., 55% RH with 16 h light/day for 1-2 days until they reached a head capsule width of 0.4±0.1 mm ($3^{rd}$ instar). This is a stage at which they will consume succulent needles. Batches of 60-70 larvae were combined and gently mixed by hand to randomize the animals from their original growth vial. A single budworm was then placed in each vial. From a well mixed pool of frozen needles, 100 of a similar size and weight, collected around the inoculation point of the test seedling plus 100 control needles per genotype were tested. Typically 600 insects were tested at a time. One control plant genotype was tested 4 times. Each vial was labeled so as not to be indicative of the origin of the needle. Vials were placed in a controlled environment chamber (22° C., 55% RH, 16 h day) for 48 h at which time the wood holders were placed in a freezer. The amount of unconsumed needle, head capsule width and larval frozen weights were measured. Budworm and residual needle weights and budworm head capsule widths were determined.

Tests have been done for tree endophyte 5WS22E1 in both 2 and 3 year old trees on the growth of diet raised disease-free second instar spruce budworm larvae as follows: A set number of budworm were placed by hand on lateral branches with buds and then covered with a mesh screen on both endophyte-positive and negative trees. Temperature recorders were placed in the holding area and the progress monitored until the budworm was not greater than sixth instar. At termination, the insects were collected, frozen for subsequent determinations of head capsule width and frozen weight. Samples were collected for toxin analysis to ensure that there was no misclassification of the trees as to their endophyte status. The weight of the budworm on the infected trees was significantly reduced compared to those on the control trees.

Example 4

Detection of Endophyte 5WS11I1

The polyclonal antibody used for detection of endophyte 5WS11I1 was prepared as described above for 5WS22E1.

Under the analysis conditions described above, the limit of quantification and limit of detection for the target endophyte 5WS11I1 were both 30 ng cells per well. Over a concentration range of one log, the antibody demonstrated a linear response to 60 ng of target endophyte (FIG. 1; results of triplicate experiments presented). Relative cross-reactivity to 15, 30, 60, 120 and 240 ng cells of the phyloplane species was moderate (>10%). Over the same range, there was slightly greater cross-reactivity to the cells of the two white spruce endophytes tested (~5%). Even at 240 ng cells, the response was ≥ the 1 absorbance unit threshold used. The response of the polyclonal to the above range of the non-target fungal cells was not linear across a range of antibody concentrations. The response to 60, 100 and 500 ng of white spruce cells again across a range of antibody concentrations was modest (>10%) and also non-linear. A comparison of the response to 60 ng of non-target cells to the target endophyte is given in FIG. 1; average relative standard deviation of replicates included in these data was 6%.

Figure 4:
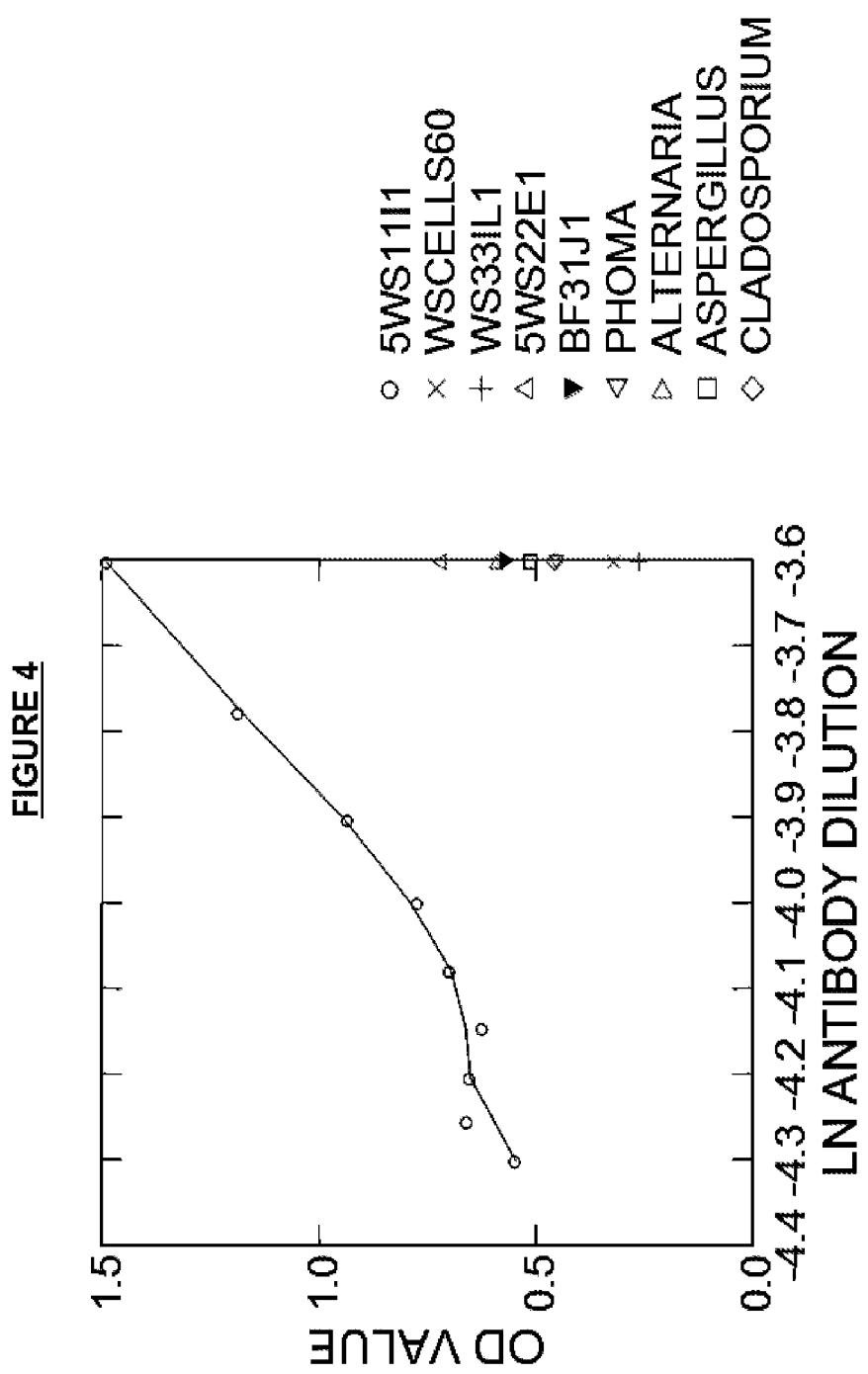
FIG. 4 is a plot of the linearity and avidity of a polyclonal antibody for endophyte 5WS11I1.
Figure 5:
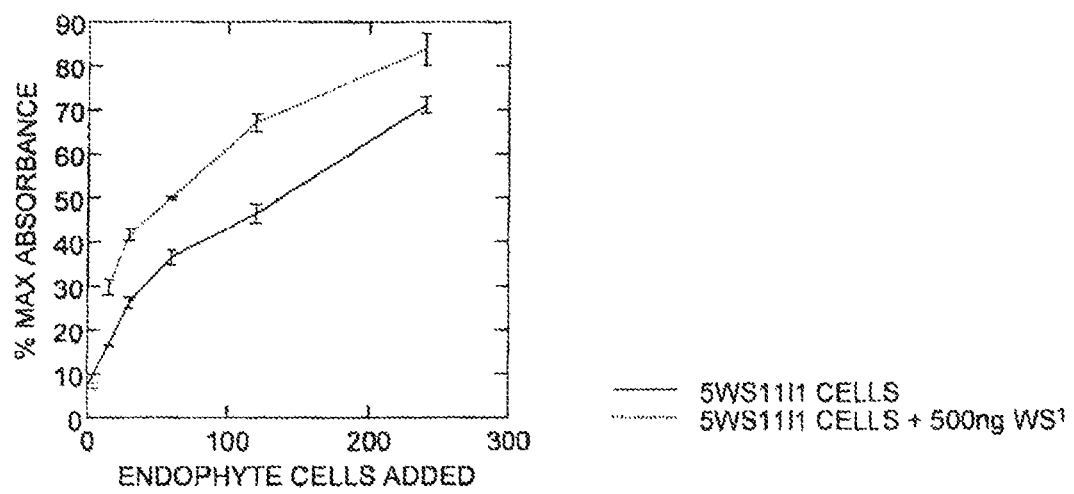
FIG. 5 shows the application of a polyclonal antibody used to detect endophyte 5WS11I1 in planta.

FIG. 4 shows that quantification of the target endophyte was not affected by the presence of larger amounts of powdered freeze dried needles (~2-18 x). By ANOVA with Fishers LSD test, the response for 500 ng needle material plus 30 ng target endophyte was significantly greater than that for the 15 ng combination (p=0.000) as well as all values above. All remaining p values between endophyte needle cell additions were >0.003. Absorbance values for 30, 60, 120 and 240 ng target endophyte plus needle material and the fungus alone were highly correlated r=0.973 (p>0.000) indicating that the presence of the needle did not affect the linearity of the assay (FIG. 5; results of triplicate experiments presented).

Example 5

Producing the Endophyte Inoculum

Cultures are inoculated by macerating the 2% malt extract agar slant in sterile de-ionized water under aseptic conditions and adding the resulting suspension 5% v/v into 250 mL Erlemeyer flasks containing 2% malt extract in deionized water. These are incubated for 2 weeks at 25° C. on a shaker (3.81 cm through, 220 rpm). This in turn is macerated and added to a stirred jar fermentor adapted for growth of filamentous fungi containing 1% malt extract broth aerated at 0.1 v/v per minute at 280 rpm stirring and 21° C. for 7 days. The cell counts are designed to ensure that each seedling receives 10 propagules as delivered in the greenhouse at the receptive stage of the plant plant applied under environmental conditions that sustain needle wetness.

Provided they are applied during the receptive stage of the seedling the susceptible time window, such inoculations are effective whether the seedlings are lightly wounded or untouched.

For 5WS22E1 and 5WS11I1, the addition of small amounts (mg per seedling) of irradiated needles colonized as described above to the soil in the flats used for commercial seedling production is effective at creating indirect contact between the needles and seedlings for inoculating the seedlings, provided the inoculation and seedlings are at the receptive stage.

Example 6

Method of Inoculation—Seed Stratification

A method of inoculating seedlings comprises adding cells to seeds during the stratification process. This is a process whereby tree seed is soaked in water prior to germination to imbibe water and prepare for seed germination. The method involves adding washed toxigenic endophyte cells produced in fermentation as above i.e. adding fungal cells that have been harvested from the fermentor, centrifunging and resuspending in sterile water followed by immediate addition to the seed stratification bags at the at the soaking stage in the nursery. In one embodiment seeds are soaked in water containing inoculum prior to sowing in the greenhouse during seed stratification.

Example 7

Inoculating with an Endophyte Using the Limited Time Window
Reproducing Infected Seedlings Seedlings produced for all the nursery trials were grown using standard containerized seedling production methods. Each solid wall plastic container is 726 cm2 with 67 cavities per container. The individual cavities are 65 cu cm in volume. The trays are filled with a 3:1 mixture of peatmoss and vermiculite and seeds are sown on top of this media. The seeds are covered with a thin layer of dolomitic limestone grit and trays are watered lightly until saturated. The greenhouse is misted with fine nozzles on an irrigation boom to keep the surface of the media moist. Seeds germinate within two weeks. Fertilization with soluble balanced fertilizer begins when side roots begin to form (3 weeks after sowing). Spruce seedlings will typically be 3 cm in height at 8 weeks after sowing (see FIG. 6).

Experimental inoculation by spraying (for 50 seedling containers) was done by blending 350 ml of fungi cultures with 175 ml of sterile water for 10 seconds. The resulting solution was added to a sterile trigger spray bottle. The entire mixture was sprayed evenly over the 50 containers. Pilot-scale operational application was made using a conventional greenhouse travelling boom sprayer and an injector pump to inject the fungus culture solution into the irrigation line. The boom was 28 ft wide and had 22 T Jet 11004VH nozzles. The culture was injected using a Dosatron Injector (Dosatron International Inc. Florida) with an 11 gallon/minute capacity. The injection ratio was 1:64 at 35 psi. Application was made in the evening so that the foliage would remain moist for the longest period of time. Applications were made on two consecutive evenings with 3 passes made with the boom over the entire greenhouse each evening. Steps are taken to ensure that needle wetness is sustained 12 h post inoculation without washing the inoculum off the needles.

A series of medium scale tests have been done since 2000 to determine the optimum time for inoculation. Inoculation has been done using wounded or unwounded seedlings using cultured cells or cells on irradiated needles as above. Pooled data from many trials with 5WS22E1 revealed that there is a period of maximum receptivity regardless of the method of applying the inoculum (FIG. 6), whether tested at 3 months post inoculation or in the cases where more data exist, at 6 months when detectable colonization approximately doubles (Sumarah et al, 2005).

Example 8

Mass Scale Inoculation

Seedlings on the scale of thousands can be inoculated by hand. Plants on the order of 30 million seedlings per year cannot be easily inoculated by hand. The proven method for infecting the needles with the endophyte, albeit with a low success rate, was by wound inoculation of young seedlings. Grass endophytes, are transmitted by seed such that methods applicable to grasses are not applicable to conifer seedling inoculation.

The data were analyzed as follows. From the stored samples of needles from 340 trees positive by culture and ELISA, a random selection of 113 ELISA-positive seedlings was analyzed for rugulosin; most (90%) contained detectable concentrations of rugulosin. The range and distribution of the rugulosin concentrations was similar to that found in earlier tests done in growth chambers (Measurement of a rugulosin-producing endophyte in white spruce seedlings (Sumarah et al. 2005).

Because a complete analysis of the spread of the endophyte could not be done on the field trees, 10 inoculated seedlings that tested positive in a 2003 inoculation trial and 10 inoculated seedlings that were negative by ELISA at 3 months were left in pots at the nursery to grow for an additional year. Each branch was collected separately for analysis by ELISA for rugulosin. There were a variable number of branches (11 to 20) which were carefully labelled according to their position on each of the 20 trees and all were analyzed for rugulosin (~160 samples). All of the inoculated trees that were negative by ELISA were positive after ca. 1 year. This indicates that the true inoculation success is materially underestimated when analyzed at 3 months. Some rate of false negatives from inoculation trials has been noted as an issue since the original inoculation studies in 1999-2002. This data also gives a better sense of the rate of spread and, as observed for the field trees, confirm its persistence. Endophyte and its toxin were shown to be well distributed between new and old growth branches.

The analysis demonstrated the existence of rugulosin as well a rugulosin derivative. This is either a rugulosin-degradation product or a plant modified form of rugulosin. In similar situations, it is known that plants modify fungal metabolites in vivo to protect their own cells from damage without affecting the toxicity of the compound.

Figure 6:
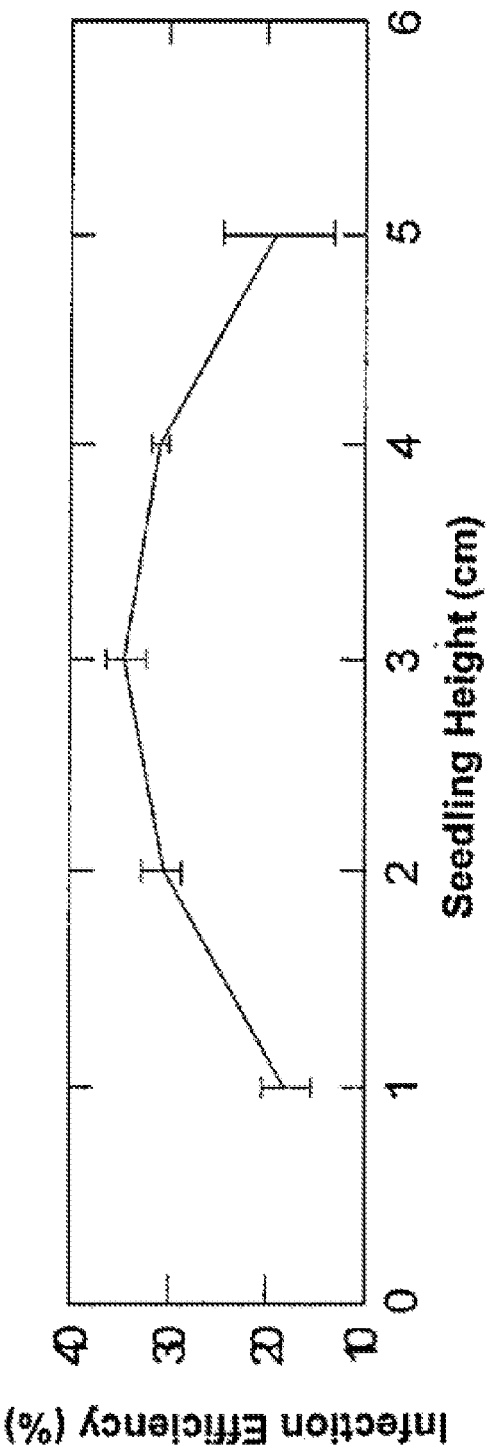
FIG. 6 plots an example of a susceptible time window of seedlings to colonization by toxigenic endophytes.

The 5WS 22E1 trials have been done involved sequential needle inoculations and/or sequential cut and spray inoculations, i.e. from 10 mm, 20 mm, 30 mm, 40 mm and 50 mm height or similar germination to several weeks (see FIG. 6). In each trial, fresh inoculum was prepared and shipped to Sussex since there was evidence that keeping inoculum after preparation at 5° C. resulted in reduced viability with storage time. The needle samples were analyzed (2500 samples). Analysis of the data confirmed that either inoculations by cut and spray, adding needles colonized by the target fungus to the seedling containers or spray alone produces positive results. The three-month colonization rate is highest in the first two treatments but not much less in the spray alone tests. On balance in the several studies of this matter going back to the 1999-2002 period, the success rate by seedling height declined after a peak between >3 cm and 4 cm. Since these are measurements of the seedlings with the highest initial infection rather than the total rate, there is little doubt now of that for endophyte 5 WS 22E1.

The inoculation trials of the second endophyte strain 5WS11I1 were done but just available for analysis in the last quarter of 2004. These involved the cut and spray and colonized needle inoculation methods. These were analyzed (700 samples) and notional colonization success rates were similar to those of 5WS22E1 (the species for which there is >6 years of experience) i.e. ~⅓$^{rd}$ positive. The effect of seedling age (height) was similarly confirmed.

Example 9

Spread of Inoculated Strains

As a necessary condition to using this technology under field conditions, a test site is needed where the developing inoculated trees can be repeatedly tested over a 5 year period.

It is thought that these endophytes are transmitted in nature from cast needles from colonized trees. To address this question, young seedlings would be planted around the colonized developing trees.

In the spring of 2000, ~1200 seedlings were inoculated with 5WS22E1. From all this work, 340 trees were endophyte-colonized. The trees had been inoculated and cultured at the Sussex Nursery under normal conditions. They were repotted and kept in the holding yard. In August of 2003, 300-four year old trees were planted with greater spacing than normal. In July 2004, 5 small seedlings in were planted around 50 5WS22E1 positive trees. Screens were placed around an additional 50 test trees to collect cast needles.

Approximately 300 mg (dry weight) of needles were removed from each of the one, two and three year old braches as well as two further branches were tested for the presence of endophyte 5WS22E1 by ELISA and rugulosin by HPLC. These needle samples were analyzed in 2005. All trees were positive for the fungus and the toxin through each of the age classes of needles on the tree. At the respective limits of detection (30 ng for the endophyte; 150 ng/g for the toxin), 63% of the samples of the individual branches were positive for the endophyte by ELISA and 89% were positive for either rugulosin or its degradation product, and only 1 branch was negative for both. The concentration of rugulosin was somewhat higher in the field trees than in previous studies but the trees were older and more established. The average concentration was right at the effect level for spruce budworm and was variable between trees but no biases toward either older or newer branches were found. Cast needles collected in netting around these trees were tested and no toxin was present.

Example 10

Inoculation with Vermiculin-producing Strain 5WS11I1

The vermiculin-producing strain 5WS11I1 was chosen for the second candidate strain (Mycological Research 106:47). A polyclonal antibody was developed for the determination of the fungus. In the spring of 2004, seedlings were inoculated.

The inoculation trials using the vermiculin-producing endophyte had a three-month success rate by ELISA of approximately 30% similar to endophyte 5WS 22E1. From experience it is likely that the 6-8 month success rate will be much higher, again because the spread of the endophytes is slow.

Because vermiculin has an unremarkable UV spectrum, the quantification of this chemical is more difficult than for rugulosin. During this work, improvements to the analytical method had to be made as naturally contaminated samples became available for the first time (the previous method development experiments were necessarily done with spiked control needles). This means that some sense of the actual concentration of vermiculin in naturally-contaminated material was acquired for the first time. The earlier experiments with spiked needles were necessarily done in concentration ranges that made sense compared to rugulosin which, in the event, were a bit too high.

At three months post inoculation, no vermiculin could be detected in ELISA-negative samples. From the ELISA-positive seedlings, 30% contained vermiculin. This demonstrates—for the first time-that this toxin is produced in vivo and can be one of the endophytes used for inoculation.

Essentially all of the white spruce endophytes isolated in the present project at the Sussex lab were cultured and analyzed by HPLC for metabolite production. From these, 30 had interesting profiles based on diode array detector response (measures UV spectrum of each compound passing through the detector). The extracts with the highest total amount of compound were screened using the Oxford assay for anti-yeast toxicity. Although yeasts are not insects, *Saccharomyces cerevisiae* is eukaryotic. From these, five produced reasonably potent compounds. The compounds were demonstrated to be complex by HPLC Mass Spectroscopy and NMR. One of these, 05-037A, was the most potent in the yeast assay and the compounds found were demonstrated to be complex and not related to other endophyte toxins seen so far. It was grown in a large scale fermentation (5 L), extracted and the metabolites were isolated using a variety of techniques including; prep thin layer chromatography, prep HPLC and column chromatography. The compounds were all generally small in molecular weight <350 (233, 237, 309, 221, 154, 218) and range from moderately polar to non polar. The last step required was further purification to obtain isolated metabolite for complete structure determination. This strain was grown in culture on a sufficient scale to permit the isolation and characterization of its metabolites.

Example 11

Inoculation Rate and Persistence of Fungal Endophytes

Ten inoculated seedlings that tested positive in a 2003 inoculation trial and 10 inoculated seedlings that were negative by ELISA at 3 months were left in pots at the nursery to grow for an additional year. Each branch was collected separately for analysis by ELISA for rugulosin. There were a variable number of branches (11 to 20) which were carefully labelled according to their position on each of the 20 trees and all were analyzed for rugulosin (~160 samples). All of the inoculated trees that were negative by ELISA were positive after ca. 1 year. This indicates the true inoculation success is materially underestimated when analyzed at 3 months. The data also give a better sense of the rate of spread and, as observed for the field trees, confirm its persistence. It was very useful to demonstrate that endophyte and its toxin were shown to be well distributed between new and old growth branches.

Example 12

Isolation of Red Spruce Toxigenic Endophytes

Many toxigenic endophytes that infect white spruce have been identified and partially sequenced. These include the strains identified in Table 1. In addition other white spruce and some red spruce endophytes that produced anti-insectan toxins were identified. The purpose is to generate a comprehensive collection of red spruce endophytes and screen them for anti-insectan metabolites. Approximately 70 endophytes had been cultured, and subjected to preliminary metabolite screening. Fractions were prepared for budworm and further chemical assays.

Extracts from the 70 red spruce as well as some white spruce endophyte strains which had been qualitatively screened for the production of potentially anti-insectan metabolites and for which there are DNA sequence data were incorporated into synthetic diet. These were individually poured into small containers (milk cups) and allowed to harden. Second instar spruce budworms were added to the small containers containing endophyte extracts as well as to together with controls and rugulosin was used as a positive control.

Tests using the spruce budworm assay found that several isolated endophyte strains were toxic. Isolated endophyte strains that were found toxic using this assay include 06-264A, 06-332A, 08-011D, 06-268A, 07-013D, 01-002A, 06-268A, 03-020B, 04-012A, 06-063D, 06-073C, 02-002C, 06-094E, 06-219A, 06-264A and 06-255A.

RED SPRUCE Data

Test 1

| | | | | |
|---|---|---|---|---|
| HC | 52 | 0.000 (06-264A) | 60 | 0.073 (08-011D) |
| | 58 | 0.026 (06-332A) | | |
| WT | 52 | 0.054 | | |
| | 54 | 0.009 (06-268A) | | |
| | 58 | 0.057 | | |
| | 59 | 0.008 (07-013D) | 62 | 0.082 ((01-002A) |

Test 2

| | | | | |
|---|---|---|---|---|
| HC | 14 | 0.058 (04-002G) | 9 | 0.078 (03-020B) |
| WT | | | 9 | 0.070 |

Test 3

| | | | | |
|---|---|---|---|---|
| HC | 14 | 0.058 | | |
| WT | 17 | 0.052 (04-012A) | 9 | 0.071 |

Test 4

| | | | | |
|---|---|---|---|---|
| HC | 27 | 0.039 (06-063D) | | |
| WT | 27 | 0.011 | | |
| | 28 | 0.008 (06-073C) | 5 | 0.079 (02-002C) |

Test 5

| | | | | |
|---|---|---|---|---|
| HC | 38 | 0.015 (06-094E) | 45 | 0.087 |
| | 43 | 0.000 (06-219A) | 47 | 0.082 (06-264A) |
| | 45 | 0.005 (06-255A) | | |
| WT | 38 | 0.034 | | |
| | 43 | 0.002 | | |
| | 45 | 0.016 | | |
| | 47 | 0.042 | | |

Example 13

Isolation of Toxigenic Endophytes

The white spruce endophytes were cultured and analyzed by HPLC for metabolite production. From these, 30 had good profiles based on diode array detector response (measures UV spectrum of each compound passing through the detector). The extracts with the highest total amount of compound were screened using the Oxford assay for anti-yeast toxicity. Although yeasts are not insects, *Saccharomyces cerevisiae* is eukaryotic. From these, five produced potent compounds. The compounds were demonstrated to be complex by HPLC Mass Spectroscopy and NMR. One of these, 05-037A, was the most potent in the yeast assay (Vincent and Vicent, 1944, except using. *Saccharomyces cerevisiae*) and the compounds found were demonstrated to be complex and not related to other endophyte toxins seen so far. It was grown in a large scale fermentation (5 L), extracted and the metabolites were isolated using a variety of techniques including; preparatory thin layer chromatography, preparatory HPLC and column chromatography. The compounds were all generally small in molecular weight <350 (233, 237, 309, 221, 154, 218) and range from moderately polar to non polar. The last step required was further purification to obtain isolated metabolite for complete structure determination. This strain was grown in culture on a sufficient scale to permit the isolation and characterization of its metabolites.

A total of 62 extracts were tested in the spruce budworm assay plus a larger number of controls for each set. Of these 11 white spruce extracts were toxic to spruce budworm (i.e. statistically different from controls either for weight reduction (most common), head capsule width or both). For the red spruce extracts, 21 were toxic to spruce budworm. The DNA sequence for isolated red spruce toxigenic isolates is listed in SEQ ID NO: 6-28.

Example 14

Isolation and Inoculation of Pine Tree Toxigenic Endophytes

Pine needles are collected from pine trees. Slow growing endophytes are cultured from needles and screened for the presence of toxigenic endophytes. Antibodies to candidate toxigenic endophytes are produced. Candidate toxigenic endophytes are tested in vitro for their effect on pests, including disease-causing fungi including white pine blister rust. Endophytes that are toxigenic in vitro are selected for in vivo tests. An inoculum comprising the toxigenic endophyte is prepared. Pine seedlings are inoculated with the inoculum during a susceptible time window. Colonization is later confirmed using a specific antibody test.

Example 15

White pine seedlings are inoculated with a toxigenic endophyte and coloniziation is confirmed as described elsewhere. Colonized and control white pine needles are exposed to white pine blister rust. Damage is assessed and compared to control. Toxigenic endophyte colonized white pine seedlings are resistant to white pine blister rust growth and damage.

Example 16

The inventors have shown the role played by endophytic fungi in limiting conifer needle herbivory.

Successful experimental inoculation of *P. glauca* seedlings with anti-insectan toxin producing needle endophytes has been demonstrated in previous studies conducted in growth chambers and under nursery conditions using wound inoculation (Miller et al. 2002; Sumarah et al. 2005). In the former studies, occurrence of the fungus and its toxin in needles reduced the growth rate of *C. fumiferana*. A number of studies have since been conducted by the inventors with the rugulosin-producing endophyte 5WS22E1 (DAOM 229536, CBS 120377) first reported to produce (+)rugulosin by Calhoun et al. (1992). Based on DNA sequence information, this fungus is a species of *Phialocephala* related to strains previously reported as endophytic in Norway spruce (Gruenig et al. 2002).

Rugulosin has been isolated from disparate fungi including strains of conifer endophytes from strains collected by the inventors, from *Aschersonia samoensis* P. Henn. (Watts et al. 2003), as well as the organism from which rugulosin was first reported, *Penicillium rugulosum* Thom (Bouhet et al. 1976; Breen et al. 1955). It is toxic to *C. fumiferana* larvae in an artificial diet (Calhoun et al. 1992) and in needles (Miller et al. 2002). Rugulosin has been reported as toxic to *Drosophila melanogaster* (Dobias et al. 1980) and to ovarian cells of the fall armyworm, *Spodoptera frugiperda* (Watts et al. 2003). Based on limited studies, rugulosin has very low mammalian toxicity ($LD_{50}$ 55 mg $kg^{-1}$ BW ip in mice and 44 mg $kg^{-1}$ BW in rats; Ueno et al. 1971). Rugulosin was not cytotoxic to HepG2 cells (human hepatoma cells; Watts et al. 2003). It has been reported by many authors as an antibiotic to both Gram positive and negative bacteria (e.g. Stark et al. 1978) and is moderately antifungal (Breen et al. 1955).

The inventors investigated the spread and persistence of the endophyte and its toxin in trees maintained in the nursery as well as under field conditions. Additionally, some data on the toxicity of rugulosin to some other species of insects herbivorous on *P. glauca* are demonstrated.

Materials & Methods

Effects of Dietary Rugulosin on Various Insect Larvae

*C. fumiferana* larvae (spruce budworm) were obtained from Insect Production Services, Forestry Canada (Sault Ste. Marie, ON) and stored at 5° C. For each test, a sufficient number of larvae were hatched and put in creamer cups containing 15 ml of artificial diet. The diet was prepared in-house (McMorran 1965). The cups were placed in a growth chamber at 22° C., 55% RH with 16 h light/day until the larvae reached second/third instar (McGugan 1954). A suitable amount of diet was prepared, and 4 aliquots dispensed into a flask. Dilutions of pure rugulosin were made in 95% ethanol to provide the required concentrations (540 µl ethanol solution plus the vehicle control) and added to the flasks respectively. The diet was mixed with a stir bar and by the pipette used to dispense the media. Two drops of hot liquid diet were added with a 10 ml sterile pipette (0.1 g dry weight) to 4 ml tapered plastic sample cups (Fisher Scientific #025444, #25444A). Vials containing diet and toxin were freeze-dried to eliminate the ethanol and rehydrated with 60 µl sterile water. One larva was placed in each vial, which was returned to the growth chamber to feed for 4 d. After 4 d, all larvae were frozen and weighed on a Mettler 163 analytical balance (±0.02 mg). Previous studies demonstrated that the frozen wet weight was correlated with dry weight ($p<0.001$). Head capsule widths were determined using a stereo microscope at 40× with ocular and stage micrometers. *C. fumiferana* were tested in two treatments, the first with concentrations of 5, 10 and 50 µM (75 insects per concentration tested) and the second with rugulosin concentrations of 25, 50 and 100 µM (75 insects per concentration tested), which was repeated.

*Lambdina fiscellaria* eggs (hemlock looper) were purchased from Forestry Canada in three lots. The eggs were incubated at room temperature for 10 d until larvae emerged. Larvae from each batch emerged within two days of each other and were immediately put on diet in cups as above. After they had grown to second instar (~1 week), larvae were placed in test vials following the same procedure as for the *C. fumiferana* with a concentration range of 5, 10 and 50 µM rugulosin for the first test and 10, 50, 100 and 150 µM for the second test, which was repeated (~67 larvae per concentration). After 1 week on the test diets, the larvae were frozen, weighed and head capsule width determined.

*Zeiraphera canadensis* larvae (spruce budmoth) were collected from the wild near Sussex in mid June. They were immediately put in test vials and tested at rugulosin concentrations of 10, 50, 100 and 150 µM (75 per concentration). After seven days, surviving larvae were frozen and measured.

Preparation of Trees and Field Site

A description of the trees and inoculation methods used in these experiments are given in Sumarah et al. (2005). Three hundred (some of the original 330 positives died) of the endophyte/toxin-positive trees from Sumarah et al. (2005) were planted with greater spacing than normal at a test field site ca. 30 km from Sussex, NB, Canada. The site has excellent soil characteristics and uniformity. The original forest stand type was mixed wood with red spruce, balsam fir, white birch, yellow birch and sugar maple. The site was prepared for planting using one pass with a Marden Roller and another pass with anchor chains and shark-finned barrels. Half the seedlings were planted on a part of the cut block which was well drained and the other half were planted in a wetter area with some seepage.

One year later 250 (fifteen month old) un-inoculated seedlings were obtained as previously described, from the J.D. Irving Ltd. genetic improvement program (Sumarah et al. 2005). They were grown in the greenhouse and then moved to an outdoor holding area where they over-wintered. Five of these in-noculated seedlings (20-30 mm tall) were planted around each of 50 randomly selected trees from the 300 planted on this field site. Following that, fibreglass screens comprising an area of 0.25 $m^2$ were placed around a further 50 test trees to collect cast needles.

Later, complete branches representing each age class of needles were harvested and frozen from 8 randomly selected trees from the original 300 planted in the field site. In the fall of the next year similar samples were collected and frozen from 8 different trees from the field site, including branches from one to three-year needle classes (the trees were larger). In addition, two of the small seedlings planted around the field trees the previous year were collected from around three of the test trees sampled. Cast needles from all available screens were collected in both years as pooled samples from which extraneous materials (pebbles, leaves, etc.) were removed by hand.

Within Tree Spread of Endophyte

A separate set of 1100 seedlings (not previously reported on) were inoculated after Sumarah et al. (2005). Eight months later they were tested for endophyte colonization by ELISA as previously described. These trees were then transferred to pots and allowed to grow at the Sussex nursery. Approximately seven months later each branch from 10 endophyte-positive seedlings and 10 endophyte-negative trees (based he previously conducted ELISA test) were harvested, placed into sterile plastic bags, carefully labelled according to height and compass direction and frozen.

ELISA and Rugulosin Analyses

Needles were removed from the branches, freeze dried and used for both antibody and toxin analyses after Sumarah et al. (2005). Relative standard deviation of the positive control was ~9%. The method limit of detection (LOD) for cell mass (e.g for antibody detection) was 60 ng $g^{-1}$ and the limit of quantification (LOQ) i.e. a positive was 120 ng $g^{-1}$ dry weight of needle. The LOD and LOQ for rugulosin were both 150 ng $g^{-1}$ (Sumarah et al., 2005).

As large numbers of needle analyses were completed, it was noted that some samples contained a stoichiometrically-produced (1:1) degradation product occurring as a function of delay in drying (100% conversion after one week). Under the HPLC conditions described above, this compound elutes 30 s prior (UV max: 210, 240, 275, 326 nm) to rugulosin (UV max: 210, 254, 389 nm). The material was analyzed by mass spectrometry using direct injection triple quadropole electrospray mass spectrometer (Micromass), LC/MS using a LCT time-of-flight mass spectrometer (Micromass) and LC/MS on a QTOF (Micromass). No consensus on a molecular mass was reached because the molecule did not ionize consistently in any of the machines used. NMR analyses were done on a Bruker Advance 700 mHz NMR spectrophotometer (COSY, HSQC and HMBC). These data indicated that the compound contained a ring with 4 adjacent hydrogen atoms and two O-methyl groups which is chemically consistent with, rugulosin having broken in two and having undergone a rearrangement. Where degradation product occurred, the value was added to the total value.

Statistical analyses were done with SYSTAT v 10.2 (San Jose, Calif.). For statistical purposes needles that were negative for rugulosin but positive by ELISA were entered at the detection limit. Negative values were entered at half the detection limit.

Results

Insect Tests

*C. fumiferana* larvae fed ≥25 μM rugulosin weighed significantly less than the respective controls by ANOVA (25 μM: p=0.027, 50 μM: p=0.001 and 100 μM: p<0.001). Larvae fed 100 μM dietary rugulosin also had a significantly reduced head capsule (p=0.008). Significance values given are for the second trial which were similar to the repeat.

*L. fiscellaria* larvae fed ≥50 μM weighed significantly less than the respective controls. During the second test, the weights of *L. fiscellaria* fed rugulosin were significantly lower than controls (ANOVA, 50 μM: p=0.030, 100 μM: p=0.081 and 150 μM: p=0.001). For the third trial the results were similar (50 μM: p=0.034, 100 μM: p=0.046 and 150 μM: p=0.001). Larvae fed 150 μM dietary rugulosin also had a significantly reduced head capsule (p=0.028).

*Z. canadensis* larvae did not perform as consistently since these were collected in the wild. Many (60%) succumbed to fungal infections (*Aspergillus fumigatus*) and other unknown causes over the course of rearing. Larval weights between controls and the treatment groups (10, 50, 100 and 150 μM rugulosin) were not significantly different by ANOVA (LSD, Tukey). However, using the Wilcoxon matched-pairs signed-ranks test, the larvae fed 100 or 150 μM rugulosin in the diet were lighter than those fed the 10 μM rugulosin and control diets (p<0.10). Because of the high percentage of *A. fumigatus*-contaminated larvae in the experiment, an unanticipated result was the antifungal activity observed above 50 μM, few vials had fungal growth in the tests at 100 μM and 150 μM rugulosin. Breen et al. (1955) reported that rugulosin was moderately antifungal.

Results from Test Field Site Samples

Samples were taken approximately 3.5 and 4.5 years post inoculation at just over one and two years in the field, respectively. The trees were 1-1.25 m, and 1.5-1.75 m high at that time. From each of the eight trees a branch was selected from each of the one, two and three year old needle classes (24 branches total). All of the needle samples from the 24 branches were positive by ELISA and 96% contained detectable rugulosin at one year in the field and 3.5 years post inoculation. Mean concentration corrected for recovery was 1.0 μg $g^{-1}$ and rugulosin concentrations from each age class of needles were virtually identical. From the 8 different trees collected as above 4.5 years after inoculation (24 branches total), 40% of the samples were positive by ELISA but 100% contained rugulosin. Mean concentration corrected for recovery was 0.7 μg $g^{-1}$ and rugulosin concentrations from each age class of needles were again virtually identical. All six of the needle samples from the uninoculated seedlings that were planted immediately under the three positive trees in the field were positive for rugulosin with a mean concentration corrected for recovery of 1.1 μg $g^{-1}$ (5/6 were positive by ELISA).

No rugulosin was detected in the cast needles collected in netting around these trees from samples taken in either year. Samples taken trees after year one were positive by ELISA and in year two, they were negative.

Within Tree Spread of Endophyte

Figure 9:
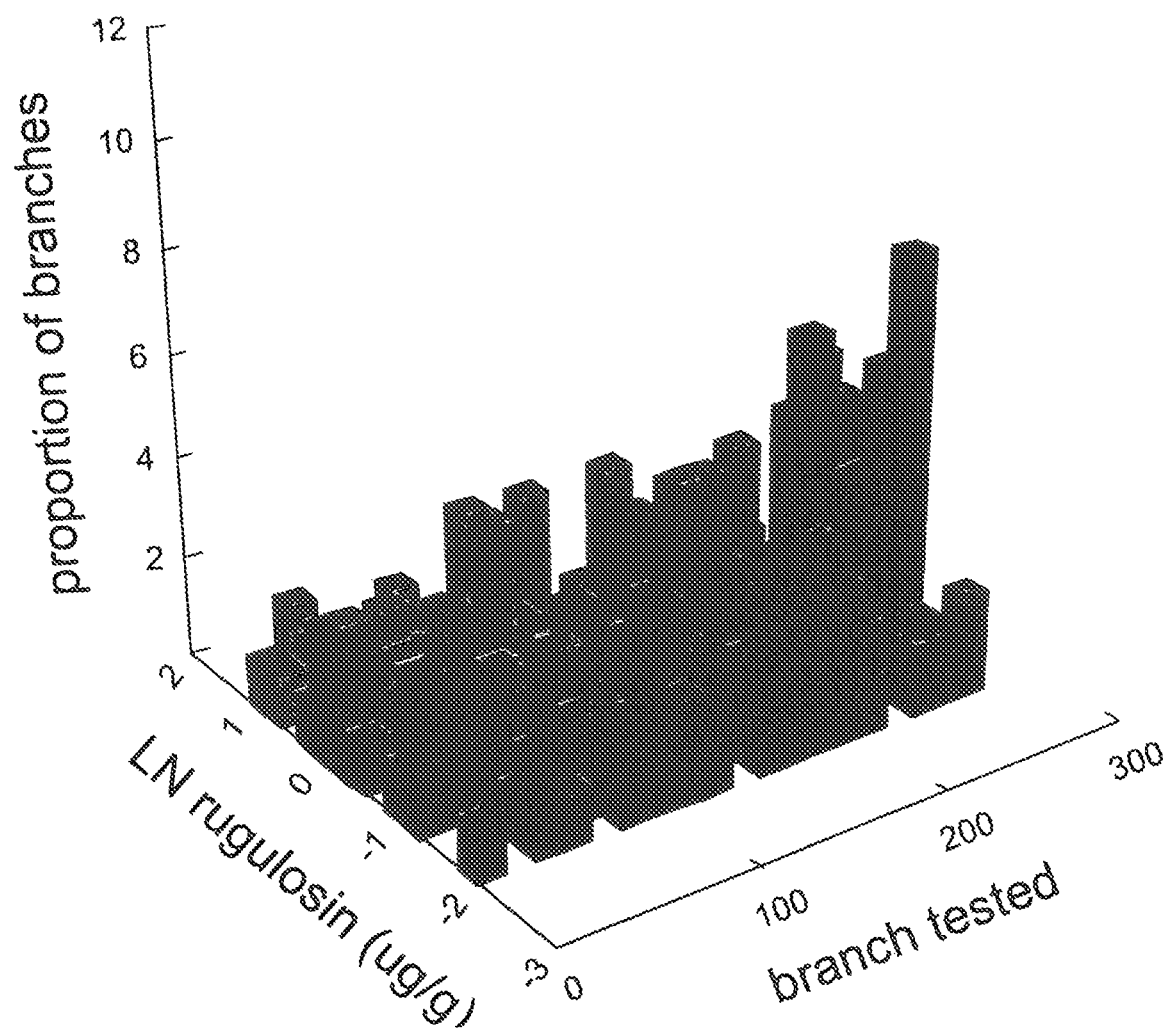
FIG. 9 is a 3D histogram showing needle ruguslosin concentration in ~300 branches from 20 trees 15 months post inoculation with endophyte 5WS22E1 in relation to the proportion of samples; geometric mean concentration was 0.8 $\mu g\ g^{-1}$.

Eleven to 20 branches were recovered from each of 20 trees 15 months after inoculation. Approximately 90% of the branches from the 10 ELISA-positive trees, tested positive for the fungus and or the toxin. Of the seedlings that had tested negative 11 months prior, 4 months after inoculation, 75% of the branches were positive for the fungus and/or the toxin at 15 months. There was a difference in the rates of false negatives by ELISA compared to the presence of rugulosin by toxin analysis between the two groups. The rate was approximately 2× the rate in inoculated trees that had tested ELISA negative originally, compared to those that tested positive (p>0.036). Because the trees were all colonized, the data were pooled. Arithmetic mean concentration of rugulosin (corrected for recovery) was 0.6 μg $g^{-1}$ and the geometric mean was 0.8 μg $g^{-1}$ (FIG. 9).

Discussion

The inventors have shown the effects of rugulosin from the *Phialocephala* species endophyte on herbivorous insects, the within-tree spread of inoculated endophytes, endophyte and toxin persistence and spread of endophytes to adjacent seedlings.

This analysis confirmed the toxicity of rugulosin to *C. fumiferana* and other insects, placing the effective concentration at 25 μM (p=0.027 for weight reduction compared to controls). Under the conditions used, *L. fiscellaria* were affected at dietary rugulosin concentrations between 25 and 50 µM. The tests with wild collected *Z. canadensis* were incomplete because a high percentage of the wild-collected larvae were infected with *A. fumigatus*. However, this insect was also affected by rugulosin in the same order of magnitude of concentration as the other insect species. As noted, the dietary toxicity of rugulosin to *D. melanogaster* was in the same range (50 µM; Dobias et al. 1980). Rugulosin will also have the desired toxic effect on a variety of forestry pests from within colonized needles.

The results of the present experiment conducted in the nursery showed a number of important findings. At 15 months post inoculation the trees were thoroughly colonized with only 32 branches from 320 testing negative at the detection limits of the two methods. However, it also turned out that the large majority (75%) of the trees that had tested negative by ELISA at three months post inoculation were also positive after a longer period in the nursery. In addition, there were indications that there was variation in the performance of the ELISA due to variations in the UV absorbing compounds in the needles. Needle colour can vary due to environmental or genetic reasons. The present study provided a quantitative perspective. However, the dominant effect relates to the sensitivity of the two methods which none the less was in the 100 ppb (60 and 150 ng $g^{-1}$) in relation to the extent of colonization. In summary, the endophyte and its toxin were shown to be well distributed between branches 15 months post inoculation.

The trees planted in the field had been selected for planting on the basis of rugulosin and ELISA response. At three and a half years no needles would have arisen from tissues that were present at the time of inoculation. Virtually all the needle samples from the three age classes of needles from the two different groups of trees were found to contain rugulosin.

One year after planting, the modest sample of small seedlings planted immediately under the trees (i.e. in the zone where cast needles would fall) were all colonized. The invention provides the first evidence that conifer needle endophytes are transmitted vertically.

In all three groups of trees, rugulosin needle concentrations were approximately 1 μg $g^{-1}$. Notionally, this concentration is on the order of 10 μM. Compared to the data on the effective concentrations in vitro, this concentration is in approximately the right order of magnitude for the predicted effect on insect growth, consistent with the results obtained in growth chambers (Miller et al. 2002). Artificial diet represents an unlimited supply of nutrients which is generally protective of low-level toxic effects in any animal model. It is difficult to know the distribution of toxin in planta. Scanning electron micrographs indicated that endophyte mycelium extensively occupied the intercellular spaces of balsam fir needles (Johnson & Whitney 1989). It is known that the concentrations of excreted toxins are greatest near the mycelium (e.g. Morita et al. 1984). This suggests that the concentrations encountered by the insect in digestible material might have been slightly higher. Lower needle concentrations may be sufficient to reduce pest growth.

The absence of detectable toxin in the cast needles was consistent with expectations. Because mycotoxins are natural products, they are rapidly degraded when in ground contact (e.g. Binder et al. 1996; Mortensen et al. 2006). Cast needles retain toxigenic endophytes for sufficient time to permit vertical transmission.

In summary, the inventors have shown that the slow growth of conifer endophytes constrains the early detection after colonization. Once inoculated, the test endophyte spread throughout the developing tree persists under field conditions at least for four years. Additionally, the inventors have shown reduction in body weight for both the *C. fumiferana* and *L. fiscellaria* at 25 and 50 μM rugulosin, respectively, and head capsules were reduced at 100 and 150 μM. *Z. canadensis* were lighter when tested with 100 and 150 μM rugulosin compared to controls.

Example 17

Toxic metabolites produced by endophytic fungi (*Epichloë* and *Neotyphodium* species) in fescue grasses greatly reduce the populations of associated herbivorous insects. This has a significant beneficial effect on plant fitness. These fungi produce various alkaloids that affect herbivore growth (insects, mammals; Clay and Schardl, 2002) and they are found in plant tissues in the 1-30 μg $g^{-1}$ range (Rottinghaus et al., 1991; Spiering et al., 2005). There is some evidence for translocation of the toxins as well as a possible role of plant enzymes in changing their structures (Spiering et al., 2005). There is also one report that the presence of the endophyte directly affects the growth of a nematode that damages one grass species, regardless of the toxins (Panaccione et al., 2006).

The inventors have been studying the role of endophytes in *P. glauca* (white spruce) in limiting conifer needle herbivory by *C. fumiferana* and some other insect species. *C. fumerana* is a major cyclical pest of spruce and fir trees, especially in the northeast US and Canada (Royama et al., 2005). Over two decades, the inventors have collected foliar endophytes of conifers from the Acadian forest and studied them for their ability to produce compounds toxic to *C. fumerana* larvae.

Successful experimental inoculation of *P. glauca* seedlings with the needle endophyte 5WS22E1 (DAOM 229536, CBS 120377) which produces rugulosin has been demonstrated by the inventors in studies conducted in growth chambers and under nursery conditions using wound inoculation. Based on DNA sequence information, this fungus is a species of *Phialocephala* related to strains previously reported as endophytic in Norway spruce (Grunig et al., 2002). Grown under nursery conditions, needle samples from two-year old infected trees contained 0.15 to 24.8 μg $g^{-1}$ rugulosin with a geometric mean concentration of 1 μg $g^{-1}$. The inventors have shown that young trees have a uniform distribution of toxin so the variation in concentration is largely between individuals. As the trees age, there is inter-branch variation in rugulosin concentration. Once inoculated as seedlings, trees in a test site maintained similar needle rugulosin concentrations 5 years post inoculation.

In growth chamber studies, occurrence of the fungus and its toxin in needles reduced the growth rate of *C. fumerana*. In vitro, rugulosin reduced body weight and/or affected instar development in *C. fumerana* (Calhoun et al., 1992), *Lambdina fiscellaria* and *Zeiraphera canadensis* at dietary concentrations in the 50 μM range. The study shows that similar concentrations of rugulosin in needles reduced the growth of *C. fumerana* in nursery-grown trees.

Materials and Methods

Nursery experiments: The tests were conducted at the J.D. Irving, Limited Sussex Tree Nursery in New Brunswick, Canada (45° 43' N, 65° 31' W; elevation 21.30 m). In two successive years, several hundred seedlings grown as container stock in mulitpot 67 seedling containers were inoculated with the rugulosin-producing endophyte 5WS22E1 (DAOM 229536; CBS 120377). A description of the *P.*

*glauca* populations, planting and inoculation methods used in these experiments is given in Sumarah et al. (2005) All trees were labeled with 9 digit codes and all measurements done with the samples blinded.

Three-year old seedlings: The first group was sown and inoculated approximately two months later. After four months in the greenhouse, they were tested for endophyte colonization by ELISA (Sumarah et al., 2005) and segregated. Along with 5WS22E1-free seedlings from the same crop, the endophyte-positive group was maintained under commercial conditions as are known in the art. After one year, all seedlings were transplanted into plastic pots and held at the nursery site for one more year post inoculation.

Four year-old seedlings: The second group were from a test sown and inoculated approximately 12 weeks later. These had been tested for endophyte infection after 4 months of growth by ELISA. The seedlings were transferred to pots after one year and held as above.

Experiment 1 with younger trees: This comprised 100 trees, 50 of which were infected with the endophyte and a similar control group. Five second instar larvae were placed on first year lateral branch on shoots with buds on each tree using a fine artist's brush (nylon #5). The buds were swelling when the larvae were applied. Insects were obtained as second instar larvae from Insect Production Services, Natural Resources Canada, Canadian Forest Service (Sault Ste. Marie, ON) and stored at 5° C. until use. The whole tree (the experimental unit) was covered with a mesh screen bag (polyester drapery shear material) prepared after Parsons et al. (2005) for both endophyte-positive and negative trees.

Experiment 2 with Older Trees

Figure 10:
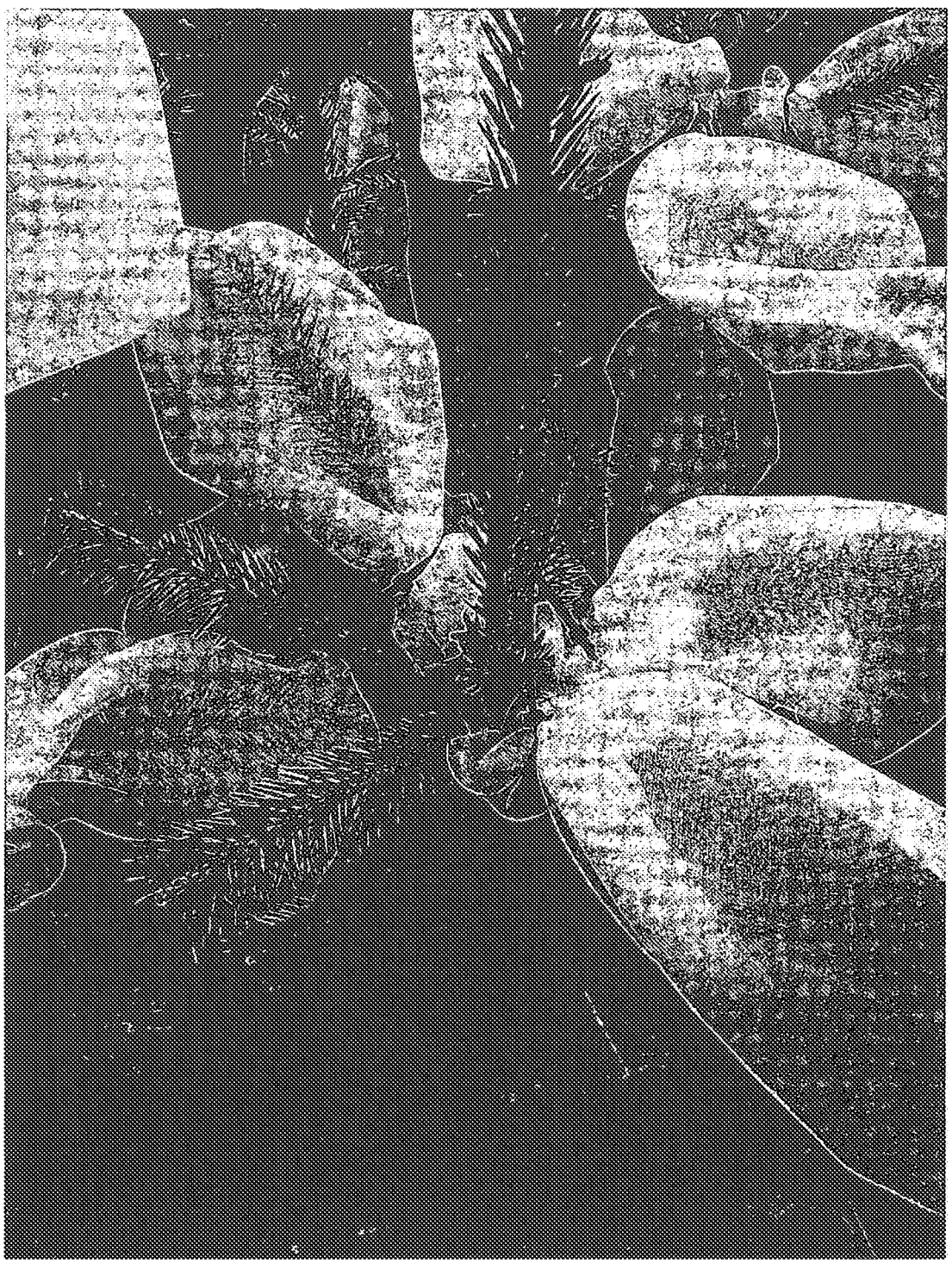
FIG. 10 is a photograph of four year old trees showing mesh coverings on individual branches.

Two budworms were placed as above on each of 3 or 4 first-year branches on shoots with buds on each of 48 four-year old trees. Each branch (the experimental unit) was then covered with a mesh bag (FIG. 10). This experiment permitted a factorial analysis of inter-tree (differences in needle chemistry due to shade history, needle class, etc.) and inter-branch variation in rugulosin concentration.

Two budworms were placed as above on each of 3 or 4 first-year branches on shoots with buds on each of 48 four-year old trees. Each branch (the experimental unit) was then covered with a mesh bag (FIG. 10). This experiment permitted a factorial analysis of inter-tree (differences in needle chemistry due to shade history, needle class, etc.) and inter-branch variation in rugulosin concentration.

The use of too many insects would have defoliated the trees regardless of the presence of the toxin in most if not all treatments. The number of budworm on the two sizes of trees in the present study was based on data from Parsons et al. (2005). They showed that the lowest detectable damage on balsam fir of early instar sawfly larvae occurred at a density of 50 larvae/m$^2$ branch.

Temperature recorders (Hobo Dataloggers, Onset Computer Corporation, Pocasset, Mass.) were placed in the holding area and the progress monitored until the budworms were not older than sixth instars. At termination, all the insects that could be found were collected and frozen individually. These were weighed on a Mettler PJ360 analytical balance (±0.02 mg). Previous studies demonstrated that the frozen wet weight was correlated with the freeze-dried weight (n=134 animals, Pearson correlation r=0.841, Bonferroni-adjusted P<0.0001). Head capsule widths were determined using a stereo microscope at 40× with ocular and stage micrometers. After collecting the budworm, the trees were sprayed with insecticide to ensure that no larvae survived to escape.

Both experiments were terminated 1 month later and 5-6 lateral branches were removed from the three-year old trees and frozen. The branches where budworms were collected from the four year old trees were removed and frozen individually. Needles were removed from all branches individually, freeze dried and used to determine infection by ELISA and rugulosin after Sumarah et al. (2005). The method limit of detection (LOD) for cell mass was 60 ng g$^{-1}$ and the limit of quantification (LOQ), i.e. a positive, was 120 ng g$^{-1}$ dry weight of needle for antibody detector. The LOD and LOQ for rugulosin detection were both 150 ng g$^{-1}$.

ANOVA with the Tukey-Kramer test were performed on the weights and head capsule widths of the insects from the three year old trees using NCSS 2004 software (Kaysville, Utah). An equal variance t-test was also done on the weights using the same software.

On the four year old trees, insects were stratified into those collected from needles with toxin concentrations below the dietary toxic effect level for rugulosin of 0.5 µg g$^{-1}$ and those ≥0.5 µg g$^{-1}$. This was based on the dietary low observed effect level of rugulosin for *C. fumerana* in synthetic diet (ca. 50 µM; Calhoun et al., 1992) adjusted for mean ratio of dry weight:wet weight for needles. For statistical purposes, needles that were negative for rugulosin but positive by ELISA were entered at the detection limit. Values below the detection limit were entered at half the detection limit. Routine statistical tests on the remaining data as well as the paired t-tests, Wilcoxon signed rank test and ANOVA were done on the data from the four year old trees using SYSTAT v 10.2 (San Jose, Calif.).

Mean temperature was 18.4±2.2° C. starting at 15-17° C. and rising to 23° C. in the last few days of the experiment. There was no significant difference between the mean temperatures from the monitors placed with the three or four year old trees (P=0.05). Minimum temperatures were similar, however, the mean maximum temperatures were slightly higher (P=0.05) for the monitor amongst the three year old trees compared to the larger trees. Virtually all the insects recovered were 6$^{th}$ instars.

Figure 11:
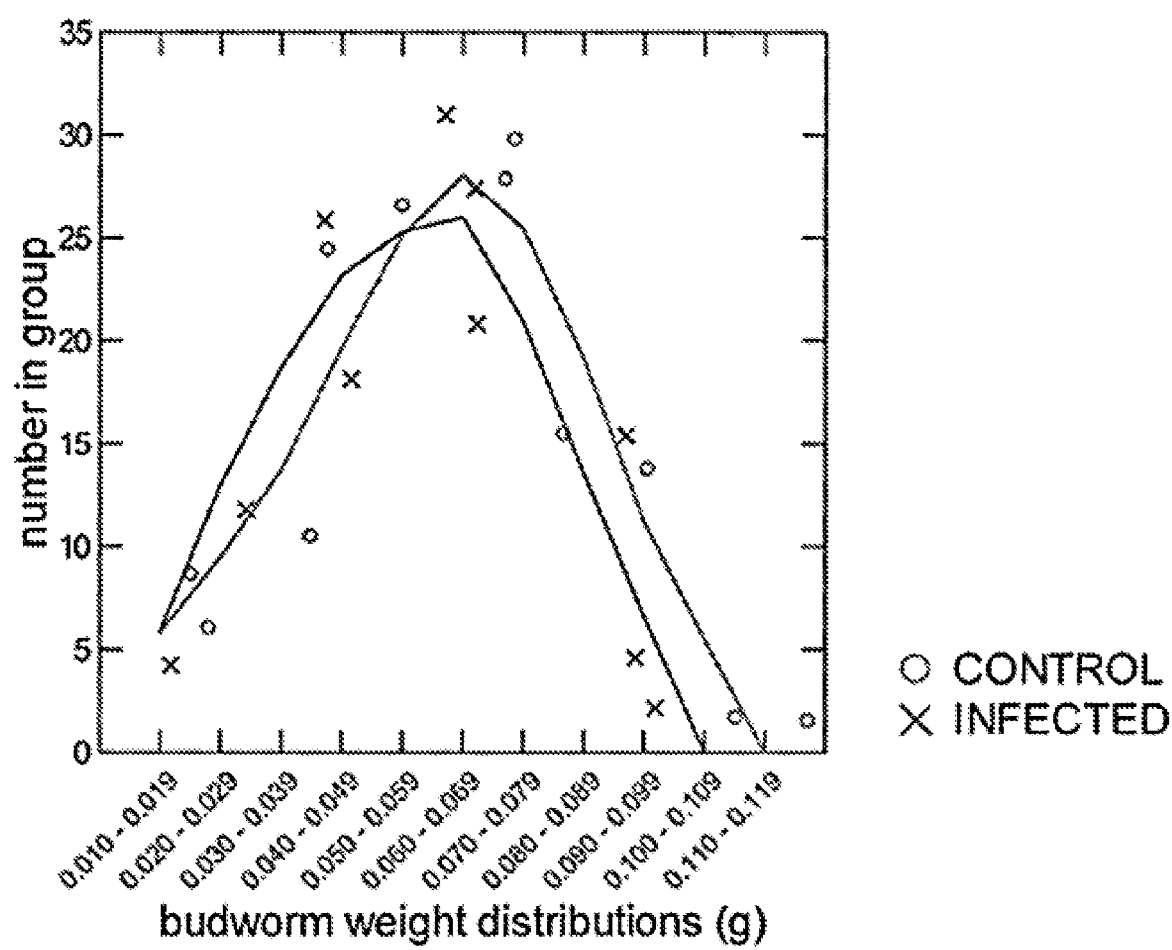
FIG. 11 is a graph showing distribution of insect weights between endophyte-infected and uninfected three year old trees; the weights between the two groups were significantly different by ANOVA, $P=0.018 invention also provides novel toxigenic endophyte strains, inoculum compositions and toxigenic, endophyte-colonized conifer plants.

Three year old trees: ELISA analysis of the control group revealed that 5 of the endophyte negative trees were positive at 36 months, i.e. were false negatives when previously tested. These were excluded from the analysis. The geometric mean toxin concentration corrected for recovery in the endophyte positive group was 0.85 µg/g. The number of budworm recovered per tree was 3.3 for the infected (161 total) and 3.5 for the uninfected trees (152 total). Analysis of variance indicated that the weights of treated and control budworms were significantly different (P=0.018; DF=1; F-ratio 5.64). The distribution of insect weights between endophyte-infected and uninfected three year old trees is shown in FIG. 11. Mean weight of the controls at termination was 0.061±0.02 mg and 0.055±0.02 mg for those collected on the infected trees. This difference was statistically different (P=0.009, equal-variance t-test). Mean head capsule widths for the controls were 1.89±0.21 mm and 1.90±0.18 mm. These were not significantly different by ANOVA.

Four year old trees: The geometric mean rugulosin concentration corrected for recovery was 0.8 µg g$^{-1}$ in all samples and the mean of the positives≥0.5 µg g$^{-1}$ was 1.3 µg g$^{-1}$. By ANOVA, there was no significant interaction between tree and insect weight, or, tree and rugulosin concentration. Mean weight of the 166 insects recovered from the four year old trees was 0.072±0.02 mg. Considering the branches above and below 0.5 µg g$^{-1}$, there was an inverse relationship between rugulosin concentration and budworm weight (Pearson correlation −0.288; Bonferroni-adjusted P=0.023). Head capsule widths averaged 1.95±0.15 mg.

An average of 1.4 budworms was recovered from the original two placed on each branch. When the branches were stratified into quartiles of rugulosin concentration (40 each), the proportion of branches with one budworm was lower between the bottom and top three quartiles (Wilcoxon signed rank test, P=0.025).

Disregarding a few trees where budworms were collected from only one branch, the trees fell into one of three distributions. The largest percentage (38%) comprised the situation where all branches were above the threshold of rugulosin toxicity and 16% were all below the threshold. In neither case would there be intra-tree variation to study. The remainder had individual branches above and below. Typical data from trees with multiple branches analyzed are shown in Table 4. All three branches analyzed on tree 1034 had concentrations far in excess of the toxic threshold. Only one budworm per branch was recovered and the animal from the branch with the lowest concentration had the highest weight, higher than the mean noted above. One branch from tree 1360 was far above the threshold. In this case, the weight of the insect collected was at the mean. Two insects were collected from the two remaining branches with a mean weight at the average. A similar pattern can be seen in tree 2022.

Discussion

The inventors have examined two aspects the effect of rugulosin in needles on *C. fumerana* growth under outdoor nursery conditions. The first was a comparison of the impact on budworm growth on infected trees and uninfected trees. The second was to use a group of older trees such that needles from the infected tree served as a control. This strategy is typically used in toxicology to eliminate possible confounding variables arising from intra-individual variance. These might be anticipated to result from potential changes in needle chemistry due to variables including needle age and shade and the fungus itself. The inventors have shown a dose-response to rugulosin.

Shading (Lhotakova et al. 2007) and needle age as well as soil conditions are known to affect foliar composition and these in turn can affect budworm growth (Carisey and Bauce, 1997; Clancy et al., 2004; Nealis and Nault, 2005). The trees used in the present studies represented a diverse genetic population used for reforestation in eastern Canada and Maine. In growth chamber studies, occurrence of the fungus and its toxin in needles reduced *C. fumerana* growth. These latter experiments were done using detached needles from four month old seedlings using an established method to screen for variation in foliar resistance (Miller et al., 2002). The present experiments were conducted by placing budworm on trees that grow outdoors.

Although an attempt was made to terminate the experiment such that ca. 20% would were $6^{th}$ so that was a distribution of instars, virtually all were $6^{th}$ instars. This is probably because of higher temperatures in the final 24 h of the experiments compared to the previous week. Mean head capsule widths were ~1.94 mm. This value is on the upper end of those found in nature. McGugan (1954) reported that the mean head capsule widths from a natural epidemic in northwestern Ontario were 1.63 mm for males and 1.79 mm for females. Field collections from New Brunswick were reported to be 1.66 mm without sex being specified (Anon. 1981. Data Fact Sheet, Determination of spruce budworm larval stage; CANUSA Spruce Budworm Program). This difference may relate to the fact that the animals used in this experiment were parasite- and disease-free versus the natural situation (see following).

The distribution of animal weights collected on infected needles at termination was different than the respective controls (FIG. 11). There was also a statistically-significant difference in budworm weights between the two groups. As in the growth chamber, the presence of the fungus and its toxin reduced *C. fumerana* growth. Similar experiments on infected and unifected grass endophytes have resulted in similar findings as well as effects on development (e.g. Hardy et al. 1986).

The second aspect of the present experiments was the use of older trees from which the effect on budworm growth on multiple branches from the same infected tree could be observed. This was possible because there both in the present and previous experiments, variation in rugulosin concentration was observed between individual branches within a single trees. As was found previously, rugulosin concentration on a molar basis was typically above those that affect growth of *C. fumerana, Lambdina fiscellaria* and *Zeiraphera canadensis* in vitro. In this component of the study, two effects were seen.

A comparison of those branches with concentrations above and below the threshold of rugulosin toxicity demonstrated there was an inverse relationship between budworm weight and rugulosin concentration (−0.288; P=0.023). A further support of the reliability of this conclusion comes in the fact that the branches with the highest rugulosin concentrations, survival was significantly lower than on branches those with lower concentrations. In addition, there was a small but significant increased weight in the survivor population found on branches in the quartile of branches with the highest rugulosin concentration. It is known that when *C. fumerana* are under nutrient limitations, they will resort to cannibalism which provides a plausible explanation of the latter observation. None the less, there was still evidence of a rugulosin dose-response where single animals were recovered (e.g. tree 1034B).

In synthetic diet (Calhoun et al. 1992), the presence of rugulosin at ca. 50 μM results in the reduction in *C. fumerana* growth rate. Using the weight of evidence rule in toxicology, the effects seen in this study are largely explained by the toxin, and are consistent with other endophyte-interactions that have been studied.

In summary, for the first time the inventors have shown that the presence of a foliar endophyte of conifers and its toxin, rugulosin, in trees grown under production conditions resulted reduced growth of *C. fumerana* in a dose-dependent manner. In addition, these experiments show that the effect is primarily explained by rugulosin.

TABLE 4

Budworm weights on different branches from four-year old trees and rugulosin concentration.

| tree | branch | budworm | weight mg | rugulosin μg $g^{-1}$ |
|---|---|---|---|---|
| 1034B | 1 | 1 | 0.061 | 4.20 |
| 1034B | 2 | 1 | 0.114 | 1.53 |
| 1034B | 3 | 1 | 0.067 | 3.59 |
| 1040B | 1 | 1 | 0.081 | 0.09* |
| 1040B | 2 | 2 | 0.045 | 0.39* |
| 1040B | 2 | 1 | 0.044 | 0.39* |
| 1040B | 3 | 1 | 0.038 | 0.87 |
| 1148B | 1 | 1 | 0.116 | 0.09* |
| 1148B | 3 | 1 | 0.052 | 1.29 |

TABLE 4-continued Budworm weights on different branches from four-year old trees and rugulosin concentration.

| tree | branch | budworm | weight mg | rugulosin µg g$^{-1}$ |
|---|---|---|---|---|
| 1148B | 3 | 2 | | |
| 1171B | 1 | 1 | 0.028 | 0.89 |
| 1171B | 1 | 2 | 0.083 | 0.89 |
| 1171B | 2 | 1 | 0.048 | 2.27 |
| 1360B | 1 | 1 | 0.072 | 3.55 |
| 1360B | 2 | 2 | 0.062 | 0.09* |
| 1360B | 2 | 1 | 0.077 | 0.09* |
| 1360B | 3 | 1 | 0.061 | 0.09* |
| 1360B | 3 | 2 | 0.080 | 0.09* |
| 2022B | 1 | 1 | 0.035 | 10.21 |
| 2022B | 2 | 1 | 0.057 | 0.17* |
| 2022B | 3 | 2 | 0.072 | 0.17* |
| 2022B | 3 | 1 | 0.066 | 0.17* |

*below dietary concentration of threshold for toxicity of rugulosin in vitro

All publications, patents and patent applications are herein incorporated by reference in their entirety to the same extent as if each individual publication, patent or patent application was specifically and individually indicated to be incorporated by reference in its entirety.

REFERENCES

Binder E M, Binder J, Ellend N, Schaffer E, Krska R, Braun R, 1996. Microbiological degradation of deoxynivalenol and 3-acetyl-deoxynivalenol. In: Miraglia M, van Egmond H, Brera C, Gilbert J (eds) *Mycotoxins and phycotoxins—Developments in chemistry, toxicology and food safety*. Fort Collins, Colo., pp. 279-285.

Bouhet J C, Van Chuong P P, Toma F, Kirszenbaum M, Fromageot P, 1976. Isolation and characterization of luteoskyrin and rugulosin, two hepatotoxic anthraquinonoids from *Penicillium islandicum* Sopp. and *Penicillium rugulosum* Thom. *Journal of Agricultural Food Chemistry* 24:964-972.

Breen J, Dacre J C, Raistrick H, Smith G, 1955. Studies in the biochemistry of micro-organisms. 95. Rugulosin, a crystalline colouring matter of *Penicillium rugulosum* Thom Biochemical Journal 60:618-626.

Calhoun L A, Findlay J A, Miller J D, Whitney J D (1992) Metabolites toxic to spruce budworm from balsam fir needle endophytes. Mycological Research 96: 281-286.

CARISEY, N. and BAUCE, E. 1997. Balsam fir foliar chemistry in middle and lower crowns and *C. fumerana* growth, development, food and nitrogen utilization. *J. Chem. Ecol.* 23:1963-1978.

Carroll G C, Carroll F E (1978) Studies on the incidence of coniferous needle endophytes in the Pacific Northwest. Can J Botany, 1978, 56:3034-3043.

Carroll G C. 1979. Needle microepiphytes in a Douglas fir canopy: biomass and distribution patterns. Can J Bot 57:1000-1007.

Carroll G C 1988. Fungal endophytes in stems and leaves: from latent pathogen to mutualistic symbiont. Ecology 69:2-9.

Clark C, Miller J D, Whitney N J (1989) Toxicity of conifer needle endophytes to spruce budworm. Mycological Research 93: 508-512.

Clay K. 1988. Fungal endophytes of grasses: a defensive mutualism between plants and fungi. Ecology 69:10-16.

Clay K, Holah J. 1999. Fungal endophyte symbiosis and plant diversity in successional fields. Science 285:1742-1744.

Clay K, Schardl C, 2002. Evolutionary origins and ecological consequences of endophyte symbiosis with grasses. American Naturalist 160: S99-S127.

CLANCY, K. M., CHEN, Z., and KOLB, T. E. 2004. Foliar nutrients and induced susceptibility: genetic mechanisms of Douglas-fir resistance to western *C. fumerana* defoliation. *Can. J. Forest Res.* 34:939-949, 2004.

Dobias J, Betina V, Nemec P 1980, Insecticidal activity of ramihyfin A, citrinin, and rugulosin. Biologia 35:431-434.

Findlay J A, Li G, Penner P E, Miller J D (1994) Novel diterpenoid insect toxins from a conifer endophyte. J Natural Products 58:197-200.

Findlay J A, Buthelezi S, Lavoie R, Pena-Rodrigues L, Miller J D (1995) Bioactive isocoumarins and related metabolites from conifer endophytes. J Natural Products 58:1759-1766.

Findlay J A, Li G, Penner P E, Miller J D (1995) Novel Diterpenoid Insect Toxins from a Conifer Endophyte. Journal of Natural Products, 58: 197-200).

Findlay J A, Butelezi S, Li Q, Seveck M, Miller J D (1997) Insect toxins from an endophytic fungus from Wintergreen. J Natural Products 60:1214-1215.

Findlay J A, Li G, Miller J D, Womilouju T O (2003A) Insect toxins from spruce endophytes. Can J Chemistry 81:284-292.

Findlay J A, Lia G, Miller J D, Womiloju T (2003B). Insect toxins from conifer endophytes. In: Yayli N, Küçük M (eds) Proceedings of the 1$^{st}$ International Congress on the Chemistry of Natural Products (ICNP-2002) Karadeniz Technical University, Trabzon, Turkey. p. 13-16.

Frisvad J C and Thrane U (1987): Standardized HPLC of 182 mycotoxins>and other fungal metabolites based on alkylphenone retention indicies>and UV-VIS spectra (DAD). J. Chromatography 28:404(1): 195-214.

Ganley R J, Brunsfeld S J, Newcombe G. 2004. A community of unknown, endophytic fungi in Western White pine. Proceedings of the National Academy of Sciences of the United States of America 101:10107-10112.

Gessner M O, Newell S Y. 2002. Biomass, growth rate, and production of filamentous fungi in plant litter. Manual of Environmental Microbiology (2nd Edition) p 390-408.

Glass N L, Donaldson G C (1995). Development of Primer Sets Designed for Use with the PCR To Amplify Conserved Genes from Filamentous Ascomycetes. Applied and Environmental Microbiology61: 1323-1330.

Gruenig C R, Sieber T N, Rogers S O, Holdenrieder O, 2002. Genetic variability among strains of *Phialocephala fortinii* and phylogenetic analysis of the genus *Phialocephala* based on rDNA ITS sequence comparisons. *Canadian Journal of Botany* 80:1239-1249.

Gwinn K D, Collins-Shephard H M, Reddick B B. 1991. Tissue print-immunoblot, an accurate method for the detection of *Acremonium coenophialum* in tall fescue. Phytopathology 81:747-748.

HARDY, T. N., CLAY, K., HAMMOND, A.M. 1985. Fall armyworm (Lepidoptera, Noctuidae)—a laboratory bioassay and larval preference study for the fungal endophyte of perennial ryegrass. J. Economic Entomology 78:571-575.

Higgins, 2007

Johnson J A, Whitney N J, 1989. A study of fungal endophytes of needles of balsam fir (*Abies balsamea*) and red spruce (*Picea rubens*) in New Brunswick, Canada, using culture and electron microscope techniques. *Canadian Journal of Botany* 67:3513-3516.

LHOTAKOVA, Z., ALBRECHTOVA, J., MALENOVOSKY, Z., ROCK, B. N., POLAKA, T. and CUDLIN, P. 2007. Does the azimuth orientation of Norway spruce (*Picea*

*abies*/L./Karst.) branches within sunlit crown part influence the heterogeneity of biochemical, structural and spectral characteristics of needles? Environmental and Experimental Botany 59:283-292.

McGugan B M, 1954. Needle-mining habits and larval instars of the spruce budworm. Canadian Entomologist 36: 439-454.

McMorran, A., 1965. A synthetic diet for the spruce budworm, *Choristoneura fumiferana* (Clem.) (Lepidoptera: Tortricidae). The Canadian Entomologist 97, 58-62.

Miller J D, Young J C, Trenholm H L. 1983. *Fusarium* toxins in field corn. I. Parameters associated with fungal growth and production of deoxynivaneol and other mycotoxins. Can J Botany 61:3080-3087.

Miller J D, Strongman D, Whitney N J. 1985. Observations on fungi associated with spruce budworm infested balsam fir needles. Can J Forest Res 15:896 901.

Miller J D, Mackenzie S. 2000. Secondary metabolites of *Fusarium venenatum* strains with deletions in the Tri5 gene encoding trichodiene synthetase. Mycologia 92:764-771.

Miller J D, Mackenzie S, Foto M, Adams G W, Findlay J A (2002) Needles of white spruce inoculated with rugulosin-producing endophytes contain rugulosin reducing spruce budworm growth rate. Mycological Research 106:471-479.

Morita H C, Singh H, Fulger R G, 1984. Detection of the mycotoxin zearalenone in fungal hyphae by fluorescence microscopy. Canadian Journal of Plant Pathology 6:179-181.

Mortensen G K, Strobel B W, Hansen H C B, 2006. Degradation of zearalenone and ochratoxin A in three Danish agricultural soils. Chemosphere 62:1673-1680.

NEALIS, V. G. and NAULT, J. R. 2005. Seasonal changes in foliar terpenes indicate suitability of Douglas-fir buds for western *C. fumerana*. J. Chem. Ecol. 31:683-696.

PANACCIONE, D. G., KOTOCON, J. B., SCHARDL, C. L., JOHNSON, R. D. and MORTON, J. B. 2006 Ergot alkaloids are not essential for endophytic fungus-associated population suppression of the lesion nematode, *Pratylenchus scribneri*, on perennial ryegrass Nematology 8: 583-590.

PARSONS, K., QUIRING, D., PIENE, H. and MOREAU, G. 2005. Relationship between balsam fir sawfly density and defoliation in balsam fir. For. Ecol. Management. 205:325-331.

Petrini O. 1991 Fungal endophytes of tree leaves. In: Andrews J H & Hirano S S (eds) Microbial Ecology of Leaves. Springer Verlag, New York. pp. 179-197.

Todd D (1988) The effects of host genotype, growth rate, and needle>age on the distribution of a mutalistic, endophytic fungus in Douglas>fir plantations, Canadian Journal of Forestry Research 18, 601-605.

QUAYLE, D., REGNIERE, J., CAPPUCCINO, N. and DUPONT, A. 2003. Forest composition, host-population density and parasitism of *C. fumerana Choristoneura fumiferana* eggs by *Trichogramma minutum*. Entomol. experimentalis et applicata 107:215-227.

Reddick B B, Collins M H. 1988. An improved method for detectionm of *Acremonium coenophialum* in tall fescue plants. Phytopathology 78:418-420.

ROTTINGHAUSE, G. E., GARNER, G. B., CORNELL, C. N. and ELLIS, J. L. 1991. HPLC method for quantitating ergovaline in endophyte-infested tall fescue: seasonal variation of ergovaline levels in stems with leaf sheaths, leaf blades and seed heads. J. Agric. Food Chem. 39: 112-115.

Royama T, 1984. Population dynamics of the spruce budworm *Choristoneura fumiferana*. Ecological Monographs 54:429-462

Royama T, MacKinnon W E, Kettela E G, Carter N E, Hartling L K, 2005. Analysis of spruce budworm outbreak cycles in New Brunswick, Canada, since 1952. Ecology 86:1212-1224.

Sanchez-Ballesteros, J., Gonzalez, V., Salazar, O., Acero, J. Portal, M. A., Julian, M., Rubio, V., Bills, G. F., Polishook, J. D., Platas, G., Mochales, S., Pelaez, F. 2000, Phylogenetic Study of Hypoxylon and Related Genera Based on Ribosomal ITS Sequences. Mycologia, 92(5): 964-977

SHEPHERD, R. F. 1959. Phytosociological and environmental characteristics of outbreak and non-outbreak areas of the two-year cycle *C. fumerana, Choristoneura fumiferana*. Ecology 40:608-620.

Sherwood-Pike, M, Stone J K and Carroll, G C (1986) *Rhabdocline parkeri*, a ubiquitous foliar endophyte of Douglas fir. Canadian Journal of Botany 64, 1849-1855.

SPIERINGS, M. J., LANE, G. A., CHRISTENSEN, M. J, and SCHMIDT, J. 2005. Distribution of the fungal endophyte *Neotyphodium lolii* is not a major determinant of the distribution of fungal alkaloids in *Lolium perenne* plants. Phytochem. 66: 195-202.

Stark A A, Townsend J M, Wogan G N, Demain A L, Manmade A, Ghosh A C, 1978. Mutagenicity and antibacterial activity of mycotoxins produced by *Penicillium islandicum* and *Penicillium rugulosum*. Journal Environmental Pathology Toxicology 2:313-324.

STRONGMAN, D. B., EVERLEIGH, E. S., VAN FRANKENHUYZEN, K. and ROYAMA, T. 1997. The occurrence of two types of entomopathogenic bacilli in natural populations of the *C. fumerana, Choristoneura fumiferana*. Can. J. For. Res. 27:1922-1927.

Sumarah M W, Miller J D, Adams G W, 2005. Measurement of a rugulosin-producing endophyte in white spruce seedlings. Mycologia 97:770-776.

SUMARAH, M. W., PUNIANI, E., BLACKWELL, B. A., and MILLER, J. D. 2008A. Characterization of metabolites from foliar endophytes of white spruce. J. Natural Products (submitted)

Swisher R, Carroll G C. 1990. Fluorescein diacetate hydrolysis as an estimator of microbial biomass on coniferous needle surfaces. Microbial Ecology 6:217-226.

Takemoto D, Tanaka A, Scott B A, 2006. A $p67^{Phox}$-like Regulator is recruited to control hyphal branching in a fungal-grass mutualistic symbiosis. Plant Cell 18:2807-2821.

Thomas A W (1983) Foliage consumed by $6^{th}$ instar spruce budworm larvae, *Choristoneua fumiferana* (Clem.), feeding on balsam fir and white spruce. Forest defoliator-host interactions: a comparison between gypsy moth and spruce budworm (ed. Talerico R L). pp. 47-48. United States Department of Agriculture General Technical Report NE-85, New Haven, Conn.

Turner W B, Aldridge D C. 1983. Fungal Metabolites II. Academic Press Inc. New York. pp. 152.

Ueno Y, Ueno I, Sato N, litoi Y, Saito M, Enomoto M, Tsunoda H, 1971. Toxicological approach to (+)-rugulosin, an anthraquinoid mycotoxin of *Penicillium rugulosum*. Japanese Journal of Experimental Medicine 41(3) 177-88.

Ueno Y, Sato N, Ito T, Ueno I, Enomoto M, Tsunoda H, 1980. Chronic toxicity and hepatocarcinogenicity of (+) rugulosin, an anthraquinoid mycotoxin from *penicillium* species: preliminary surveys in mice. Journal Toxicological Science 5:295-302.

Vasiliauskas, R., Larsson, E., Larsson, K. H., Stenlid, J. 2005, >Persistence and long-term impact of Rotstop biological control agent on >mycodiversity in *Picea abies* stump. Biological Control 32:295-304.

Vincent J G, Vincent H W 1944. Filter paper disc modification of the Oxford cup penicillin determination Prof Soc Exp Biology Med 55162-164

Watts P, Kittakoop P, Veeranondha S, Wanasith S, Thongwichian R, Saisaha P, Intamas S, Hywel-Jones N L, 2003. Cytotoxicity against insect cells of entomopathogenic fungi of the genera *Hypocrella* (anamorph *Aschersonia*): possible agents for biological control. *Mycological Research* 107: 581-586.

Wilson R, Wheatcroft R, Miller J D, Whitney N J. 1994. Genetic diversity among natural populations of endophytic *Lophodermium pinastri* from *Pinus resinosa*. Mycol. Res 98(7):740-744.

The invention claimed is:

1. A method of preparing a conifer seedling with increased tolerance to an insect or fungal pest, comprising
   a) inoculating
      i) an intact nursery grown conifer seedling by spraying; or
      ii) soaking a conifer seed;
   with an inoculum composition comprising an isolated toxigenic endophyte during a susceptible time window, which susceptible time window is during: i) seed stratification or ii) post germination to the period when the cuticle is fully formed, wherein the inoculating step comprises contacting the seedling with an inoculum composition under an environment of sustained wetness that soaks the seed or sustains needle wetness, and
   b) growing the conifer seeding or conifer seed to obtain the conifer seedling with increased tolerance to an insect or fungal pest;
   wherein the toxigenic endophyte is an endophyte that reduces spruce budworm weight and/or head capsule width by at least 10% in a spruce budworm larvae assay compared to a control endophyte; and
   wherein the increase tolerance is relative to a conifer seedling grown from an uninoculated conifer seedling or seed.

2. The method of claim 1 wherein the inoculum composition comprises the toxigenic endophyte, as hyphal fragments and the inoculum composition comprises at least 1-25 toxigenic endophyte hyphal fragments/6 microliter, optionally at least 1-4 toxigenic endophyte hyphal fragments/microliter, optionally at least 0.2-4 toxigenic endophyte hyphal fragments/microliter, or at least 3 toxigenic endophyte hyphal fragments per 6 microliter.

3. The method of claim 1 wherein the inoculating step comprises spraying the seedling with the inoculum.

4. The method of claim 1 wherein the conifer seed is contacted with the isolated toxigenic endophyte by soaking the seed in a solution comprising the toxigenic endophyte.

5. The method of claim 1 comprising repeating the inoculation step.

6. The method of claim 1, wherein the seedling or seed is grown in a greenhouse until the toxigenic endophyte is present in an amount adequate to reduce pest growth rate, pest development and/or reduce pest weight gain compared to pest growth in a non-inoculated conifer seedling.

7. The method of claim 1, wherein the toxigenic endophyte produces at least one toxin compound selected from the group consisting of rugulosin, vermiculin, 5-methoxycarbonylmellein, 5-formylmellein, 5-methylmellein, 3-butyl-4-methylfuran-2(5H)-one butyrolactone tyrosol, mellein, 8-hydroxy-6-methoxy-3-propyl-3, 4-dihydroisocoumarin, and 3-methyl-5,7-dimethoxyphthalide,.

8. The method of claim 7 wherein the toxin compound is rugulosin or vermiculin and the seedling or seed is grown until the toxin compound is present in conifer needles in an amount of at least 0.15 microgram per gram of needle or at least 10 micromolar.

9. The method of claim 1, wherein the toxigenic endophyte is a species of *Phialocephala, Xylariaceae*, or *Lophodermium*.

10. The method of claim 1, wherein the toxigenic endophyte is selected from the group consisting of toxigenic endophytes deposited with the Centraal bureau voor Schimmelcultures (CBS) international depository agency in the Netherlands, having the accession numbers consisting of CBS120377, CBS120378, CBS120379, CBS120380, CBS120381, CBS121942, CBS121943, CBS121944, CBS121945 and CBS121946.

11. The method of claim 1 wherein the conifer seedling or conifer seed is a spruce seedling or seed, optionally a white spruce seedling or seed or a red spruce seedling or seed.

12. The method of claim 11, wherein the conifer seedling is susceptible when the seedling is at least 2 cm high and less than 10 cm high, optionally less than 6 cm high.

13. The method of claim 1, wherein the conifer seedling comprises a fir or pine conifer seedling.

14. The method of claim 11, wherein the spruce seedling or seed is a white spruce seedling or seed and the white spruce seedling or seed is inoculated with a toxigenic endophyte isolated from a white spruce optionally selected from the group consisting of toxigenic endophytes deposited with the Centraal bureau voor Schimmelcultures (CBS) international depository agency in the Netherlands, having the accession numbers consisting of CBS120377, CBS120378, CBS120379, CBS120380 and CBS120381.

15. The method of claim 1, wherein the insect or fungal pest is selected from the group consisting of spruce budworm, hemlock looper, spruce budmoth, sawflies, jack pine budworm and disease causing fungal pathogens.

16. The method of claim 1 wherein the inoculating step is preceded by isolating the toxigenic endophyte from a donating plant and culturing the toxigenic endophyte, optionally wherein the step of isolating a toxigenic endophyte from a donating plant comprises: isolating a candidate toxigenic endophyte from needles of the donating plant; assaying for toxicity of the candidate endophyte to a pest in a pest toxicity assay wherein toxicity of the candidate endophyte is indicative that the candidate toxigenic endophyte is a toxigenic endophyte.

17. A method of preparing a conifer seedling with increased tolerance to an insect or fungal pest, comprising
   a) inoculating
      i) an intact nursery grown conifer seedling by spraying; or
      ii) soaking a conifer seed;
   with an inoculum composition comprising an isolated toxigenic endophyte during a susceptible time window, which susceptible time window is during: i) seed stratification or ii) post germination to the period when the cuticle is fully formed, wherein the inoculating step comprises contacting the seedling with an inoculum composition under environmental conditions that soak the seed or sustain needle wetness, and
   b) growing the conifer seeding or conifer seed to obtain the conifer seedling with increased tolerance to an insect or fungal pest;
   wherein the toxigenic endophyte is an endophyte that reduces spruce budworm weight and/or head capsule width by at least 10% in a spruce budworm larvae assay compared to a control endophyte;
   wherein the increase tolerance is relative to a conifer seedling grown from an uninoculated conifer seedling or seed;
   wherein the conifer seedling or conifer seed is a spruce seedling or seed, optionally a white spruce seedling or seed or a red spruce seedling or seed; and
   wherein the spruce seedling is a red spruce seedling or seed and the red spruce seedling or seed is inoculated with a toxigenic endophyte selected from the group consisting of toxigenic endophytes deposited with the Centraal bureau voor Schimmelcultures (CBS) international depository agency in the Netherlands, having the accession numbers consisting of CBS121942, CBS121943, CBS121944, CBS121945 and CBS121946.

* * * * *

UNITED STATES PATENT AND TRADEMARK OFFICE
CERTIFICATE OF CORRECTION

PATENT NO. : 10,674,699 B2  
APPLICATION NO. : 15/389125  
DATED : June 9, 2020  
INVENTOR(S) : John David Miller and Greg William Adams It is certified that error appears in the above-identified patent and that said Letters Patent is hereby corrected as shown below:

In the Specification

Column 3, Line 47 "toxicgenic" should read --"toxigenic"--.

Column 5, Line 24 "confer pert" should read --"conifer pest"--.

Column 7, Line 3 "embodiment, embodiment," should read --"embodiment,"--.

Column 15, Line 29 "deTected" should read --"detected"--.

Column 18, Line 38 "The term" should be moved to a new line.

Column 18, Line 54 "(Drosophila melanogaster" should read --"(Drosophila melanogaster)"--.

Column 19, Line 62 "contacting an an endophyte" should read --"contacting an endophyte"--.

Column 24, Line 58 "as describe" should read --"as described"--.

Column 26, Line 16 "Reddick & Collins 1998." should read --"Reddick & Collins 1998)."--.

Column 26, Line 64 "in planta" should read --*in planta*--.

Column 30, Line 49 "as describe above" should read --"as described above"--.

Column 31, Line 37 "Miller et al., 2002)." should read --"Miller et al., 2002."--.

Column 33, Line 10 "the plant plant applied" should read --"the plant applied"--.

Column 34, Lines 39-40 "seedlings (Sumarah et al. 2005)" should read --"seedlings, Sumarah et al. 2005)"--.

Signed and Sealed this  
Eighth Day of June, 2021

Drew Hirshfeld  
*Performing the Functions and Duties of the*  
*Under Secretary of Commerce for Intellectual Property and*  
*Director of the United States Patent and Trademark Office*

CERTIFICATE OF CORRECTION (continued)
U.S. Pat. No. 10,674,699 B2

Column 35, Line 46 "seedlings in were" should read --"seedlings were"--.

Column 41, Line 13 "(based he" should read --"(based on"--.

Column 42, Line 40 "Samples taken trees" should read --"Samples taken from trees"--.

Column 43, Lines 50-51 "in planta" should read --*"in planta"*--.

Column 47, Line 30 "aspects the effect" should read --"aspects of the effect"--.

Column 47, Line 56 "would were 6th" should read --"were 6th"--.

Column 48, Line 19 "a single trees" should read --"a single tree"--.